US012667675B2

(12) United States Patent
Lane et al.

(10) Patent No.: US 12,667,675 B2
(45) Date of Patent: Jun. 30, 2026

(54) SYSTEMS, APPARATUS, AND METHODS FOR WARMING FLUID FOR INTRAVENOUS INFUSION

(71) Applicant: 410 Medical, Inc., Durham, NC (US)

(72) Inventors: Andrew W. Lane, Rolesville, NC (US); Galen C. Robertson, Apex, NC (US); Savannah K. Steele, Durham, NC (US); Luke D. Oltmans, Durham, NC (US); Kevin A. Harper, Mason, OH (US); Steve D. Ivanov, Youngsville, NC (US); Matthew J. Hanlon, Clifton, VA (US)

(73) Assignee: 410 Medical, Inc., Durham, NC (US)

( * ) Notice: Subject to any disclaimer, the term of this patent is extended or adjusted under 35 U.S.C. 154(b) by 0 days.

(21) Appl. No.: 19/232,175

(22) Filed: Jun. 9, 2025

(65) Prior Publication Data

US 2025/0295867 A1     Sep. 25, 2025

Related U.S. Application Data

(63) Continuation of application No. 18/959,439, filed on Nov. 25, 2024, which is a continuation of application No. PCT/US2023/067515, filed on May 25, 2023.

(Continued)

(51) Int. Cl.
*A61M 5/44*          (2006.01)

(52) U.S. Cl.
CPC ....... *A61M 5/44* (2013.01); *A61M 2205/0233* (2013.01); *A61M 2205/3653* (2013.01)

(58) Field of Classification Search
CPC ..... F24H 1/20; F24H 1/18; F24H 1/22; F24H 1/208; A61M 2205/0233;

(Continued)

(56) References Cited

U.S. PATENT DOCUMENTS 1,966,133 A * 7/1934 Pieper .................... F24D 3/087
                                                    165/162
2,266,216 A * 12/1941 Kimberlin ................ H05B 3/06
                                                    392/497

(Continued)

FOREIGN PATENT DOCUMENTS

EP          3854432 A1     7/2021
JP        2000511075 A     8/2000

(Continued)

OTHER PUBLICATIONS

International Preliminary Report on Patentability for International Application No. PCT/US2023/067515 mailed Dec. 5, 2024, 16 pages.

(Continued)

*Primary Examiner* — Quynh-Nhu H. Vu
(74) *Attorney, Agent, or Firm* — COOLEY LLP

(57)          ABSTRACT

In some embodiments, a system includes a housing, an elongated heating element, a first electrical connector, and a second electrical connector. The housing can define a fluid channel extending from a fluid inlet to a fluid outlet. The elongated heating element can be disposed within the fluid channel. The first electrical connector can be electrically coupled to a first portion of the elongated heating element and the second electrical connector can be electrically coupled to a second portion of the elongated heating element. Energy can be provided from a power source to the elongated heating element via one of the first electrical connector or the second electrical connector to increase the temperature of the elongated heating element.

20 Claims, 46 Drawing Sheets

Related U.S. Application Data

(60) Provisional application No. 63/345,844, filed on May 25, 2022.

(58) Field of Classification Search
CPC ...... A61M 2205/3653; A61M 2205/36; A61M 2205/3613; A61M 5/44; A61M 5/445; A61M 2205/366
See application file for complete search history.

(56) References Cited

U.S. PATENT DOCUMENTS

| | | | |
|---|---|---|---|
| 2,640,138 A * | 5/1953 | Merritt | F02N 19/10 |
| | | | 123/142.5 R |
| 3,293,869 A * | 12/1966 | Karbosky | F25J 3/0645 |
| | | | 62/620 |
| 3,590,215 A * | 6/1971 | Anderson | A61M 5/44 |
| | | | 392/479 |
| 4,038,519 A | 7/1977 | Foucras | |
| 4,574,876 A * | 3/1986 | Aid | A61M 5/44 |
| | | | 165/917 |
| 4,577,683 A * | 3/1986 | Kelch | F28D 9/04 |
| | | | 165/170 |
| 4,742,870 A * | 5/1988 | Darone | F28D 9/0037 |
| | | | 165/170 |
| 4,777,683 A * | 10/1988 | Pellerin | D06F 39/087 |
| | | | 8/158 |
| 4,808,077 A | 2/1989 | Kan et al. | |
| 4,907,145 A | 3/1990 | Cassidy | |
| 4,919,649 A | 4/1990 | Timothy et al. | |
| 5,319,170 A | 6/1994 | Cassidy | |
| 5,713,864 A | 2/1998 | Verkaart | |
| 5,840,068 A | 11/1998 | Cartledge | |
| 5,913,814 A | 6/1999 | Zantos | |
| 6,080,973 A * | 6/2000 | Thweatt, Jr. | F24H 15/37 |
| | | | 219/505 |
| 6,139,528 A | 10/2000 | Kistner et al. | |
| 6,142,974 A * | 11/2000 | Kistner | F28F 27/00 |
| | | | 604/113 |
| 6,175,688 B1 | 1/2001 | Cassidy et al. | |
| 6,257,265 B1 | 7/2001 | Brunner et al. | |
| D447,558 S | 9/2001 | Cartledge et al. | |
| D462,121 S | 8/2002 | Cartledge et al. | |
| 6,500,200 B1 | 12/2002 | Kushnir | |
| 6,508,831 B1 | 1/2003 | Kushnir | |
| 6,554,791 B1 | 4/2003 | Cartledge et al. | |
| 6,591,063 B2 | 7/2003 | Rochelle | |
| 6,641,556 B1 | 11/2003 | Shigezawa | |
| 6,685,731 B2 | 2/2004 | Kushnir et al. | |
| 6,873,793 B2 | 3/2005 | Thweatt, Jr. | |
| 7,357,786 B1 | 4/2008 | Bakke | |
| 7,563,248 B2 | 7/2009 | Smisson, III et al. | |
| 7,570,314 B2 | 8/2009 | Lee | |
| 7,731,689 B2 | 6/2010 | Prisco et al. | |
| 7,753,885 B2 | 7/2010 | Duchon et al. | |
| 7,819,835 B2 | 10/2010 | Landy et al. | |
| 7,846,130 B2 | 12/2010 | Elazari-Volcani et al. | |
| 7,891,974 B2 | 2/2011 | Gill et al. | |
| 7,951,112 B2 | 5/2011 | Patzer | |
| 7,975,491 B2 | 7/2011 | Smisson, III et al. | |
| 8,133,203 B2 | 3/2012 | Hack | |
| 8,387,963 B2 | 3/2013 | Moutafis | |
| 8,425,486 B2 | 4/2013 | Smisson et al. | |
| 8,574,200 B2 | 11/2013 | Hack | |
| 8,690,842 B2 | 4/2014 | Lopez | |
| 8,803,044 B2 | 8/2014 | Kienman et al. | |
| 9,057,363 B2 | 6/2015 | Capone et al. | |
| 9,107,986 B2 | 8/2015 | Bonnette et al. | |
| 9,192,711 B2 | 11/2015 | Barnes | |
| 9,220,835 B2 | 12/2015 | Cane' | |
| 9,267,498 B2 | 2/2016 | Kolln | |
| 9,295,778 B2 | 3/2016 | Kamen et al. | |
| 9,362,740 B1 * | 6/2016 | Elnar | F24H 15/414 |
| D794,780 S | 8/2017 | Damgård | |
| 9,717,862 B2 | 8/2017 | Krogh Andersen | |
| 10,004,846 B2 | 6/2018 | Bonnette et al. | |
| 10,016,564 B2 | 7/2018 | Piehl et al. | |
| 10,137,257 B2 | 11/2018 | Landy, III et al. | |
| 10,322,227 B2 | 6/2019 | Piehl et al. | |
| 10,391,257 B2 | 8/2019 | Piehl et al. | |
| 10,485,936 B2 | 11/2019 | Landy, III et al. | |
| 10,661,029 B2 | 5/2020 | Robertson et al. | |
| 10,888,671 B2 | 1/2021 | Andersen | |
| 11,013,857 B2 | 5/2021 | Uber, III et al. | |
| 11,330,676 B2 * | 5/2022 | Everly | B01D 53/944 |
| 11,383,052 B2 * | 7/2022 | Buchberger | A24F 40/46 |
| 11,458,256 B2 | 10/2022 | Piehl et al. | |
| 11,744,936 B2 | 9/2023 | Lane et al. | |
| 11,957,886 B2 | 4/2024 | Piehl et al. | |
| 12,465,678 B2 | 11/2025 | Lane et al. | |
| 2004/0229479 A1 * | 11/2004 | Carr | H05B 3/36 |
| | | | 439/37 |
| 2005/0276586 A1 * | 12/2005 | Thweatt | A47L 11/4086 |
| | | | 392/488 |
| 2007/0051409 A1 | 3/2007 | Landy et al. | |
| 2007/0142773 A1 | 6/2007 | Rosiello et al. | |
| 2008/0281268 A1 | 11/2008 | Vest Hansen | |
| 2010/0296800 A1 | 11/2010 | Min et al. | |
| 2010/0310241 A1 * | 12/2010 | Hollis | F24H 1/142 |
| | | | 392/488 |
| 2011/0202034 A1 | 8/2011 | Lopez | |
| 2012/0330234 A1 * | 12/2012 | Balluff | A61M 5/44 |
| | | | 604/114 |
| 2013/0255670 A1 | 10/2013 | Ott et al. | |
| 2014/0167502 A1 | 6/2014 | Lopez | |
| 2014/0171905 A1 | 6/2014 | Lopez | |
| 2014/0309612 A1 | 10/2014 | Smisson, III et al. | |
| 2016/0101228 A1 | 4/2016 | Landy, III et al. | |
| 2017/0021951 A1 | 1/2017 | Teague | |
| 2017/0273146 A1 | 9/2017 | Everly et al. | |
| 2018/0236180 A1 | 8/2018 | Andersen | |
| 2018/0243531 A1 | 8/2018 | Guo et al. | |
| 2018/0296752 A1 | 10/2018 | Bonnette et al. | |
| 2018/0353678 A1 | 12/2018 | Adams et al. | |
| 2019/0336725 A1 | 11/2019 | Pettini et al. | |
| 2020/0016317 A1 | 1/2020 | Kelly et al. | |
| 2020/0061273 A1 | 2/2020 | Hogard et al. | |
| 2020/0230304 A1 | 7/2020 | Field et al. | |
| 2021/0045913 A1 | 2/2021 | Landy, III et al. | |
| 2022/0355094 A1 | 11/2022 | Landy, III et al. | |
| 2025/0195787 A1 | 6/2025 | Lane et al. | |

FOREIGN PATENT DOCUMENTS

| | | |
|---|---|---|
| JP | 2005168958 A | 6/2005 |
| WO | WO-0162194 A1 | 8/2001 |
| WO | WO-2016145211 A1 | 9/2016 |
| WO | WO-2022192285 A1 | 9/2022 |

OTHER PUBLICATIONS

International Search Report and Written Opinion for International Application No. PCT/US2023/067515 dated Nov. 6, 2023, 18 pages.

EP Application No. 23812791.4, Supplementary European Search Report and Search Opinion dated Apr. 20, 2026; Applicant 410 Medical, Inc.; 11 pages.

* cited by examiner

1020

1120

1220

2520A

2520B

2520C

1920

1921

SYSTEMS, APPARATUS, AND METHODS FOR WARMING FLUID FOR INTRAVENOUS INFUSION

CROSS-REFERENCE TO RELATED APPLICATIONS

This application is a continuation of U.S. patent application Ser. No. 18/959,439 entitled "Systems, Apparatus, and Methods for Warming Fluid for Intravenous Infusion," filed Nov. 25, 2024, which is a continuation of International Patent Application No. PCT/US2023/067515 entitled "Systems, Apparatus, and Methods for Warming Fluid for Intravenous Infusion," filed on May 25, 2023, which claims priority to and the benefit of U.S. Provisional Patent Application Ser. No. 63/345,844 entitled "Systems, Apparatus, and Methods for Warming Fluid for Intravenous Infusion," filed on May 25, 2022, the entire contents of each of which are incorporated by reference herein for all purposes.

STATEMENT REGARDING RESEARCH AND DEVELOPMENT

This invention was made with government support under Contract No. FA864922PO648 awarded by AFWERX (United States Air Force Research Laboratory (AFRL)). The government has certain rights in the invention.

BACKGROUND

Many medical conditions require the delivery of intravenous fluids and/or blood products, and some conditions, such as hemorrhagic shock, require rapid delivery of the fluids and blood products. Rapid infusers are typically bulky and complex to set up and use. Additionally, rapid infusers are typically limited in the amount of pressure they can generate (e.g., to 300 mmHg) due to the types of mechanisms they use to generate pressure (external pressurization of the intravenous (IV) bag, peristaltic pump). While they may be able to deliver fluids and blood quickly through large-bore IV access (upwards of 1000 mL/min), typical rapid infusers have limited flow rates through peripheral IVs. Additionally, warming intravenous fluid and/or blood products prior to administration to a patient has numerous benefits, including improved recovery time, prevention of hypothermia, and increased patient comfort.

Therefore, there is a need for systems, apparatus, and methods for fluid infusion that allow for easy transportation, simple set up and user control, continuous fluid flow at high flow rates through peripheral IV sites, and fluid warming. Specifically, there is a need for systems, apparatus, and methods for intravenous fluid warming that is energy efficient, consistent, and effective at high fluid flow rates, while also being portable and allowing for quick and simple set up.

SUMMARY

In some embodiments, a system includes a housing, an elongated heating element, a first electrical connector, and a second electrical connector. The housing can include one or more channel walls defining a fluid channel extending from a fluid inlet to a fluid outlet. The elongated heating element can be disposed entirely within the fluid channel. The elongated heating element can have an outer surface (e.g., an entirety of the outer surface of the heating element) spaced from each of the one or more channel walls such that fluid within the fluid channel can flow between the one or more channel walls and the outer surface of the elongated heating element. The first electrical connector can be electrically coupled to a first portion of the elongated heating element and the second electrical connector can be electrically coupled to a second portion of the elongated heating element. Each of the first electrical connector and the second electrical connector configured to be electrically coupled to a power source such that energy can be provided from the power source to the elongated heating element via one of the first electrical connector or the second electrical connector to increase the temperature of the elongated heating element.

DETAILED DESCRIPTION

Figure 1:
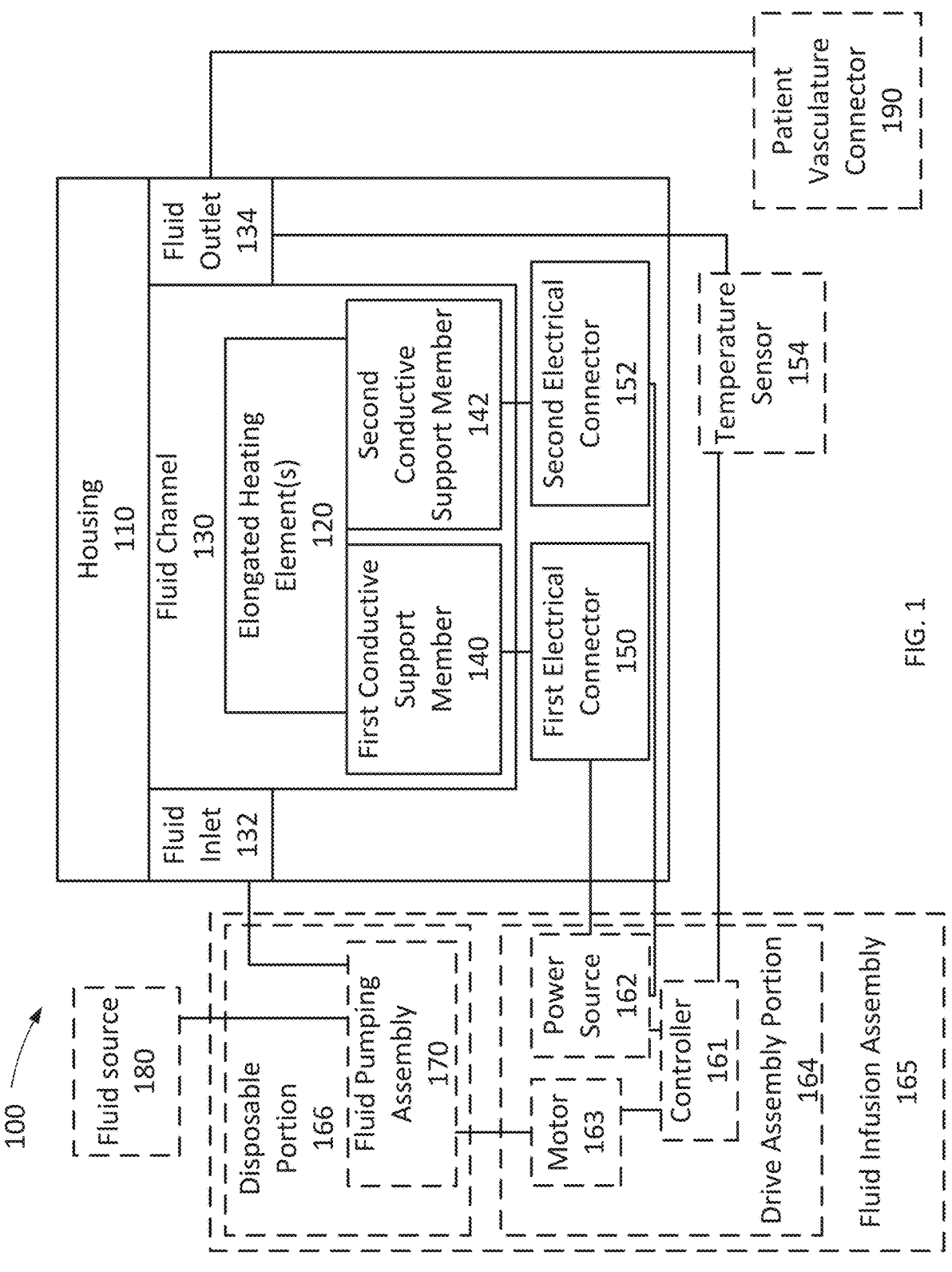
FIG. 1 is a schematic illustration of a fluid warmer system, according to an embodiment.

In some embodiments, a system includes a housing, an elongated heating element, a first electrical connector, and a second electrical connector. The housing can include one or more channel walls defining a fluid channel extending from a fluid inlet to a fluid outlet. The elongated heating element can be disposed entirely within the fluid channel. The elongated heating element can have an outer surface (e.g., an entirety of the outer surface of the heating element) spaced from each of the one or more channel walls such that fluid within the fluid channel can flow between the one or more channel walls and the outer surface of the elongated heating element. The first electrical connector can be electrically coupled to a first portion of the elongated heating element and the second electrical connector can be electrically coupled to a second portion of the elongated heating element. Each of the first electrical connector and the second electrical connector configured to be electrically coupled to a power source such that energy can be provided from the power source to the elongated heating element via one of the first electrical connector or the second electrical connector to increase the temperature of the elongated heating element.

In some embodiments, a system includes a housing, an elongated heating element, a first electrical connector, and a second electrical connector. The housing can define a fluid inlet, a fluid outlet, and a fluid channel extending from the fluid inlet to the fluid outlet. The elongated heating element can be disposed entirely within the fluid channel. The elongated heating element can include a first surface disposed in a first plane and second surface disposed in a second plane parallel to the first plane. The first electrical connector can be partially disposed within the fluid channel and can be coupled to a first portion of the elongated heating element. The second electrical connector can be partially disposed within the fluid channel and coupled to a second portion of the elongated heating element. The first electrical connector can be configured to support the first portion of the elongated heating element within the fluid channel and the second electrical connector can be configured to support the second portion of the elongated heating element within the fluid channel such that fluid can flow along the first side surface and the second side surface of the elongated heating element. Each of the first electrical connector and the second electrical connector configured to be electrically coupled to a power source such that energy can be provided from the power source to the elongated heating element via one of the first electrical connector or the second electrical connector to increase the temperature of the elongated heating element.

In some embodiments, a system includes a housing, an elongated heating element, a first conductive support member, a second conductive support member, a first electrical connector, and a second electrical connector. The housing can define a fluid inlet, a fluid outlet, and a fluid channel extending from the fluid inlet to the fluid outlet. The elongated heating element can disposed within the fluid channel. The first conductive support member can be coupled to the elongated heating element at a first location.

The second conductive support member can be coupled to the elongated heating element at a second location. The first conductive support member and the second conductive support member can be configured to support the elongated heating element within the fluid channel such that fluid can flow between a channel wall of the housing defining the fluid channel and the elongated heating element along two opposing side portions of the elongated heating element. The first electrical connector can be electrically coupled to the first conductive support member and the second electrical connector can be electrically coupled to the second conductive support member. Each of the first electrical connector and the second electrical connector can be configured to be electrically coupled to a power source such that energy can be provided from the power source to the elongated heating element via one of the first electrical connector or the second electrical connector to increase the temperature of the elongated heating element.

In some embodiments, a system includes a housing, an elongated heating element, a first conductive support member, a second conductive support member, a first electrical connector, and a second electrical connector. The housing can define a fluid inlet, a fluid outlet, and a fluid channel extending from the fluid inlet to the fluid outlet. The elongated heating element can have a first side surface, a second side surface, an upper surface, and a lower surface. The elongated heating element can disposed entirely within the fluid channel. The first conductive support member can be at least partially disposed within the fluid channel and coupled to the elongated heating element at a first location. The second conductive support member can be at least partially disposed within the fluid channel and coupled to the elongated heating element at a second location. The first electrical connector can be electrically coupled to the first conductive support member and the second electrical connector can be electrically coupled to the second conductive support member. Each of the first electrical connector and the second electrical connector can be configured to be electrically coupled to a power source such that energy can be provided from the power source to the elongated heating element via one of the first electrical connector or the second electrical connector to increase the temperature of the elongated heating element.

FIG. 1 is a schematic illustration of a system 100 (also referred to as a fluid warmer system, a fluid warmer or a warm fluid infuser). The system 100 includes a housing 110, an elongated heating element 120, a first conductive support member 140, a second conductive support member 142, a first electrical connector 150, and a second electrical connector 152. The housing 110 defines a fluid inlet 132, a fluid outlet 134, and a fluid channel 130 (also referred to as a "pathway") extending from the fluid inlet 132 to the fluid outlet 134. The elongated heating element 120 is disposed within the fluid channel 130.

The fluid channel 130 can have any suitable shape. For example, the fluid channel 130 can include any suitable number of straight segments and/or curved segments having any suitable radius of curvature. Thus, in some embodiments, the fluid channel 130 can be straight such that the fluid inlet 132, the fluid channel 130, and the fluid outlet 134 are coaxially aligned. In some embodiments, the fluid channel 130 can have a serpentine shape including any suitable number of curved segments coupled directly to adjacent curved segments or coupled to adjacent curved segments via straight segments. In some embodiments, some or all of the straight segments of a fluid channel 130 can be disposed parallel to one another and coupled in series by curved segments. The fluid channel 130 can be shaped such that an overall length, width, and/or height of the housing 110 can be reduced due to the fluid channel 130 making multiple passes back and forth within one or more planes rather than extending straight a distance from the fluid inlet 132 to the fluid outlet 134). In some embodiments, the fluid channel 130 can include a spiral shape. As described in more detail, the length of the fluid channel 130 from the fluid inlet 132 and the fluid outlet 134 can be sufficiently long such that, in combination with the cross-sectional area of the fluid channel 130, the elongated heating element 120 disposed within the fluid channel 130 can have a target electrical resistance and have a sufficiently large surface area in contact with the fluid flow to warm fluid passing through the fluid channel 130 to a target temperature or a target temperature range.

The fluid channel 130 can have any suitable cross-sectional shape. For example, the cross-sectional shape of the fluid channel 130 defined by the channel wall(s) of the housing 110 can be round, ovular, circular, rectangular, polygonal (e.g., hexagonal), or any other suitable shape. In some embodiments, any corners of the fluid channel 130 can be rounded or curved. For example, in some embodiments in which the fluid channel 130 has a rectangular cross-sectional shape, the housing 110 can include fillets along the fluid channel 130 to round the corners of the rectangle.

The size (e.g., cross-sectional area) of the fluid channel 130 can be selected to appropriately manage particulate and to minimize turbulent flow. Specifically, the system 100 can be used to warm fluid including blood or blood products for delivery to a patient's vasculature. Transfused blood can include particulate (e.g., small clots) that may not be filtered prior to traveling into the fluid channel 130. If the fluid channel 130 is too narrow (e.g., overall, or in spaces in the fluid channel 130 defined between the elongated heating element 120 and the channel wall of the housing 110), particulate could become lodged within the fluid channel 130. Additionally, the narrower the fluid channel 130, the higher the Reynolds number (i.e., the degree to which a fluid flow is turbulent versus laminar) becomes. Reynolds numbers of 2000 to 4000 can result in varying levels of turbulent flow, with fully turbulent flow occurring at Reynolds numbers above 4000. If the fluid flow through the fluid channel 130 is excessively turbulent, the turbulence can impart high shear forces on the fluid which can cause hemolysis of red blood cells. To minimize the potential for clogging the warmer with particular and to avoid imparting excessive shear forces on blood due to highly turbulent flow associated with a high Reynolds number, the fluid channel 130 can be formed such that no dimension (e.g., diameter or other lateral extent) of any cross-sectional area of the fluid channel 130 between the first end and the second end is below a minimum distance. The minimum distance can be, for example, 0.050".

The size (e.g., cross-sectional area) of the fluid channel 130 can also be selected such that the fluid channel 130 can be fully primed such that liquid fluid displaces air within the fluid channel 130 regardless of the orientation of the fluid channel 130 relative to gravity. Such a feature prevents trapped air from being disposed within the fluid channel 130 and reduces the risk of user error since it does not require that the device be held in a specific orientation during priming. Such a feature can be achieved by forming the fluid channel 130 such that all cross-sectional areas of the fluid channel 130 between the first end to the second end of the fluid channel 130 have a sufficiently small maximum diameter or lateral extent. In some embodiments, the maximum diameter can be, for example, about 0.500" or about 0.375".

In some embodiments, the housing 110 includes two portions that can be coupled together to define the fluid channel 130. The first portion can be, for example, a clamshell defining the fluid channel 130 (e.g., three sides of fluid channel 130 having a rectangular cross-section), and the second portion can be a lid or cap that can be attached to the first portion and form at least one boundary (e.g., a top surface) of the fluid channel 130. In some embodiments, the first portion can define, for example, a lower half of the fluid channel 130, and the second portion can be define, for example, an upper half of the fluid channel 130. The first portion and the second portion can be coupled together via a seal such that fluid is prevented from leaking from the fluid channel 130. In some embodiments, the seal can include ultrasonic welding, solvent bonding, radio-frequency (RF) welding, adhesives, and/or one or more gaskets in combination with fasteners. The fluid channel 130 is sealed both around the perimeter of the housing 110 and between consecutive passes of the elongated heating element 120 such that all liquid fluid and air that enters the fluid inlet 132 follows the elongated heating element 120 to the fluid outlet 134, such that the housing 110 is reinforced such that the first portion and second portion resist separating due to positive and negative fluid pressures within the fluid pathway 130, and such that air is prevented from leaking into the fluid channel 130. In some embodiments, the interface between the first portion and the second portion of the housing 110 along each side of the fluid channel 130 includes a seal extending along the length of the fluid channel 130 (e.g., continuously and parallel to a central axis of the fluid channel 130). In some embodiments, the housing 110 is formed such that the outer surface of the housing 110 is shaped as a block having six sides.

In some embodiments the fluid inlet 132 and the fluid outlet 134 are disposed on the same side of the housing 110. In some embodiments, the fluid inlet 132 and the fluid outlet 134 are disposed on different sides of the housing (e.g., opposite sides). In some embodiments, the housing 110 can have an outer surface that conforms or corresponds to the shape of the fluid channel 130 (e.g., serpentine, U-shaped). In some embodiments, the housing 110 can include straight and curved segments, and the straight segments can be disposed in parallel with one another and either be contacting or spaced from adjacent parallel segments. In some embodiments, the housing 110 can include a central portion that includes a number of straight channel segments in one or more planes, and end caps configured to be sealingly coupled to opposite ends of the central portion and defining a number of curved channel segments configured to fluidically couple a straight channel segment to another straight channel segment with a 180 degree curve to form a serpentine flow path. In some embodiments, the housing 110 can be formed as or included in a cartridge that can be coupled with other systems or assemblies, such as a drive assembly portion 164 of an fluid infusion assembly 165, and can include mechanical and/or electrical interfaces. In some embodiments, the housing 110 can include protruding features such as ridges, ribs, protrusions, and/or other structures extending from a channel wall defining the fluid channel 130 and configured to support the elongated heating element 120 within the fluid channel 130.

Figure 17:
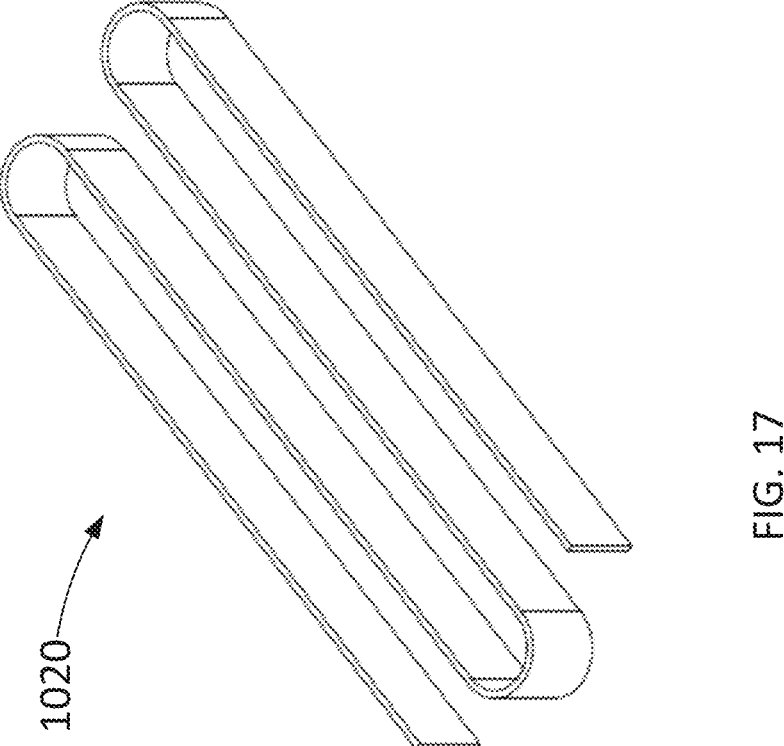
FIG. 17 is a perspective view of an elongated heating element, according to an embodiment.
Figure 18:
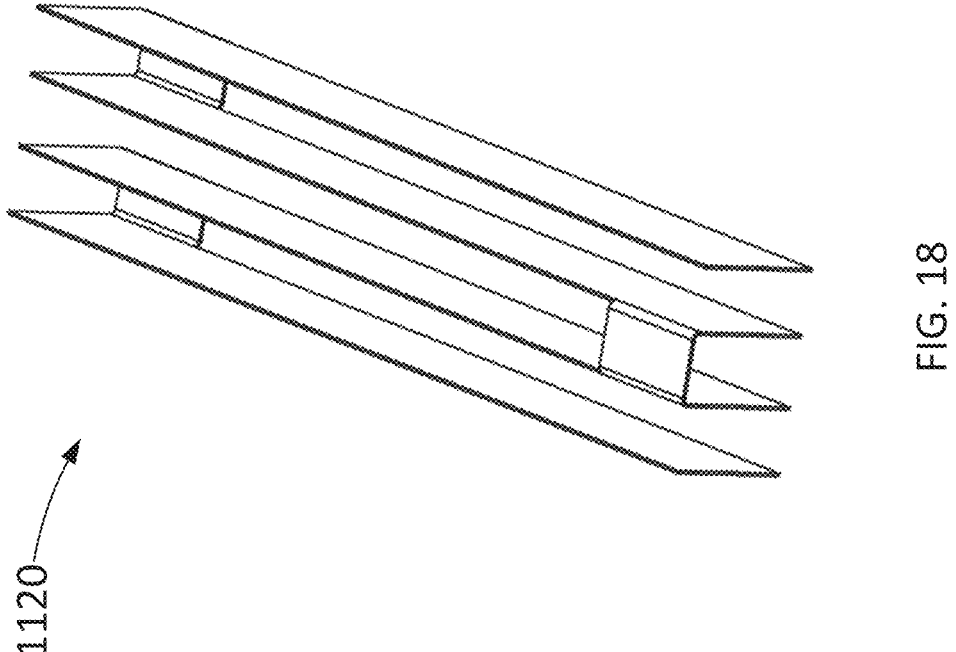
FIG. 18 is a perspective view of an elongated heating element, according to an embodiment.
Figure 19:
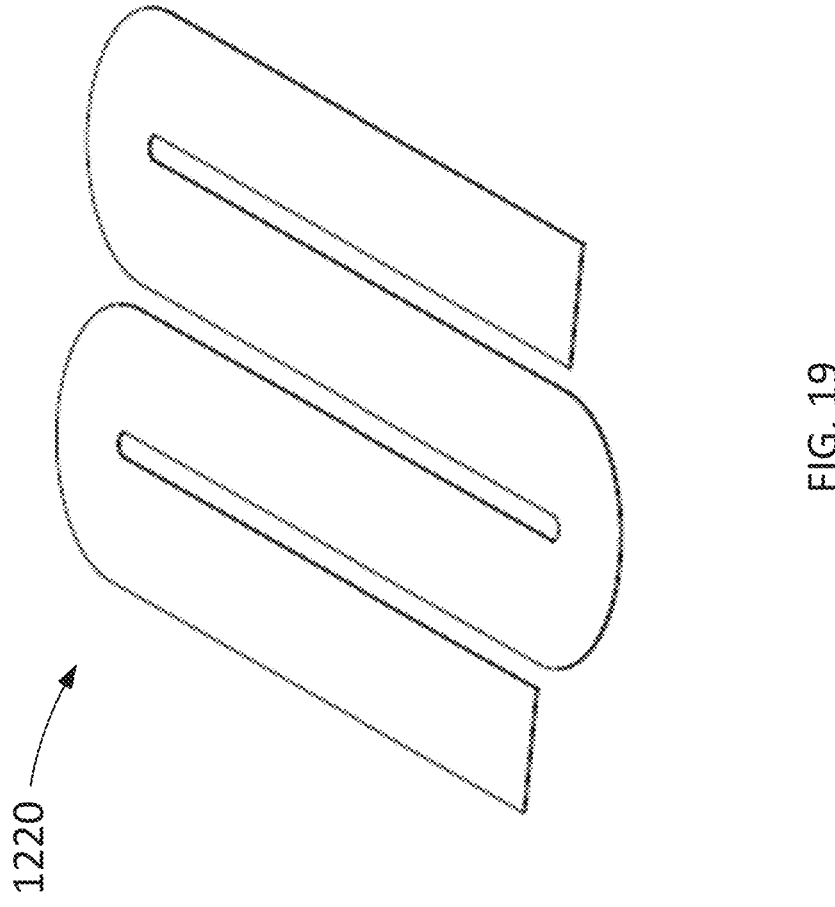
FIG. 19 is a perspective view of an elongated heating element, according to an embodiment.

The elongated heating element 120 (also referred to as an elongated heating member, a heating element, or a heating member) can have an overall shape corresponding to a shape of the fluid channel 130 or a portion of the fluid channel 130. For example, the elongated heating element 120 can extend between a location at or near a first end of the fluid channel 130 (e.g., at or near the fluid inlet 132) and a location at or near a second end of the fluid channel 130 (e.g., at or near the fluid outlet 134). In some embodiments, the elongated heating element 120 can be ribbon-shaped, like, for example, the elongated heating element 1020 shown in FIG. 17, which is a ribbon of metal folded into the desired shape or formed in the desired shape. In some embodiments, the elongated heating element 120 can be stamped out of sheet stock metal such that parallel elongated portions are coupled to adjacent elongated portions by perpendicularly-disposed flat segments, as shown, for example, in FIG. 18 with respect to the elongated heating element 1120. In some embodiments, the elongated heating element 120 can be planar and formed as a flat ribbon and, for example, stamped out of sheet stock, similar to the elongated heating element 1220 shown in FIG. 19. In some embodiments, the elongated heating element 120 can be formed as a wire, such as a round wire or a hollow round wire. For example, a hollow round wire can have a larger diameter than a non-hollow round wire (and thus, increased cross-sectional area and increased contact between the outer surface of the hollow round wire and fluid), while having the same resistance as the non-hollow round wire having the smaller diameter. The elongated heating element 120 can be sufficiently rigid such that shape of the elongated heating element 120 and the location of the elongated heating element 120 relative to the housing 110 (e.g., relative to the channel walls of the housing 110 defining the fluid channel 130) is maintained regardless of the orientation of the system 100 (e.g., regardless of whether the housing 110 is turned upside-down or on its side with the elongated heating element 120 mounted therein). In some embodiments, the elongated heating element 120 can be disposed within the fluid channel 130 such that the distance between the side surfaces of the elongated heating element 120 and the channel wall each side surface faces are constant throughout the entire length of the elongated heating element 120 and/or throughout the length of the straight portions of the elongated heating element 120. In some embodiments, the elongated heating element 120 can be disposed within the fluid channel 130 such that the distance between the opposing side surfaces of the elongated heating element 120 and the channel wall each opposing side surface faces are equal.

The elongated heating element 120 has a first side surface, a second side surface, an upper surface, and a lower surface. In some embodiments, the elongated heating element 120 has a width between the first side surface and the second side surface smaller than a height of the elongated heating element 120 between the upper surface and the lower surface. Thus, the elongated heating element 120 can extend in the fluid channel 130 away from the first electrical connector 150 in a direction parallel to or coaxial with a central axis of the first electrical connector 150 or the second electrical connector 152. In some embodiments, the elongated heating element 120 has a width between the first side surface and the second side surface larger than a height of the elongated heating element 120 between the upper surface and the lower surface. Thus, the elongated heating element 120 can extend in the fluid channel 130 away from the first electrical connector 150 in a direction perpendicular to a central axis of the first electrical connector 150 or the second electrical connector 152. The fluid channel 130 and the elongated heating element 120 can be shaped and sized such that fluid flowing through the fluid channel 130 flows along the length of the elongated heating element 120.

The elongated heating element 120 can be a resistive heating element (also referred to as a "heat exchanger"). In some embodiments, the elongated heating element 120 can convert electrical energy into heat energy that is transferred from the elongated heating element 120 to fluid in the fluid channel 130 to increase the temperature of the fluid in the fluid channel 130. In some embodiments, the elongated heating element 120 can convert electrical energy into heat energy such that fluid traveling through the fluid channel 130 at high flow rates (e.g., between the keep vein open (KVO) rate and about 1500 mL/min or between about 10 mL/min and about 1500 mL/min) can be warmed (e.g., from a storage temperature such as 2-6° C. or from room temperature to or near a target temperature such as body temperature). In some embodiments, the elongated heating element 120 can be formed to have sufficient surface area and a target electrical resistance (e.g., an electrical resistance of about 1Ω) so that sufficient heat can be transferred to the fluid traveling through the fluid channel 130 at a particular flow rate (e.g., a high flow rate). The target electrical resistance can be selected such that the current required to generate the desired power for heating is not excessively high, which may be the case if the resistance is too low, and so that the current provided by the power supply is not insufficient to generate the desired power for heating, which may be the case if the resistance is too high. For example, in some embodiments, the electrical resistance of the elongated heating element 120 can be between about 0.1Ω and about 10Ω. In some embodiments, the elongated heating element 120 can be formed as a flat ribbon having a thickness no smaller than about 0.001" to avoid manufacturing difficulties and accidental breakage, and a thickness no greater than about 0.030" to avoid difficulty in folding the flat ribbon during assembly and to avoid the need for the elongated heating element 120 to be unnecessarily large and unwieldy, since increasing the thickness would require the height to decrease or the length to increase to maintain the same resistance. In some embodiments, the height of the flat ribbon elongated heating element 120 can be no greater than about 0.500" to avoid exceeding the maximum fluid channel height that allows for proper priming (e.g., 0.500"). In some embodiments, the length of the elongated heating element 120 (e.g., formed as a flat ribbon) can be no more than 150" to avoid an excessively sized heating element 120 and an excessively sized housing 110 having a large priming volume. The length of the elongated heating element 120 (e.g., formed as a flat ribbon) can be no less than 12" to avoid insufficient resistance, insufficient surface area, and electrolysis due to an excessive potential drop in a short distance. In some embodiments, the elongated heating element 120 can have a cross-sectional area that varies to create localized areas of more or less heating by decreasing or increasing the cross-sectional area, respectively. For example, the cross-sectional area may be increased in areas where the heating element 120 contacts the warmer housing 110 to minimize warming in those areas. In some embodiments, the elongated heating element 120 has a constant cross-sectional area from a first end to a second end of the elongated heating element, or through portions of the elongated heating element 120, such as through all straight segments of a serpentine-shaped elongated heating element 120. The heating element 120 can be formed of any suitable metal, such as, for example, stainless steel, titanium, and/or copper alloys. In some embodiments, a coating (e.g., a thin coating) or an electrically insulative layer can be disposed on the heating element 120. For example, the heating element 120 can be coated with a parylene coating, a silicone conformal coating, Kapton® polyimide film, and/or any other suitable coating.

In some embodiments, the cross-sectional area of the fluid channel 130 through which fluid can flow can be substantially constant along the length of the fluid channel 130 and/or along the length of the fluid channel within which the elongated heating element is disposed. For example, in some embodiments, one or more channel walls of the housing 110 can define one or more increased width portions of the fluid channel 130 associated with components disposed within the fluid channel and obstructing fluid flow such that the cross-sectional area of the fluid channel 130 through which fluid can is substantially constant along the length of the elongated heating element 120 even in portions in which the first electrical connector 150, the second electrical connector 152, the first conductive support member 140, the second conductive support member 142, and/or any protruding members configured to support and retain portions of the heating element 120 protrude into the fluid channel 130 from the one or more channel walls of the housing 110. For example, the one or more channel walls can define a first increased width portion of the fluid channel associated with the first electrical connector 150 and/or the first conductive support member 140 and a second increased width portion of the fluid channel associated with the second electrical connector 152 and/or the second conductive support member 142. In some embodiments, the one or more channel walls can define one or more portions of the fluid channel 130 having increased height and/or width. In some embodiments, the elongated heating element can include portions of increased height and/or width which can correspond to the increased height and/or width portions of the fluid channel 130 defined be the one or more channel walls of the housing 110 and/or can cause the surface area of the elongated heating element 120 accessible for contact with fluid within the fluid channel 130 to be substantially constant along the length of the elongated heating element 120, even with respect to portions of the elongated heating element 120 that may define openings and/or be partially covered or contacted by other components.

In some embodiments, the heating element 120 can be shaped and sized to avoid excessively high DC voltage (e.g., 60+ V), which may be hazardous to a patient and/or a clinical provider and may be more likely to exhibit undesirable effects such as electrolysis in the fluid channel 130. In some embodiments, the heating element 120 can be shaped and sized to avoid excessively high DC current (e.g., 60+ A), which requires prohibitively large electrical connectors in the power source 162. In some embodiments, using the system 100 to warm fluid from 4 C to 38 C at 1500 mL/min requires approximately 3000 W of power. Targeting a resistance for the heating element 120 of about 1Ω allows for 3000 W to be produced with a voltage of approximately 55 A and a current of approximately 55V, keeping both current and voltage in a reasonable range for patient and clinical provider safety and for portability.

The first conductive support member 140 is coupled to the elongated heating element 120 at a first location (e.g., at or near a first end of the elongated heating element 120) and the second conductive support member 142 is coupled to the elongated heating element 120 at a second location (e.g., at or near a second end of the elongated heating element 120). The first conductive support member 140 and the second conductive support member 142 are configured to support the elongated heating element 120 such that the elongated heating element 120 is disposed within the fluid channel 130 (e.g., entirely disposed within the fluid channel 130). The first conductive support member 140 and the second conductive support member 142 can support the elongated heating element 120 such that fluid can flow between a channel wall of the housing 110 defining the fluid channel 130 and the elongated heating element 120 along two opposing side portions of the elongated heating element 120, contacting the opposing side portions. For example, the first conductive support member 140 and the second conductive support member 142 are configured to support the elongated heating element 120 such that the elongated heating element 120 is disposed within the fluid channel 130 such that at least three surfaces of the first side surface, the second side surface, the upper surface, and the lower surface of the elongated heating element 120 are spaced from a channel wall of the housing 110 defining the fluid channel 130 and fluid can flow between the channel wall and each of the at least three surfaces, contacting each of the at least three surfaces. In some embodiments, the first conductive support member 140 and the second conductive support member 142 are configured to support the elongated heating element 120 within the fluid channel 130 such that a space is defined for fluid flow between each of the first side surface, the second side surface, the upper surface, and the lower surface and the channel wall of the housing 110 defining the fluid channel 130 and fluid flowing through the channel 130 can contact each of the first side surface, the second side surface, the upper surface, and the lower surface. In some embodiments, the elongated heating element 120 can have any suitable cross-sectional shape (e.g., round, ovular, rectangular, square, triangular), and the first conductive support member 140 and the second conductive support member 142 can support the elongated heating element 120 such that spaces for fluid flow are defined between the elongate heating element 120 and the channel wall portions at least on opposing sides of the elongate heating element 120, and may fully surround the elongated heating element 120 along the length of the elongated heating element 120. In some embodiments, the entire elongated heating element 120 is disposed within the fluid channel 130 (e.g., from a first end to a second end of the elongated heating element 120). In some embodiments, no portion of the elongated heating element 120 directly contacts any portion of the housing 110 (e.g., any portion of the channel wall of the housing 110 defining the fluid channel 130).

In some embodiments, the first conductive support member 140 and/or the second conductive support member 142 can be at least partially disposed within the fluid channel 130 such that fluid flowing through the fluid channel 130 can contact the first conductive support member 140 and the second conductive support member 142. In some embodiments, the shape and/or size of the fluid channel 130 in the portions of the fluid channel 130 in which the first conductive support member 140 and the second conductive support member 142 contact the heating element 120 can be the same as the portions of the fluid channel 130 within which portions of the heating element 120 between the contact locations are disposed (e.g., the entire fluid channel between the contact locations with the heating element 120 or the portions of the fluid channel containing the straight portions of the heating element 120 between the contact locations). In some embodiments, the fluid channel 130 can have a larger cross-sectional area (e.g., can be wider) in the portion of the fluid channel 130 within which the first conductive support member 140 and the second conductive support member 142 contact the heating element 120 than in remaining portions of the fluid channel 130 within which the heating element 120 is disposed, but the fluid channel 130 can still be self-priming when fluid is introduced into the fluid channel 130 (e.g., due to the shape and size of the fluid channel 130 relative to the heating element 120 and the first and second conductive support members 140, 142). In some embodiments, the interface between each of the first conductive support member 140 and/or the second conductive support member 142 and the elongated heating element 120 can be disposed within the fluid channel 130. Disposing the first conductive support member 140 and the second conductive support member 142 within the fluid channel 130 can allow for high rates of warming within the fluid channel 130 and reduced warming outside of the fluid channel 130 (e.g., of the housing defining the fluid channel 130), maximizing efficiency and minimizing hazards to patients and/or clinical providers. Additionally, fluid can flow around the first conductive support member 140 and the second conductive support member 142 in the fluid channel 130 such that resistance to fluid flow through the channel and shear forces that are potentially-damaging to blood are both minimized. In some embodiments, the first conductive support member 140 and/or the second conductive support member 142 can be disposed at least partially within the fluid channel 130 and coupled to the elongated heating element 120 within the fluid channel 130 such that the elongated heating element 120 in combination with the first conductive support member 140 and/or the second conductive support member 142 "split" the fluid channel 130 into two separate, parallel fluid channels disposed on opposite sides of the elongated heating element 120 (e.g., due to the elongated heating element 120, the first conductive support member 140 and/or the second conductive support member 142 extending at least from a first portion of a channel wall to a second portion of the channel wall to define smaller distinct fluid channels within the fluid channel 130 on opposite sides of the elongated heating element 120). Each of the smaller fluid channels defined through the fluid channel 130 can be self-priming.

In some embodiments, the first conductive support member 140 and the second conductive support member 142 can have a relatively low electrical resistance compared to the elongated heating element 120, and therefore generate minimal heat. The low relative resistance of each of the first conductive support member 140 and the second conductive support member 142 can be achieved by forming the first conductive support member 140 and the second conductive support member 142 such that each has a sufficiently large effective cross-sectional area through which electrical current can travel relative to the elongated heating element 120. The cross-sectional area of each of the first conductive support member 140 and the second conductive support member 142 can be sufficiently large, for example, such that each can effectively function as a low gauge wire (e.g., having a lower gauge equivalency than the elongated heating element 120). In some embodiments, the first conductive support member 140 and the second conductive support member 142 can be formed of a material that is less resistive than the material forming the elongated heating element 120 such that resistance of the first conductive support member 140 and the second conductive support member 142 are reduced or further reduced compared to the elongated heating element 120. Cross-sectional area of a metal element is inversely related with current density and resistance, and thus reduced cross-sectional area is associated with increased heat generation. For this reason, it is desired to increase the cross-sectional area of conductive elements outside of the fluid channel to reduce or eliminate hot spots that may damage the housing 110 (e.g., plastic components of the housing 110) and may cause safety concerns.

The first electrical connector 150 can be electrically coupled to the first conductive support member 140 and the second electrical connector 152 can be electrically coupled to the second conductive support member 142. In some embodiments, the first electrical connector 150 can directly contact the first conductive support member 140 and the second electrical connector 152 can directly contact the second conductive support member 142. In some embodiments, the interface between each of the first electrical connector 150 and the first conductive support member 140 and the second electrical connector 152 and the second conductive support member 142 can be disposed within the fluid channel 130 and fluid flowing through the fluid channel 130 can contact a portion of each of the first electrical connector 150 and the second electrical connector 152. The first electrical connector 150 and the second electrical connector 152 can extend through a wall of the housing 110 such that each be electrically coupled (e.g., releasably) to a power source 162 such that energy can be provided from the power source 162 to the elongated heating element(s) 120 via one of the first electrical connector 150 and the first conductive support member 140 or the second electrical connector 152 and the second conductive support member 142 to increase the temperature of the elongated heating element(s) 120.

In some embodiments, the first electrical connector 150 and the second electrical connector 152 can extend through a sidewall of the housing 110 into the fluid channel 130 such that a central axis of each of the first electrical connector 150 and the second electrical connector 152 is disposed perpendicular to the direction of flow of fluid through the fluid channel 130. In some embodiments, the first electrical connector 150 and the second electrical connector 152 can have a large diameter such that each of the first electrical connector 150 and the second electrical connector 152 have a lower gauge equivalency than the first conductive support member 140, the second conductive support member 142, and the elongated heating element 120. The first electrical connector 150 and the second electrical connector 152 can each be formed as a plug (e.g., a male plug) having a portion that projects beyond an outer surface of the housing 110 for engagement with the power source 162 (e.g., with a female electrical connector associated with the power source 162). Additionally, in some embodiments, the first electrical connector 150 and the second electrical connector 152 can each have a top surface forming a portion of the wall defining the fluid channel 130. In some embodiments, a portion of each of the first electrical connector 150 and the second electrical connector 152 can extend into the fluid channel 130 such that fluid can contact sidewalls of the first electrical connector 150 and the second electrical connector 152.

In some embodiments, the first conductive support member 140 and the second conductive support member 142 can each include a first portion formed as a screw and a second portion formed as a metal clip (e.g., a leaf spring) disposed entirely within the fluid channel 130 and configured to engage with and support the heating element 120. The cross-sectional thickness of the metal portions forming each clip can all be smaller than the cross-sectional thickness (e.g., diameter) of the screw and the cross-sectional thickness (e.g., diameter) of the first electrical connector 150 and the second electrical connector 152. Thus, the portions of the system 100 disposed within the fluid channel 130 and contacting fluid will generate higher amounts of heat than the first electrical connector 150 and the second electrical connector 152 due to their relative shapes and sizes (e.g., thicknesses). Additionally, the interface between the first portion and the second portion can be disposed entirely within the fluid channel 130 such that fluid traveling through the fluid channel 130 can contact both the first portion and the second portion, with the second portion disposed entirely within the fluid channel 130 and the first portion disposed at least partially within the fluid channel 130.

In some embodiments, the first electrical connector 150 and the second electrical connector 152 can include a top surface and can define a threaded recess (also referred to as a threaded hole) shaped and sized to receive a portion of the first conductive support member 140 and the second conductive support member 142. The heating element 120 can be retained between the first conductive support member 140 and the first electrical connector 150 and between the second conductive support member 142 and the second electrical connector 152. For example, the heating element 120 can define a first opening through which a portion of the first conductive support member 140 can be inserted into engagement with the first electrical connector 150 and a second opening through which a portion of the second conductive support member 142 can be inserted into engagement with the second electrical connector 150. In some embodiments, the first conductive support member 140 and the second conductive support member 142 can each be formed as a screw disposed partially or entirely within the fluid channel 130 and having threads configured to be received by the threaded recess of the first electrical connector 150 and the threaded recess of the second electrical connector 152 such that the heating element 120 is retained between the electrical connectors 150, 152 and the conductive support members 140, 142, respectively. For example, the heating element 120 can be disposed in contact with a bottom surface of a head of each screw and a top surface of each electrical connector 150, 152. In some embodiments, rather than the first conductive support member 140 and the second conductive support member 142 being formed as a screw, each can be formed as any suitable securing element configured to mate with and/or secure the heating element 120 to the first electrical connector 150 and the second electrical connector 152 (e.g., a rivet, a welded connection).

In some embodiments, the first electrical connector 150 and the second electrical connector 152 can each define a through-hole opening disposed parallel or co-axial to the direction of flow of fluid into the fluid channel 130 and a recess disposed perpendicular to the direction of the flow of fluid into the fluid channel 130 configured to receive a conductive plug. The first conductive support member 140 and the second conductive support member 142 can be formed as fin clamps disposed on (e.g., clamped to) the heating element 820 (e.g., to the opposite ends of the heating element 820). The first electrical connector 150 and the second electrical connector 152 can also define slots (e.g., recesses extending from opposing sides of the through-hole opening) configured to receive the fin clamps such that the fin clamps mate with and contact the first electrical connector 150 and the second electrical connector 152, respectively. The first electrical connector 150 and the second electrical connector 152 can receive the first fin clamp and the second fin clamp, respectively, such that the fin clamps are centered within the respective through-holes and fluid by diverted to a first or second side of the heating element 120 by the fin clamp. In some embodiments, the first electrical connector 150 is configured to be disposed in or coupled to the fluid inlet 132 and the second electrical connector 152 is configured to be disposed in or coupled to the fluid outlet 134. In some embodiments, the first electrical connector 150 and the second electrical connector 152 are each box-shaped.

In some embodiments, the system 100 can include more than one elongated heating element 120 to increase the surface area of the elongated heating elements(s) 120 within the fluid channel 130. For example, each elongated heating element 120 can be disposed in parallel, separated by conductive spacers, and coupled to a common first conductive support member 140 and a common second conductive support member 142. In some embodiments, rather than including distinct conductive support members 140, 142 and electrical connectors 150, 152, the first conductive support member 140 and the first electrical connector 150 can be formed as a combined component and/or the second conductive support member 142 and/or the second electrical connector 152 can be formed as a combined component. In some embodiments, rather than the first electrical connector 150 and the second electrical connector 152 being coupled to the elongated heating element 120 via the first conductive support member 140 and the second conductive support member 142, the elongated heating element 120 can be monolithically formed with first conductive support member (s) 140 and second conductive support member(s) 142 that are formed as protrusions or bosses that extend away from the heating element 120 and contact the channel wall forming the fluid channel 130 to center the elongated heating element 120 in the fluid channel 130.

In some embodiments, the fluid volume of the fluid channel 130 surrounding or partially surrounding the elongated heating element 120 can be between about 5 mL and about 150 mL to avoid temperature spikes and inconsistent temperatures if the volume is too low and excessive priming and warming time if the volume is too high.

The fluid inlet 132 and the fluid outlet 134 are configured to be coupled to intravenous (IV) tubing such that the fluid channel 130 can be disposed in-line with the IV tubing and fluid can flow from a fluid source 180 to a patient vasculature connector 190 via the fluid channel 130. In some embodiments, the system 100 can include or be coupled to a fluid pumping assembly 170 such that the fluid pumping assembly 170 can deliver fluid from the fluid source 180 to the fluid inlet 132, the fluid channel 130, the fluid outlet 134, and to the patient (e.g., via a patient vasculature connector 190). In some embodiments, the system 100 can include or be coupled to the fluid pumping assembly 170 such that the fluid pumping assembly 170 can draw fluid from the fluid source 180, into the fluid inlet 132, through the fluid channel 130, from the fluid outlet 134, and deliver the fluid to the patient (e.g., via a patient vasculature connector 190). The system 100 can be configured such that fluid can be warmed to a target temperature or temperature range (e.g. from between about 2-6° C. to about 38° C. or between about 36° C. and about 40° C.) as the fluid moves through the fluid channel 130 when the fluid pumping assembly 170 causes the fluid to flow through the fluid channel 130 at a rapid flow rate of between about 100 ml/min and about 1500 ml/min, between about 100 ml/min and about 1000 ml/min, or between about 750 ml/min and about 1000 ml/min. The system 100 can be configured such that fluid can be warmed to a target temperature or temperature range (e.g. from between about 2-6° C. to about 38° C. or between about 36° C. and about 40° C.) as the fluid moves through the fluid channel 130 when the fluid pumping assembly 170 causes the fluid to flow through the fluid channel 130 at a flow rate of about 0.1 ml/min or between about 0.1 ml/min and about 1500 ml/min. In some embodiments, rather than including or being coupled to a fluid pumping assembly 170, the fluid source 180 can be coupled to the fluid inlet 132 such that fluid from the fluid source 180 can be gravity-fed through the fluid channel 130.

In some embodiments, the system 100 can include or be coupled to a power source 162. The power source 162 can be configured to provide direct current (DC) electrical energy to the elongated heating element 120 via the first electrical connector 150 and the first conductive support member 140. The power source 162 can be, for example, a battery or any other DC power source.

In some embodiments, the system 100 can include or be coupled to a controller 161. The controller 161 can be electrically coupled to the power source 162 and can be configured to control the power provided by the power source 162 to the elongated heating element 120. In some embodiments, the controller 161 can be configured to control the power provided by the power source 162 to the elongated heating element 120 based on a temperature sensed by a temperature sensor 154. In some embodiments, the temperature sensor 154 can be fluidically coupled to the fluid in the fluid channel such that the temperature sensor 154 can directly sense the temperature of fluid within the fluid channel 130 (e.g., near an end of the elongated heating element near the fluid outlet), within the fluid outlet 134, or downstream of the fluid outlet 134). In some embodiments, the temperature sensor 154 can sense a temperature of fluid in the system 100 through a sidewall of IV tubing disposed downstream of the fluid outlet 134 or through the housing 110. In some embodiments, the system 100 can include more than one temperature sensor of one or more types, each coupled to the controller 161 and configured to provide temperature data to the controller 161. For example, two or more temperature sensors can be disposed within the fluid channel 130 or at any suitable location within the housing 110 or along the flow path from the fluid source 180 to the patient vasculature connector 190.

In some embodiments, the system 100 can adjust the power delivered to the elongated heating element 120 such that the temperature of the fluid output by the system 100 is maintained within a target range or at a target temperature based on temperature feedback provided by the temperature sensor 154 or any other temperature sensors included in the system 100. The target temperature can be, for example, body temperature. The target temperature range can be, for example, a range near body temperature, a range up to body temperature, or a range up to and slightly above body temperature. In some embodiments, the target temperature can be 38° C. In some embodiments, the target temperature range can be between about 36° C. and about 40° C.

In some embodiments, the temperature sensor 154 can be a device for measuring the infusate temperature in the warmer system 100, which can be located in a fluid drive assembly such as the reusable drive assembly portion 164 discussed below. In some embodiments, the temperature sensor 154 can include a thermocouple, thermistor, or other suitable temperature measuring device. In some embodiments, the temperature sensor 154 can include a controller which receives and interprets signals from such devices. In some embodiments, the temperature sensor 154 can include an infrared sensor which detects the temperature of a portion of a fluid delivery assembly (e.g., the fluid pumping assembly 170) including or coupled to the warmer system 100 and in contact with warmed fluid.

In some embodiments, the warmer system 100 can include a temperature sensing area, which is a portion of the warmer system 100 or area near the warmer system 100 which allows for detection of fluid temperature and is in communication with the temperature sensor 154. In some embodiments, the temperature sensing area includes a thermocouple, thermistor, or other suitable temperature measuring device which is in direct contact with the infused fluid. In some embodiments, the temperature sensing area includes a thermocouple, thermistor, or other suitable temperature measuring device which is directly adjacent to the fluid path, but not in contact with fluid in the fluid path. In some embodiments, the temperature sensing area include a thin area of material which is in contact with the infusate. A thermocouple, thermistor, IR sensor, or other method of sensing temperature can be included in the fluid drive assembly (e.g., the reusable drive assembly portion 164 discussed below) and disposed in contact or in close proximity to the thin area of material. The temperature of the thin area of material would approximate the fluid temperature and change temperature rapidly when the infusate temperature changes. In some embodiments, a thermocouple or thermistor can be included in the fluid channel, and electrical insulation can be included to prevent the electricity being used to create heat in the heating element 120 from shorting into the thermocouple or thermistor.

In some embodiments, the system 100 includes at least one temperature sensing area. In some embodiments, the system 100 includes a temperature sensing area for measuring the maximum temperature of the infused fluid at the fluid outlet 134 of the warmer system 100. In some embodiments, the system 100 includes additional temperature sensing areas, such as at the fluid inlet 132 and/or at one or more locations along the fluid channel 130.

In some embodiments, the controller 161 and/or the power source 162 can be included in a common fluid infusion assembly 165. In some embodiments, the fluid infusion assembly 165 includes the fluid pumping assembly 170. In some embodiments, the fluid infusion assembly 165 includes a reusable drive assembly portion 164 and a disposable portion 166 that includes the fluid pumping assembly 170. The drive assembly portion 164 can include, for example, the controller 161, the power source 162, and/or a motor 163. The drive assembly portion 164 can be configured to be releasably mechanically and, optionally, electrically coupled to the fluid pumping assembly 170. For example, the disposable portion 166 can be coupled to the drive assembly portion 164 via a mechanical coupling (including drive engagement components, retention components, and/or alignment components) and an electrical coupling (configured for the transfer of power and/or data). When the fluid pumping assembly 170 is releasably coupled to the drive assembly portion 164, the drive assembly portion 164 (e.g., the controller 161 operatively coupled to the motor 163) can control delivery of fluid from the fluid pumping assembly 170 (e.g., to a patient P). For example, the drive assembly portion 164 can be releasably coupled to the fluid pumping assembly 170 to control delivery of fluid from the fluid pumping assembly 170 to provide rapid and/or continuous (e.g., non-pulsatile) fluid flow from the fluid pumping assembly 170. The drive assembly portion 164 can be the same or similar in structure and/or function to any of the drive assemblies described in International Patent Application No. PCT/US2022/019381 to Robertson et al., filed Mar. 8, 2022, entitled Systems, Apparatus, and Methods for Fluid Infusion (hereinafter Robertson '381), which is incorporated by reference herein in its entirety. The fluid pumping assembly 170 can be the same or similar in structure and/or function to any of the fluid delivery assemblies described in Robertson '381. In some embodiments, rather than a common controller 161 controlling both the delivery of power from the power source 162 to the elongated heating element 120 and operation of the fluid infusion assembly 165 to deliver fluid from the fluid source 180 to a patient via the fluid channel 130, a separate controller can be included or coupled to the fluid infusion assembly 165 to control operation of the fluid pumping assembly 170. In some embodiments, rather than a common power source 162 providing power for both the delivery of power to the elongated heating element 120 and for operation of the fluid infusion assembly 165 to deliver fluid from the fluid source 180 to a patient via the fluid channel 130, a separate power source can be included or coupled to the fluid infusion assembly 165 to control operation of the fluid pumping assembly 170. In some embodiments, rather than the system 100 including a fluid infusion assembly such as the fluid infusion assembly 165 including a fluid pumping assembly 170, the system 100 can be configured as a stand-alone fluid warmer that can be used in conjunction with tubing (e.g., intravenous tubing) to warm fluid flowing therethrough (e.g., to a patient), and may optionally be couplable to any suitable source of fluid and/or any suitable fluid dispensing device.

Figure 2:
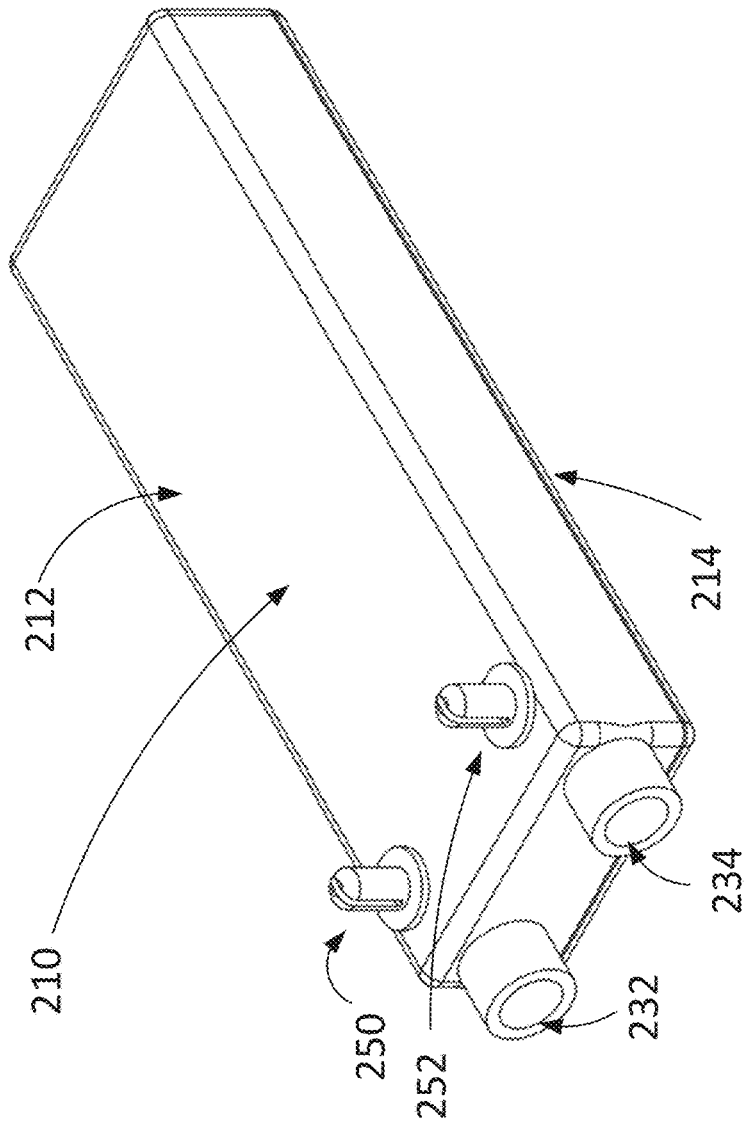
FIGS. 2 and 3 are various views of a fluid warmer system, according to an embodiment.

FIG. 2 is a perspective view of a bottom of a system 200. The system 200 can be the same or similar in structure and/or function to any of the systems described herein, such as the system 100. For example, the system 200 includes a housing 210 defining a fluid inlet 232 and a fluid outlet 234, a first electrical connector 250, and a second electrical connector 252. The housing 210 includes a first portion 212 and a second portion 214. The first portion 212 can include the fluid inlet 232 and the fluid outlet 234 and defining openings within which the first electrical connector 250 and the second electrical connector 252 can be disposed. The first portion 212 can define a fluid channel 230 (shown in FIG. 3) and the second portion 214 can be formed as a lid configured to form a sidewall of the fluid channel 230 when coupled to the first portion 212.

Figure 3:
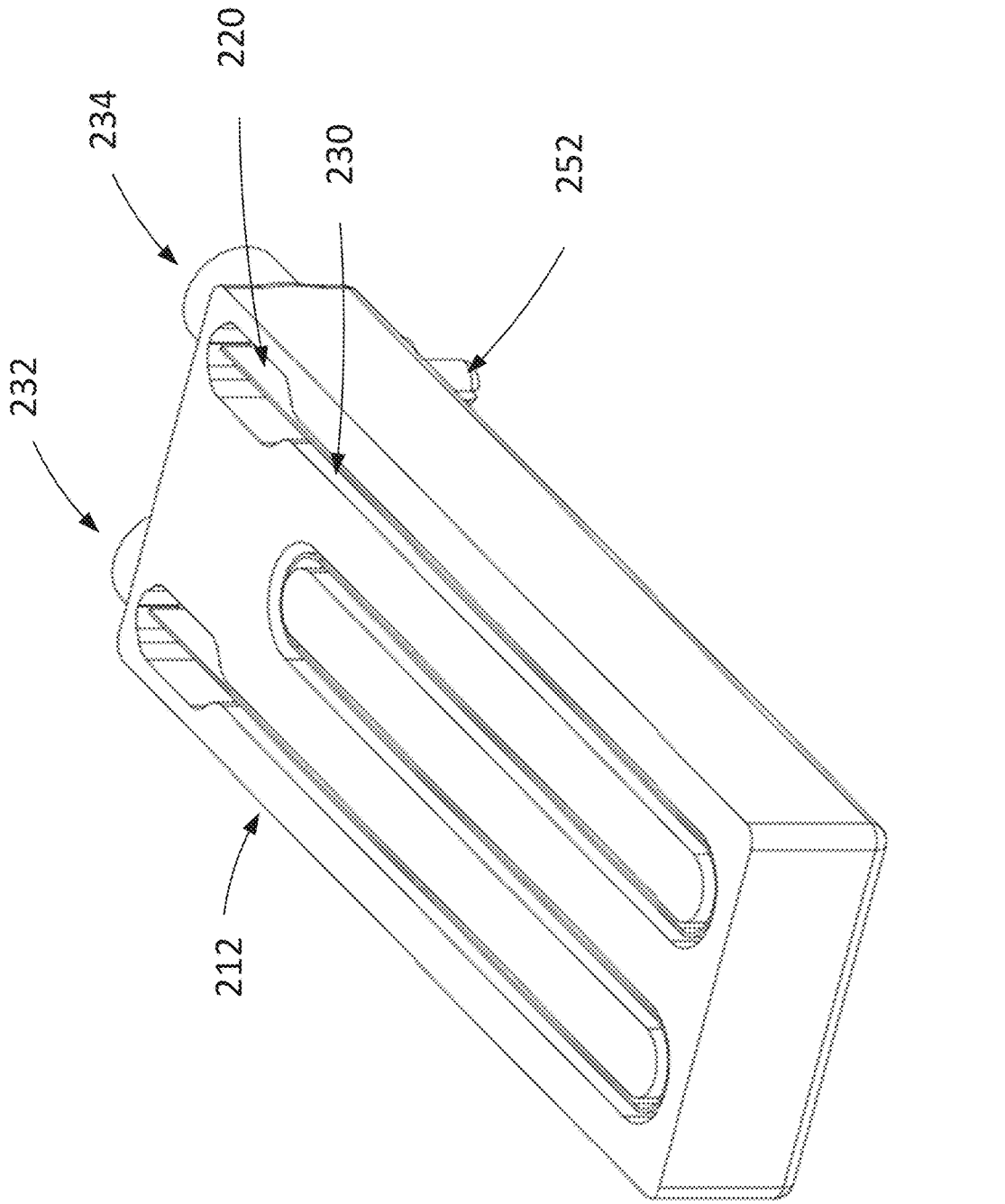

FIG. 3 is a perspective view of a top of a system 200 with the second portion 214 not shown. As shown, the system 200 includes an elongated heating element 220. The first portion 212 of the housing 210 can define the fluid channel 230 such that the fluid channel 230 includes portions that are wider in the area where the first electrical connector 250 and the second electrical connector 252 are coupled to the elongated heating element 220, respectively (e.g., via a first conductive support member and a second conductive support member, respectively (not shown)).

Figure 4:
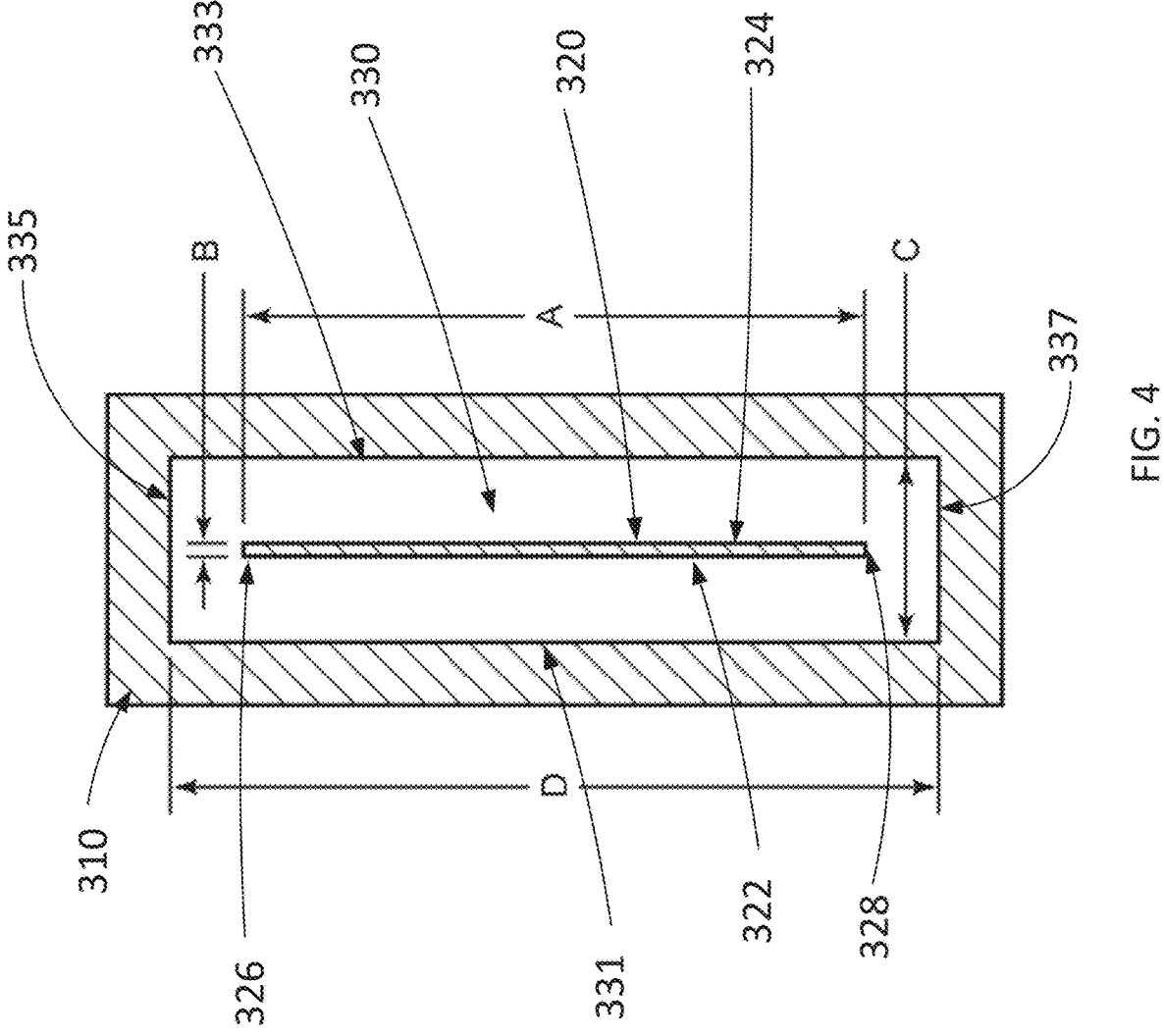
FIG. 4 is a cross-sectional illustration of a housing defining a rectangular fluid channel and an elongated heating element formed as a ribbon, according to an embodiment.

FIG. 4 is a cross-sectional illustration of a housing 310 defining a rectangular fluid channel 330 and an elongated heating element 320 formed as a ribbon. The housing 310, the fluid pathway 330, and the elongated heating element 320 can be the same or similar in structure and/or function as any of the housings, fluid pathways, and elongated heating elements described herein. As shown, the elongated heating element 320 can have a first side surface 322, a second side surface 324, an upper surface 326, and a lower surface 328. The elongated heating element 320 has a width B between the first side surface 322 and the second side surface 324 smaller than a height A of the elongated heating element 320 between the upper surface 326 and the lower surface 328. The fluid channel 330 can be defined by a first sidewall 331, a second sidewall 333 opposite the first sidewall 331, an upper wall 335 disposed perpendicularly to the first sidewall 331 and the second sidewall 333, and a lower wall 337 opposite the upper wall 335. The first sidewall 331 and the second sidewall 333 can be separated by a distance C. The upper wall 335 and the lower wall 337 can be separated by a distance D. As shown in FIG. 4, the elongated heating element 320 can be centered within the fluid channel 330 such that a distance between the first side surface 322 and the first sidewall 331 is the same as a distance between the second side surface 324 and the second sidewall 333, and a distance between the upper surface 326 and the upper wall 335 is the same as a distance between the lower surface 328 and the lower wall 337. The height A can be between about. 0.075" and about 0.500". The width B can be between about 0.001" and about 0.050". The distance C can be between about 0.50" and about 0.500". The distance D can be between about the height A and about 0.500" or about two to three times the height A.

Figure 5:
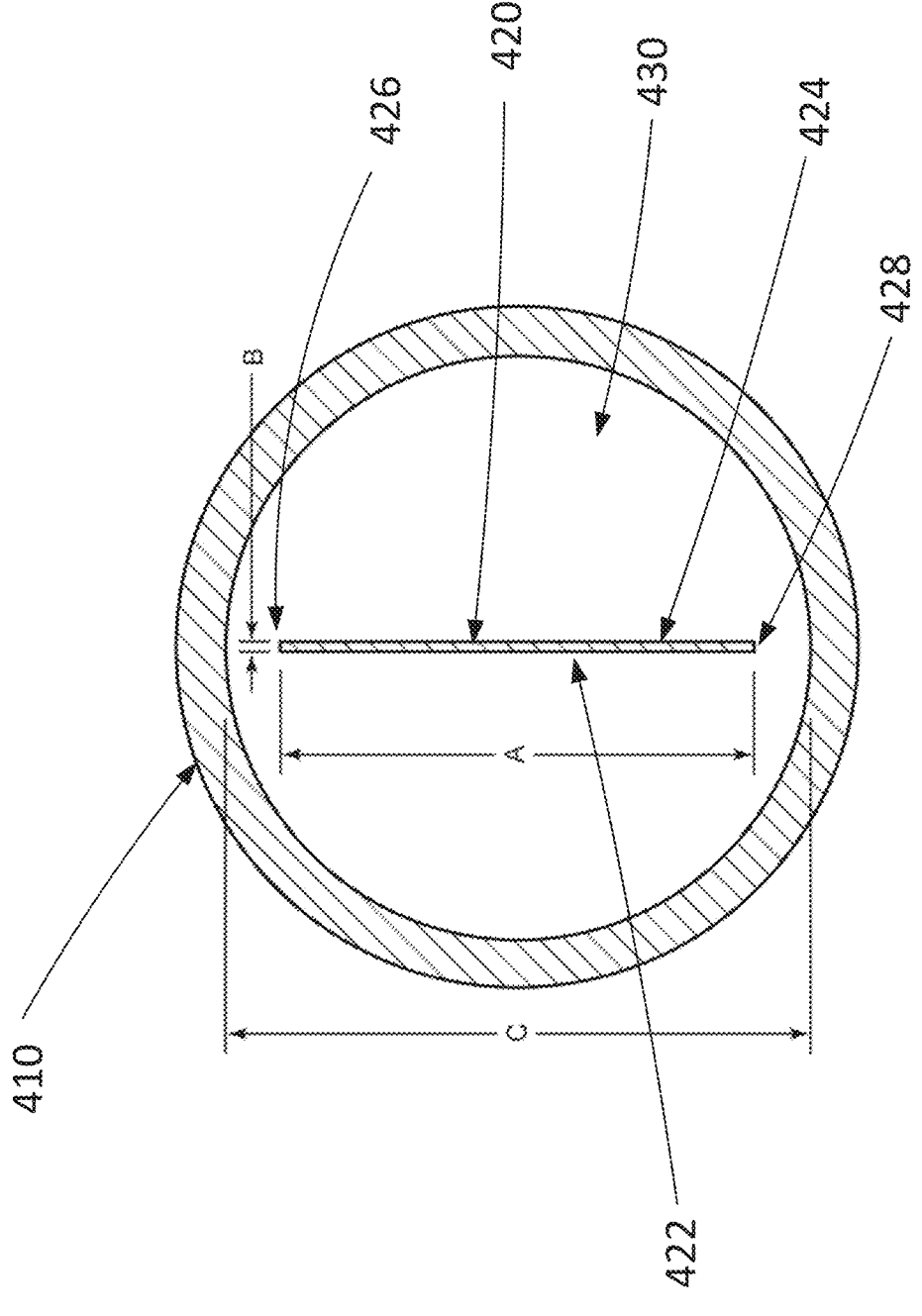
FIG. 5 is a cross-sectional illustration of a housing defining a circular fluid channel and an elongated heating element formed as a ribbon, according to an embodiment.

FIG. 5 is a cross-sectional illustration of a housing 410 defining a circular fluid channel 430 and an elongated heating element 420 formed as a ribbon. The housing 410, the fluid pathway 430, and the elongated heating element 420 can be the same or similar in structure and/or function as any of the housings, fluid pathways, and elongated heating elements described herein. As shown, the elongated heating element 420 can have a first side surface 422, a second side surface 424, an upper surface 426, and a lower surface 428. The elongated heating element 420 has a width B between the first side surface 422 and the second side surface 424 smaller than a height A of the elongated heating element 420 between the upper surface 426 and the lower surface 428. The fluid channel 430 can have a diameter C. The height A can be between about 0.075" and about 0.500". The width B can be between about 0.001" and about 0.050". The diameter C can be, for example, between about the height A and about 0.500" or about two to three times the height A. As shown in FIG. 5, the elongated heating element 420 can be centered within the fluid channel 430.

Figure 6:
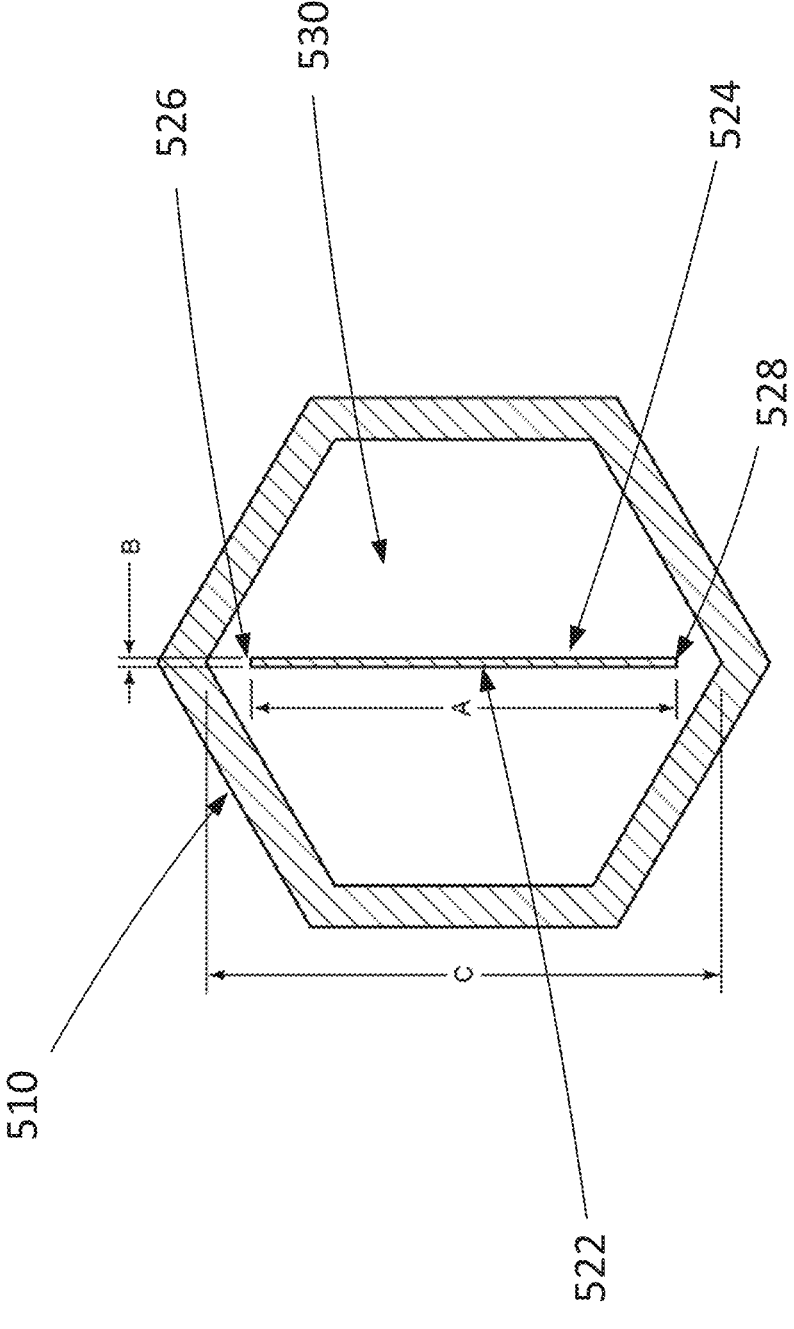
FIG. 6 is a cross-sectional illustration of a housing defining a hexagonal fluid channel and an elongated heating element formed as a ribbon, according to an embodiment

FIG. 6 is a cross-sectional illustration of a housing 510 defining a hexagonal fluid channel 530 and an elongated heating element 520 formed as a ribbon. The housing 510, the fluid pathway 530, and the elongated heating element 520 can be the same or similar in structure and/or function as any of the housings, fluid pathways, and elongated heating elements described herein. As shown, the elongated heating element 520 can have a first side surface 522, a second side surface 524, an upper surface 526, and a lower surface 528. The elongated heating element 520 has a width B between the first side surface 522 and the second side surface 524 smaller than a height A of the elongated heating element 520 between the upper surface 526 and the lower surface 528. The fluid channel 530 can have a maximum width C. The width B can be between about 0.001" and about 0.050". The maximum width C can be, for example, between about can be between about the height A and about 0.500" or about two to three times the height A. As shown in FIG. 6, the elongated heating element 520 can be centered within the fluid channel 530.

Figure 7:
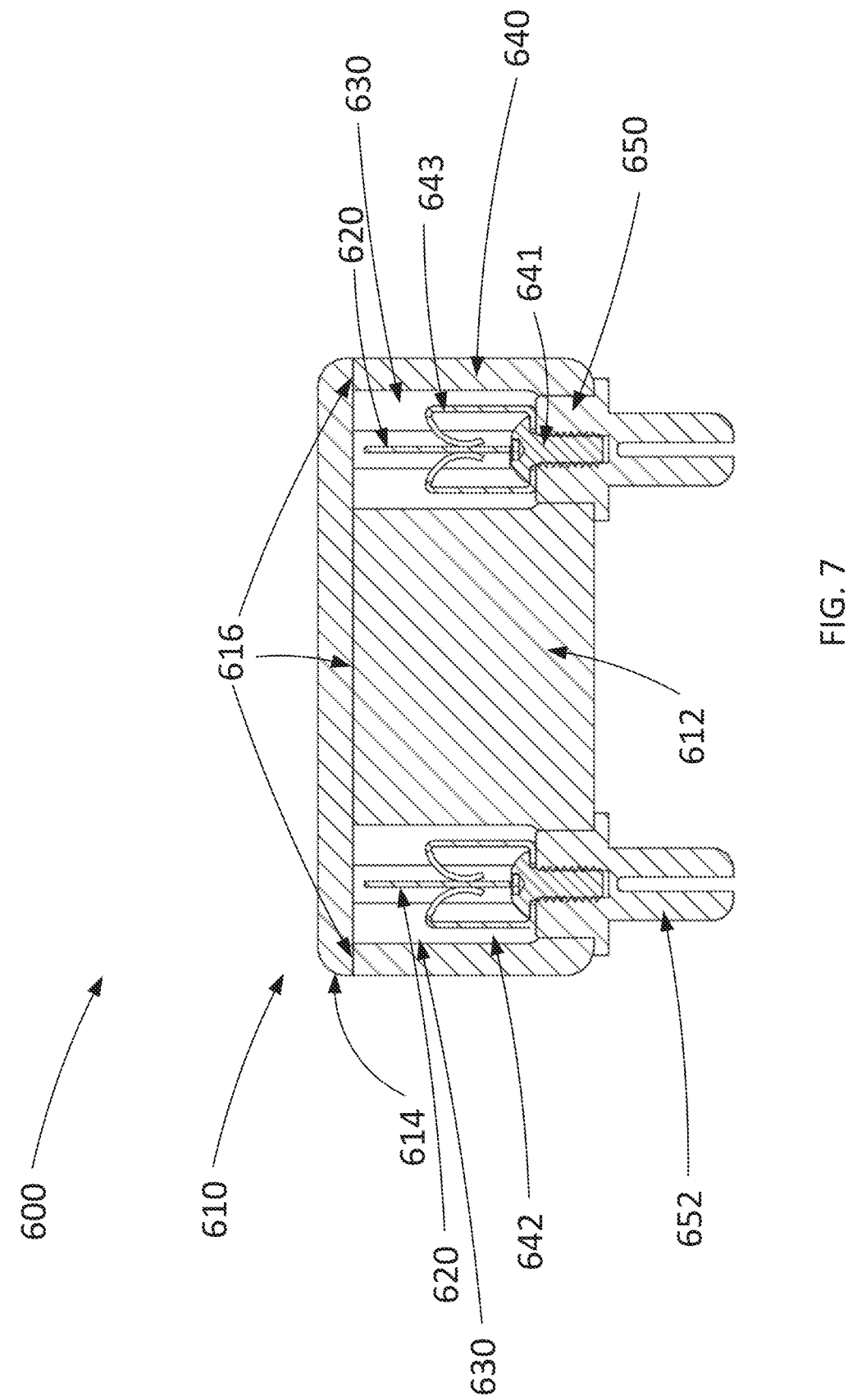
FIG. 7 is a cross-sectional illustration of a fluid warmer system, according to an embodiment

FIG. 7 is a cross-sectional illustration of a system 600. The system 600 can be the same or similar in structure and/or function to any of the systems described herein. For example, the system 600 can include a housing 610, an elongated ribbon-shaped heating element 620, a first conductive support member 640, a second conductive support member 642, a first electrical connector 650, and a second electrical connector 652. As shown, the housing 610 can include a first portion 612 and a second portion 614 formed as a lid. The first portion 612 defines a fluid channel 630 and can be coupled to the second portion 614 via a seal 616 such that the first portion 612, the second portion 614, and the seal 616 collectively define the fluid channel 630.

As shown in FIG. 7, each of the first conductive support member 640 and the second conductive support member 642 include a first portion and a second portion. For example, the first conductive support member 640 includes a first portion 641 and a second portion 643. The first portion 641 can be formed as a screw and the second portion 643 can be formed as a metal clip (e.g., a leaf spring) disposed entirely within the fluid channel 630 and configured to engage with and support the heating element 620. Each of the first electrical connector 650 and the second electrical connector 652 can be formed as a male plug. The cross-sectional thickness of the metal portions forming the clip of the second portion 643 can all be smaller than the cross-sectional thickness (e.g., diameter) of the screw of the first portion 641 and the cross-sectional thickness (e.g., diameter) of the first electrical connector 650. Thus, the portions of the system 600 disposed within the fluid channel 630 and contacting fluid will generate higher amounts of heat than the first electrical connector 650 and the second electrical connector 652 due to their relative shapes and sizes (e.g., thicknesses). Additionally, the interface between the first portion 641 and the second portion 643 can be disposed entirely within the fluid channel 630 such that fluid traveling through the fluid channel 630 can contact both the first portion 641 and the second portion 643, with the second portion 643 disposed entirely within the fluid channel 630 and the first portion 641 disposed at least partially within the fluid channel 630.

Figure 8:
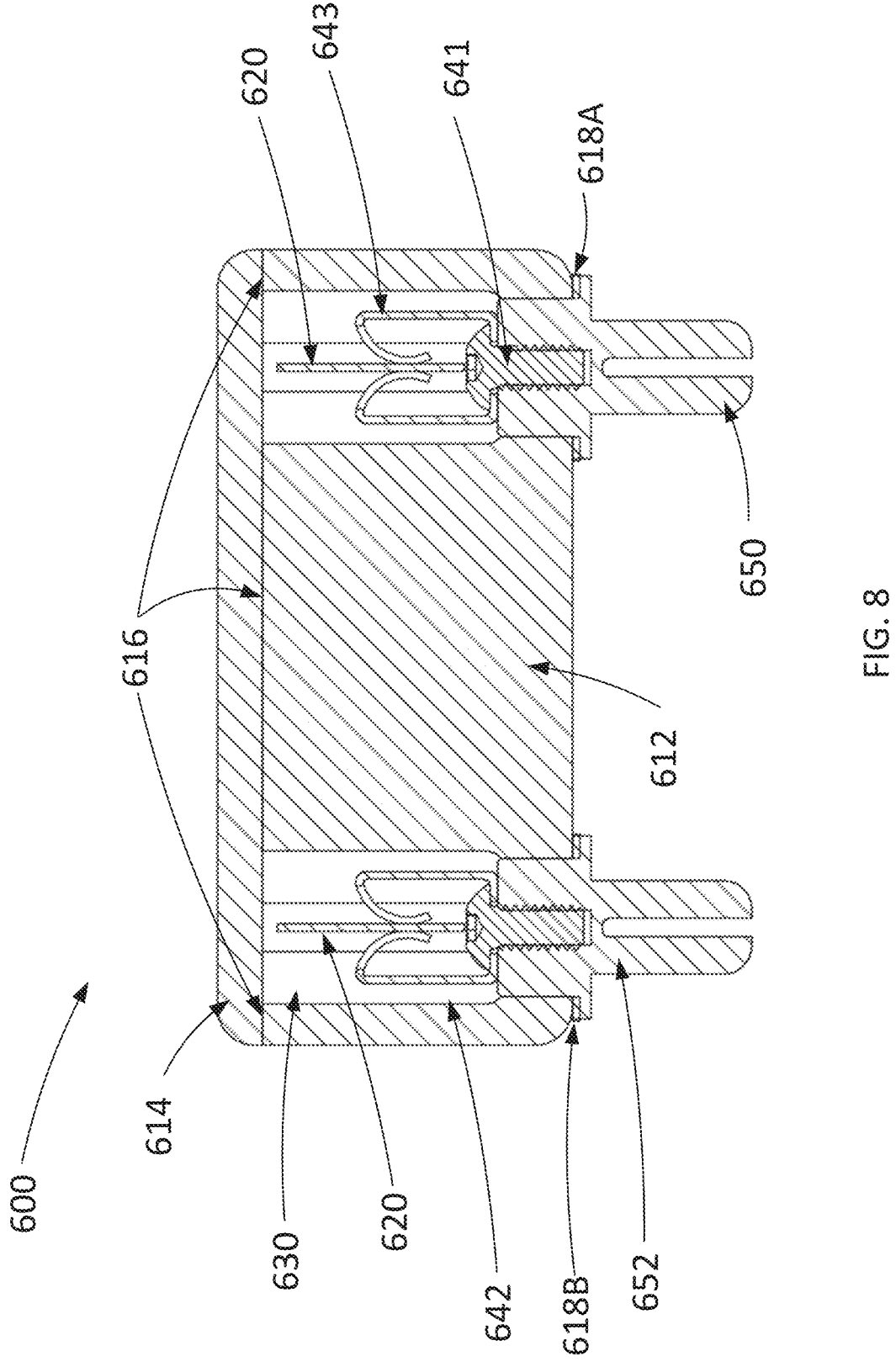
FIG. 8 is a cross-sectional illustration of the fluid warmer system of FIG. 7 including gaskets, according to an embodiment.

In some embodiments, as shown in FIG. 8, gaskets 618A,B can be disposed between the first electrical connector 650 and the second electrical connector 652, respectively, and the first portion 612 of the housing 610. Each of the gaskets 618A,B can prevent fluid within the fluid channel 630 from flowing out of the fluid channel 630 via the through-holes in the housing 610 within which the first electrical connector 650 and the second electrical connector 652 are disposed.

Figure 9:
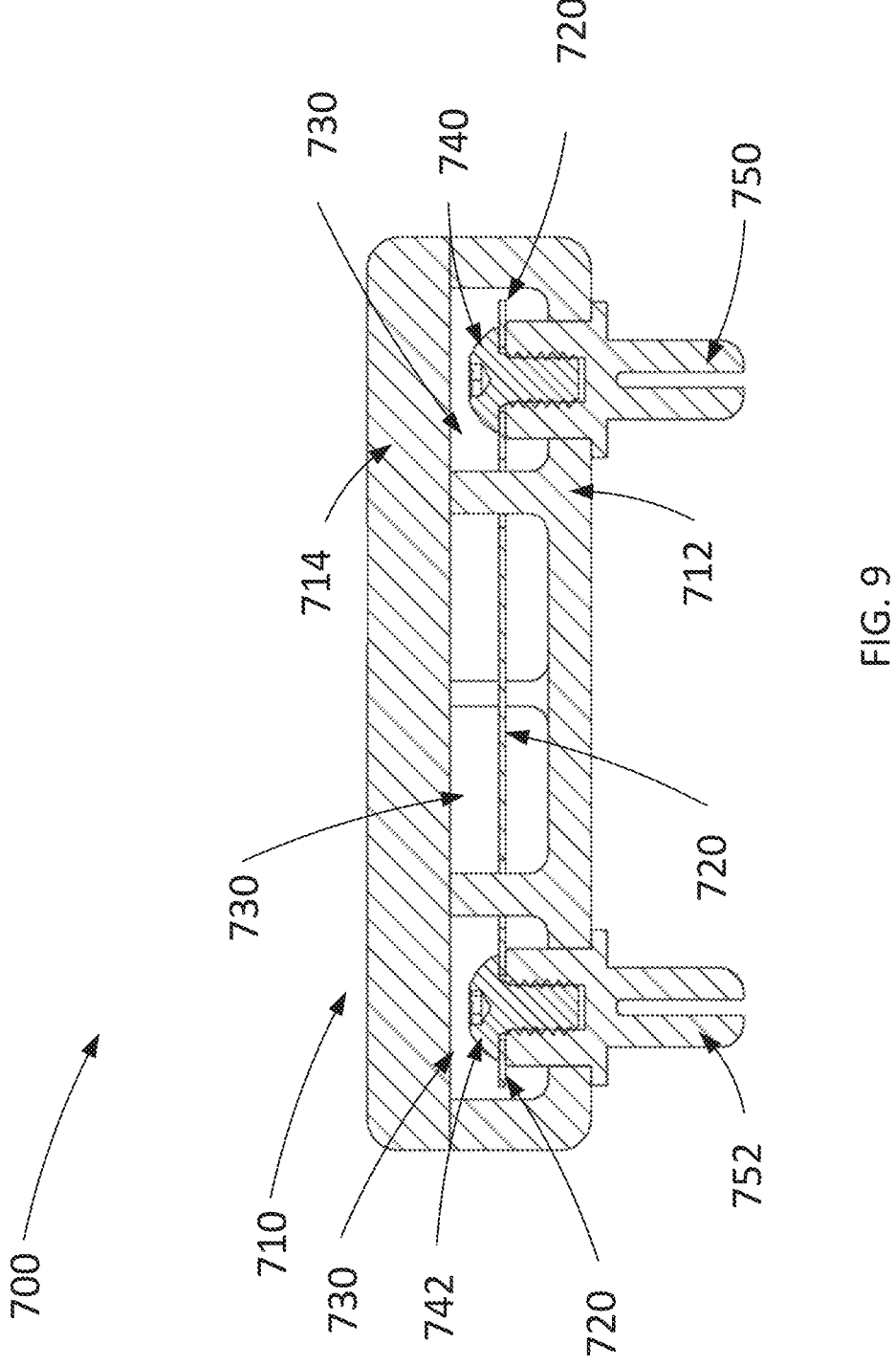
FIG. 9 is a cross-sectional illustration of a fluid warmer system, according to an embodiment.

FIG. 9 is a cross-sectional illustration of a system 700. The system 700 can be the same or similar in structure and/or function to any of the systems described herein. For example, the system 700 can include a housing 710, an elongated flat coil heating element 720, a first conductive support member 740, a second conductive support member 742, a first electrical connector 750, and a second electrical connector 752. As shown, the housing 710 can include a first portion 712 and a second portion 714 formed as a lid. The first portion 712 defines a fluid channel 730 and can be sealingly coupled to the second portion 714 such that the first portion 712 and the second portion 714 collectively define the fluid channel 730.

As shown in FIG. 9, each of the first conductive support member 740 and the second conductive support member 742 can be formed as a screw. Each of the first electrical connector 750 and the second electrical connector 752 can be formed as a male plug and can include a top surface and define a threaded recess (also referred to as a threaded hole) shaped and sized to receive a portion of the first conductive support member 740 and the second conductive support member 742. The heating element 720 can be retained between the first conductive support member 740 and the first electrical connector 750 and between the second conductive support member 742 and the second electrical connector 752. For example, the heating element 720 can define a first opening through which a portion of the first conductive support member 740 can be inserted into engagement with the first electrical connector 750 and a second opening through which a portion of the second conductive support member 742 can be inserted into engagement with the second electrical connector 750. The first electrical connector 750 and the second electrical connector 752 can each be disposed partially or entirely within the fluid channel 730 and can have threads configured to be received by the threaded recess of the first electrical connector 750 and the threaded recess of the second electrical connector 752 such that the heating element 720 is retained between the electrical connectors 750, 752 and the conductive support members 740, 742, respectively. For example, as shown, the heating element 720 can be disposed in contact with a bottom surface of a head of each screw and a top surface of each electrical connector 750, 752.

Figure 10:
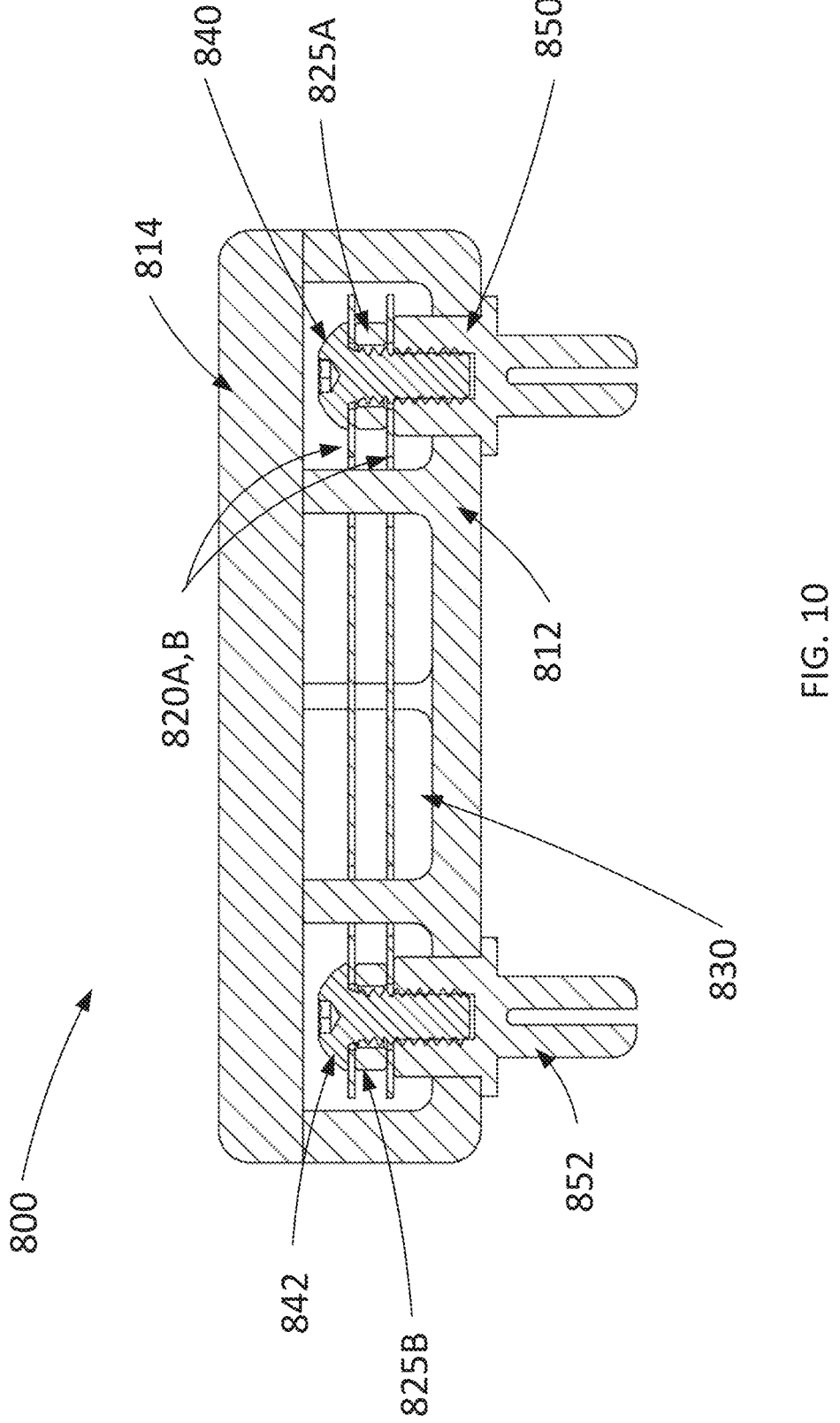
FIG. 10 is a cross-sectional illustration of a fluid warmer system, according to an embodiment.

FIG. 10 is a cross-sectional illustration of a system 800. The system 800 can be the same or similar in structure and/or function to any of the systems described herein. For example, the system 800 can include a housing 810, a first elongated heating element 820A, a second elongated heating element 820B, a first conductive support member 840, a second conductive support member 842, a first electrical connector 850, and a second electrical connector 852. As shown, the housing 810 can include a first portion 812 and a second portion 814 formed as a lid. The first portion 812 defines a fluid channel 830 and can be sealingly coupled to the second portion 814 such that the first portion 812 and the second portion 814 collectively define the fluid channel 830.

As shown in FIG. 10, each of the first conductive support member 840 an the second conductive support member 842 can be can be formed as a screw. Each of the first electrical connector 850 and the second electrical connector 852 can be formed as a male plug and can include a top surface and define a threaded recess (also referred to as a threaded hole) shaped and sized to receive a portion of the first conductive support member 840 and the second conductive support member 842. The first heating element 820A and the second heating element 820B can be retained between the first conductive support member 840 and the first electrical connector 850 and between the second conductive support member 842 and the second electrical connector 852, but separated by a conductive first spacer 825A and a conductive second spacer 825B such that the first elongated heating element 820A and second elongated heating element 820B are electrically connected in parallel via the first spacer 825A and the second spacer 825B, respectively. Each of the first spacer 825A and the second spacer 825B can be shaped, for example, as circular discs. Each heating element 820A,B can define a first opening through which a portion of the first conductive support member 840 can be inserted into engagement with the first electrical connector 850 and a second opening through which a portion of the second conductive support member 842 can be inserted into engagement with the second electrical connector 850. The first electrical connector 850 and the second electrical connector 852 can each be disposed partially or entirely within the fluid channel 830 and can have threads configured to be received by the threaded recess of the first electrical connector 850 and the threaded recess of the second electrical connector 852 such that the heating elements 820A,B are retained between the electrical connectors 850, 852 and the conductive support members 840, 842, respectively. For example, as shown, the heating element 820A can be disposed in contact with a bottom surface of a head of each screw and the heating element 820B can be disposed in contact with a top surface of each electrical connector 850, 852.

Figure 11:
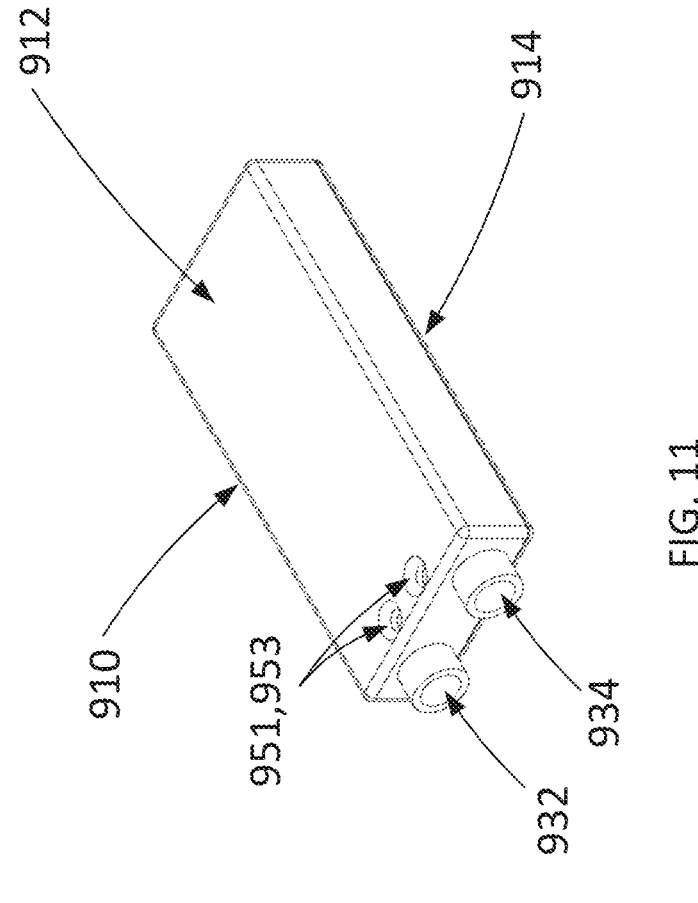
FIGS. 11-16 are various views of a fluid warmer system, according to an embodiment.

FIGS. 11-16 are various views of a system 900. FIG. 11 is a perspective view of a bottom of the system 900. The system 900 can be the same or similar in structure and/or function to any of the systems described herein. For example, the system 900 can include a housing 910, an elongated heating element 920, a first conductive support member 940, a second conductive support member 942, a first electrical connector 950, and a second electrical connector 952. As shown, the housing 910 can include a first portion 912 and a second portion 914 formed as a lid. The first portion 912 defines a fluid channel 930 and can be sealingly coupled to the second portion 914 such that the first portion 912 and the second portion 914 collectively define a fluid channel 930.

Figure 12:
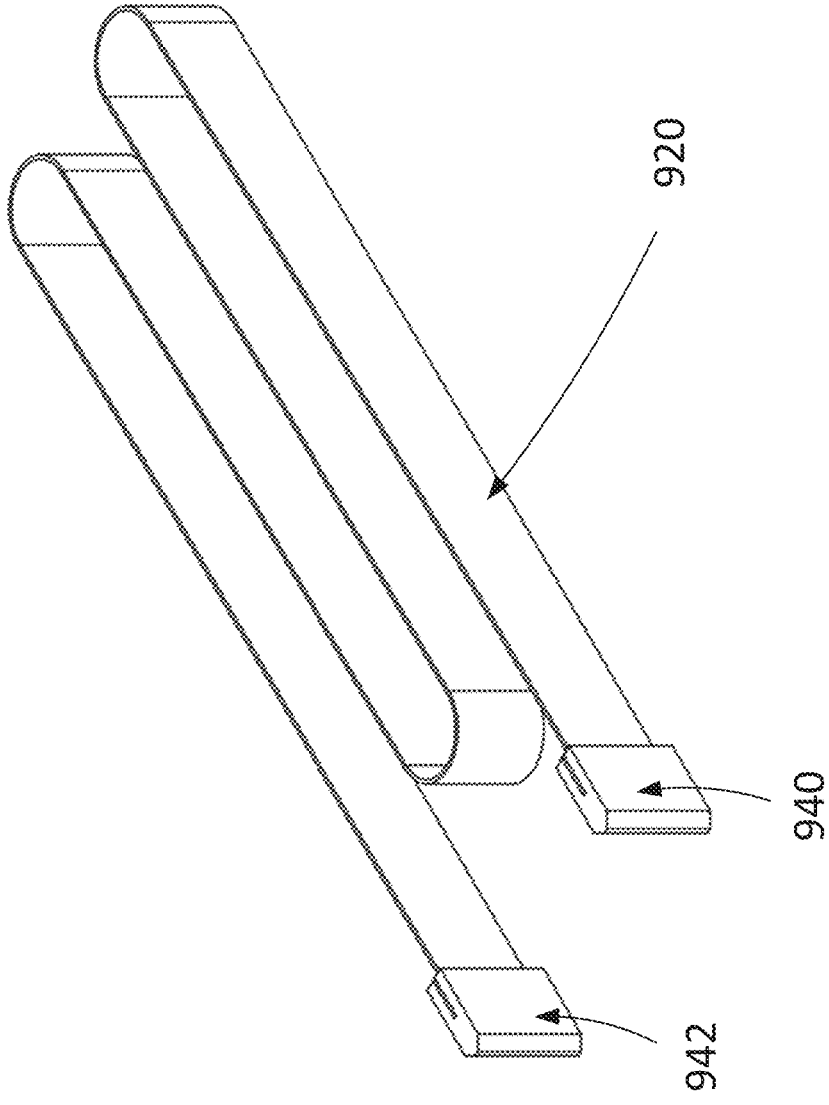

FIG. 12 is a perspective view of the elongated heating element 920, the first conductive support member 940, and the second conductive support member 942. As shown, the first conductive support member 940 and the second conductive support member 942 are formed as fin clamps disposed on (e.g., clamped to) opposite ends of the heating element 920.

Figure 13:
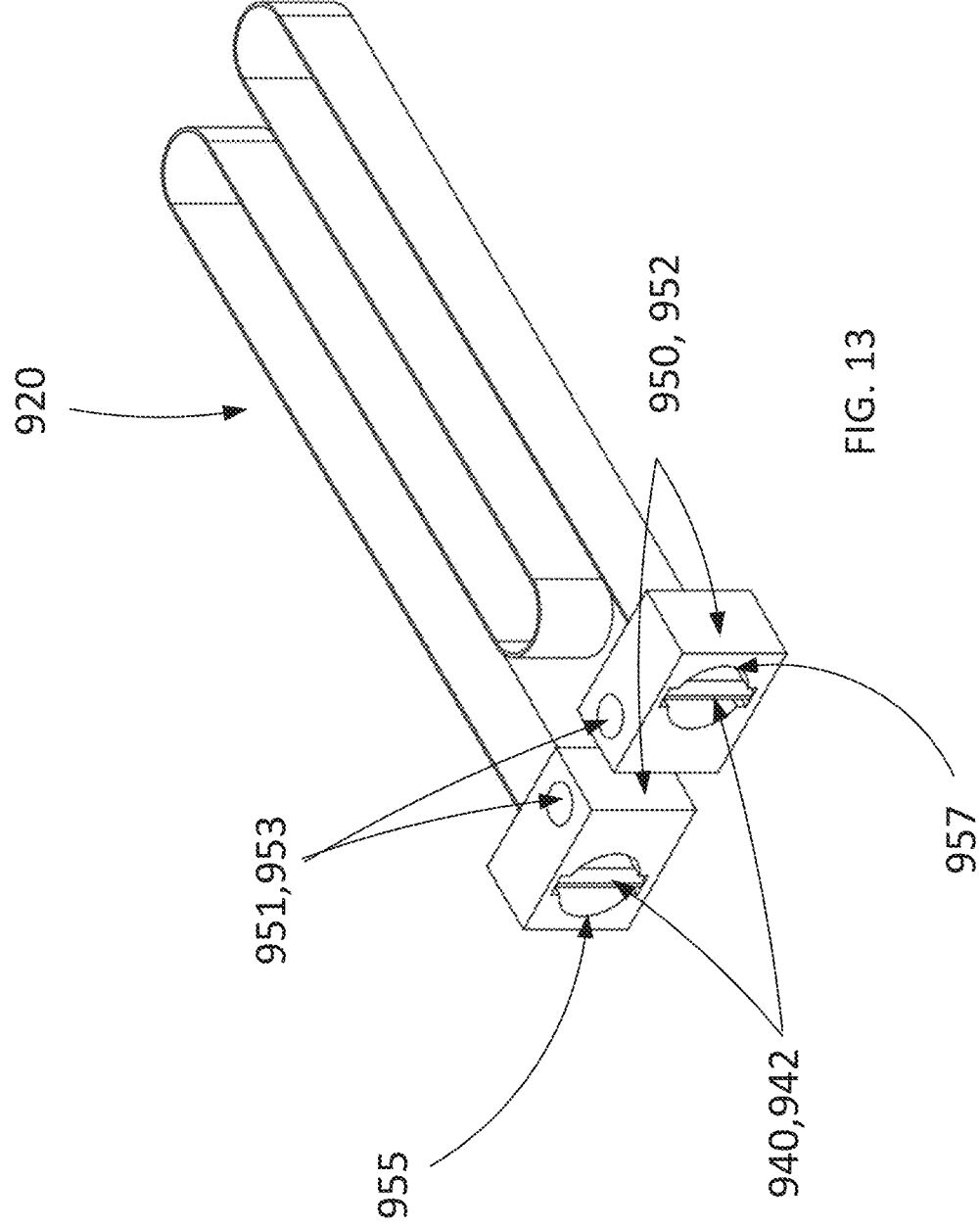
Figures 14, 15:
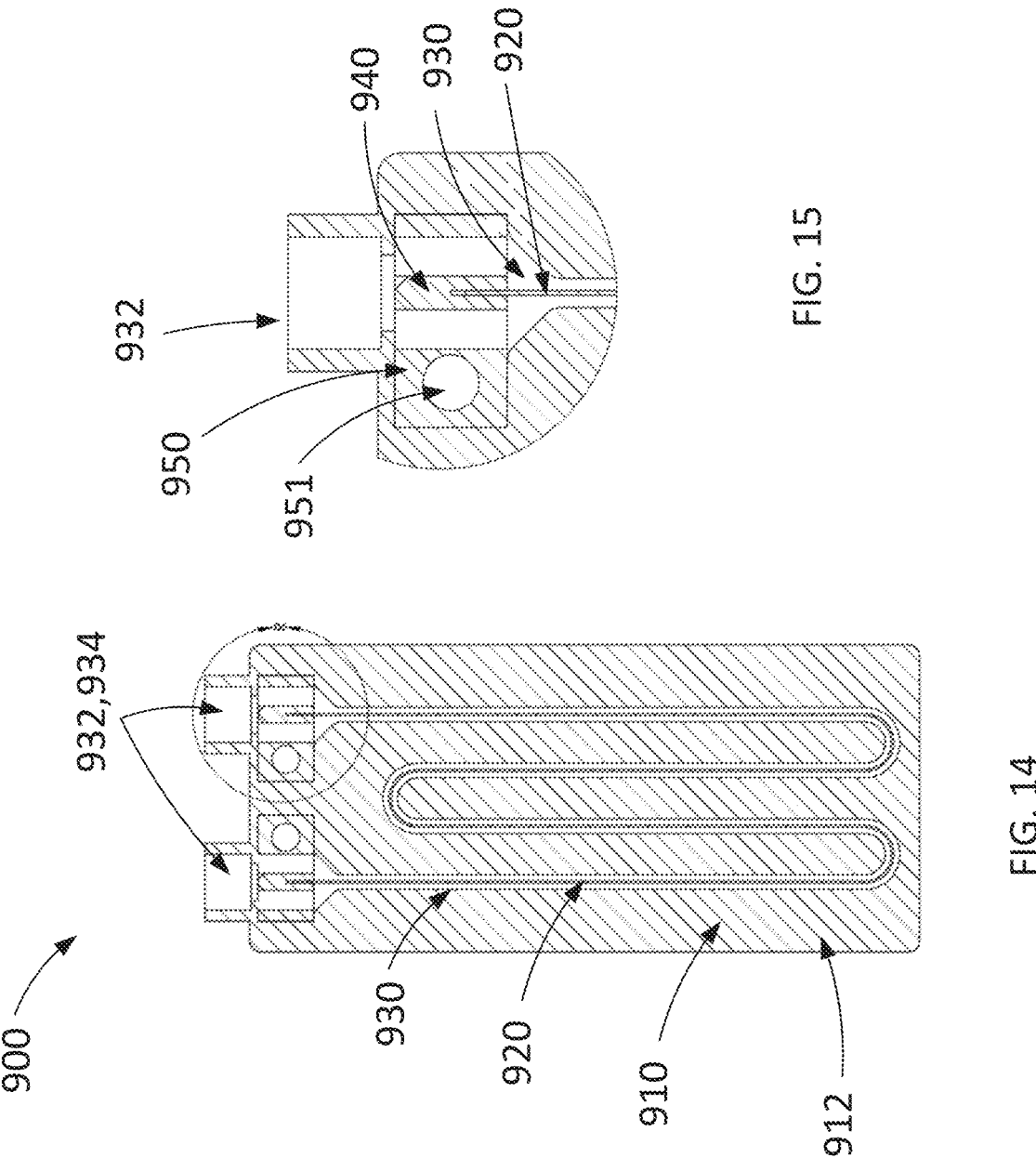
Figure 16:
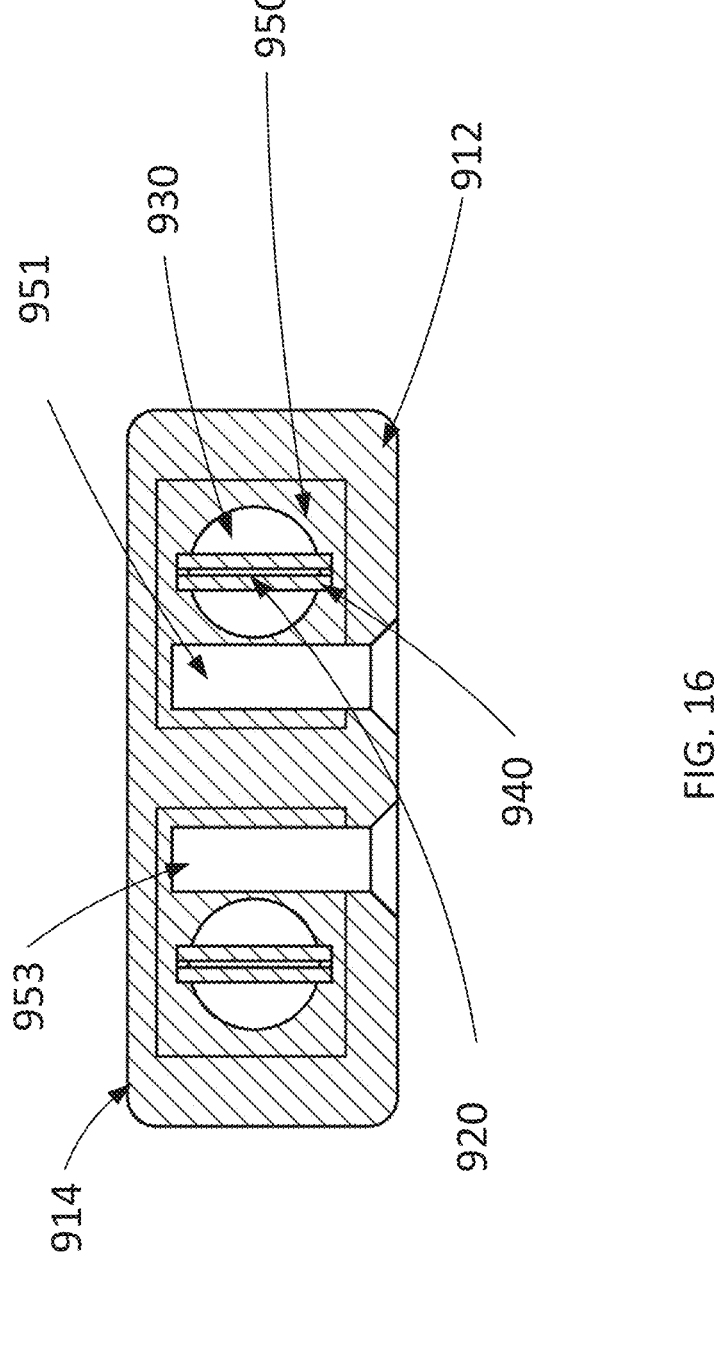

FIG. 13 is a perspective view of the elongated heating element 920, the first conductive support member 940, the second conductive support member 942, the first electrical connector 950, and the second electrical connector 952. As shown, the first electrical connector 950 and the second electrical connector 952 can each define a through-hole opening 955, 957 disposed parallel or co-axial to the direction of flow of fluid into the fluid channel 930 and a recess 951, 953 disposed perpendicular to the direction of the flow of fluid into the fluid channel 930 configured to receive a conductive plug such that power can be provided from a power supply (e.g., the power source 162) to the first electrical connector 950 and/or the second electrical connector 952 via the conductive plug. In some embodiments, each of the recess 951 and 953 can be formed as a female electrical connector (e.g., a female plug) configured to mate with a complementary male electrical connector (e.g., a male plug). As shown in FIG. 11, the housing 910 (e.g., the first portion 912) can define sidewall openings through which the recesses 951 and 953 can be accessed (e.g., by a conductive plug) from an exterior of the housing 910. In some embodiments, the recess 951 and/or the recess 953 can be oriented within the first conductive support member 940 and the second conductive support member 942, respectively, and the sidewall openings can be defined by the housing 910 such that the recess 951 and/or the recess 953 can be accessed through the second portion 914 and/or through an outer surface of the housing 910 that is perpendicular or parallel to the bottom surface through which the sidewall openings are defined in FIG. 11. The first electrical connector 950 and the second electrical connector 952 can also define slots (e.g., recesses extending from opposing sides of the through-hole opening) configured to receive the fin clamps such that the fin clamps mate with and contact the first electrical connector 950 and the second electrical connector 952, respectively. The first electrical connector 950 and the second electrical connector 952 can receive the first fin clamp and the second fin clamp, respectively, such that the fin clamps are centered within the respective through-holes and fluid by diverted to a first or second side of the heating element 920 by the fin clamp. In some embodiments, the first electrical connector 950 is configured to be disposed in or coupled to the fluid inlet 932 and the second electrical connector 952 is configured to be disposed in or coupled to the fluid outlet 934. As shown in FIG. 13, the first electrical connector 950 and the second electrical connector 952 are each box-shaped. FIG. 14 is a cross-sectional view of the system 900. FIG. 15 is an enlarged view of the portion R in FIG. 14. FIG. 16 is a cross-sectional view of the system 900 taken in a plane perpendicular to that of the view of FIG. 14.

Figures 20, 21:
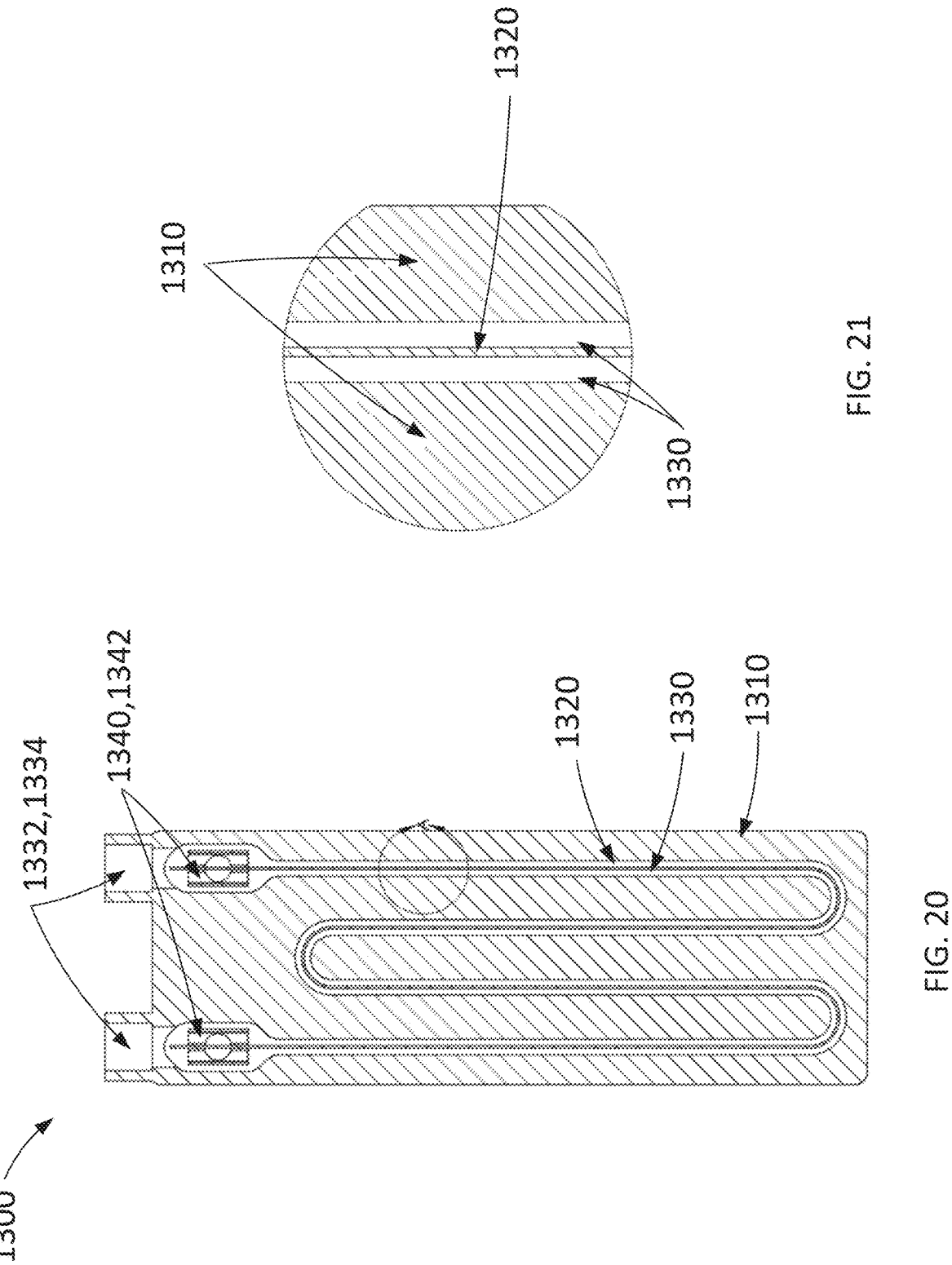
FIGS. 20-22 are various views of a fluid warmer system, according to an embodiment.
Figure 22:
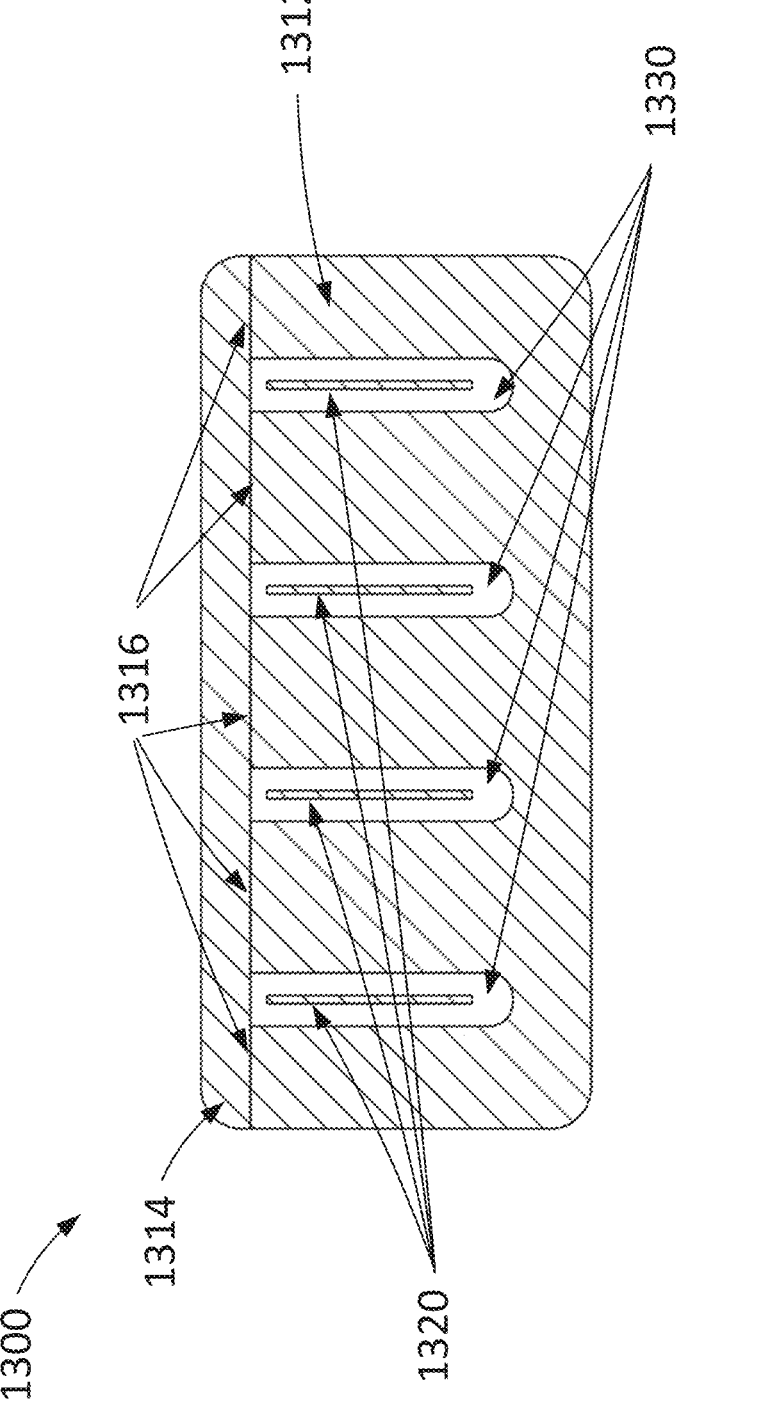

FIG. 20 is a cross-sectional view of the system 1300. FIG. 21 is an enlarged view of the portion A in FIG. 20. FIG. 22 is a cross-sectional view of the system 1300 taken in a plane perpendicular to that of the view of FIG. 20. The system 1300 can be the same or similar in structure and/or function to any of the systems described herein, such as the system 100. For example, the system 1300 includes a housing 1310 defining an inlet 1332, an outlet 1334, and a channel 1330, an elongated ribbon-shaped heating element 1320, a first conductive support member 1340, and a second conductive support member 1342. The housing 1310 can have a first portion 1312 formed as a clamshell defining the fluid channel 1330 and a second portion 1314 forming a lid or cap. The fluid channel 1330 can have a rectangular cross-section with fillets in two corners. The first portion 1312 and the second portion 1314 can be coupled via a seal 1316. The seal 1316 can be disposed around the perimeter and between consecutive passes of the heating element 1320.

Figure 23:
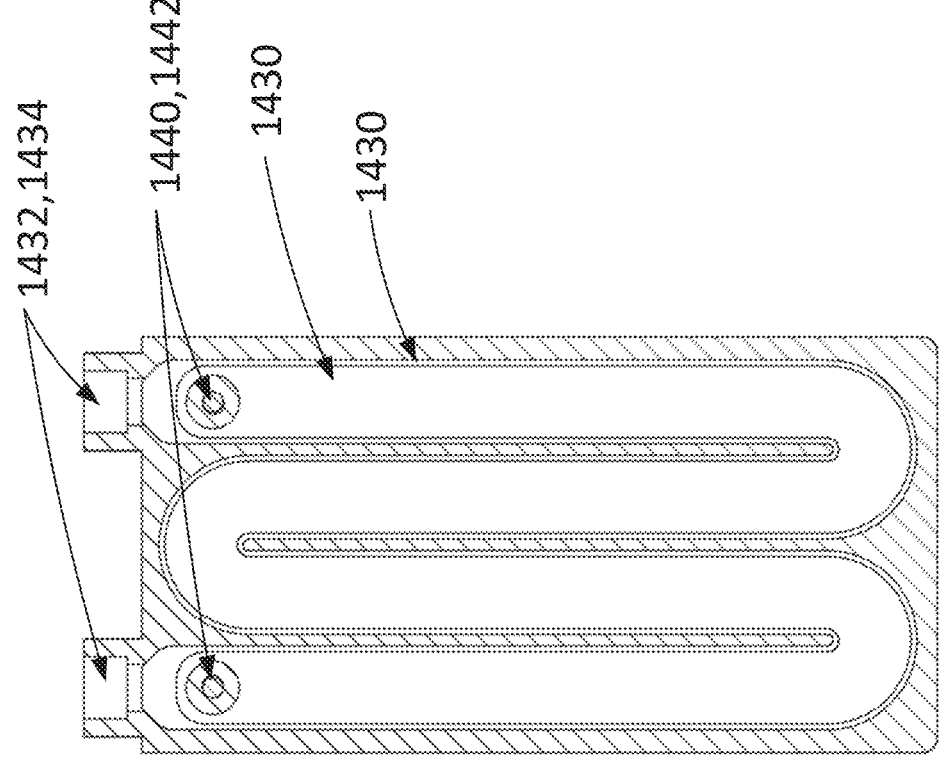
FIGS. 23 and 24 are various views of a fluid warmer system, according to an embodiment.
Figure 24:
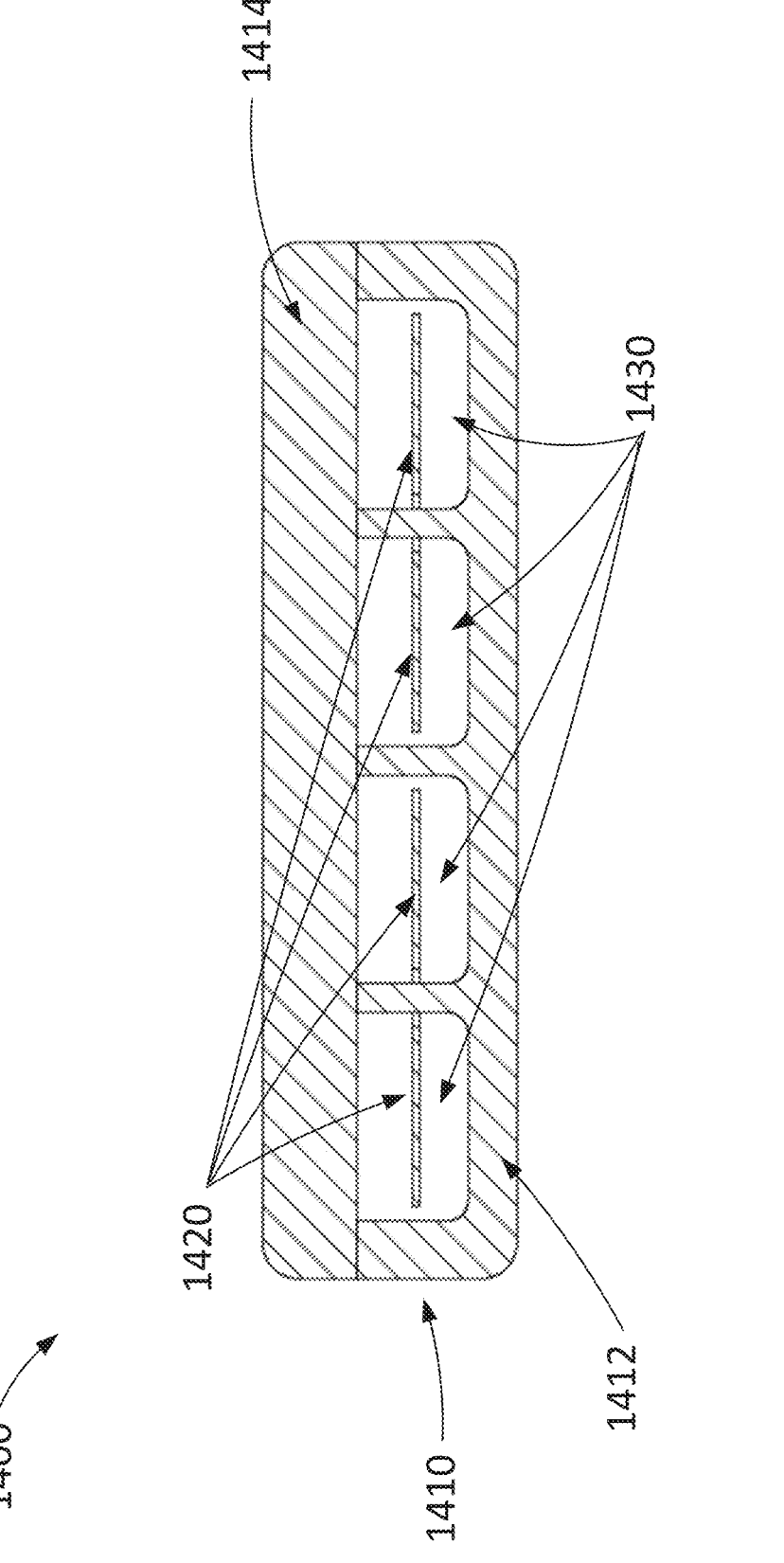

FIG. 23 is a cross-sectional view of the system 1400. FIG. 24 is a cross-sectional view of the system 1400 taken in a plane perpendicular to that of the view of FIG. 23. The system 1400 can be the same or similar in structure and/or function to any of the systems described herein, such as the system 100. For example, the system 1400 includes a housing 1410 defining an inlet 1432, an outlet 1434, and a channel 1430, an elongated, planar flat ribbon-shaped heating element 1420, a first conductive support member 1440, and a second conductive support member 1442. The housing 1410 can have a first portion 1412 formed as a clamshell defining the fluid channel 1430 and a second portion 1414 forming a lid or cap. The fluid channel 1430 can have a rectangular cross-section with fillets in two corners. The first portion 1412 and the second portion 1414 can be coupled via a seal (not shown) that can be disposed around the perimeter and between consecutive passes of the heating element 1420.

Figures 25, 26:
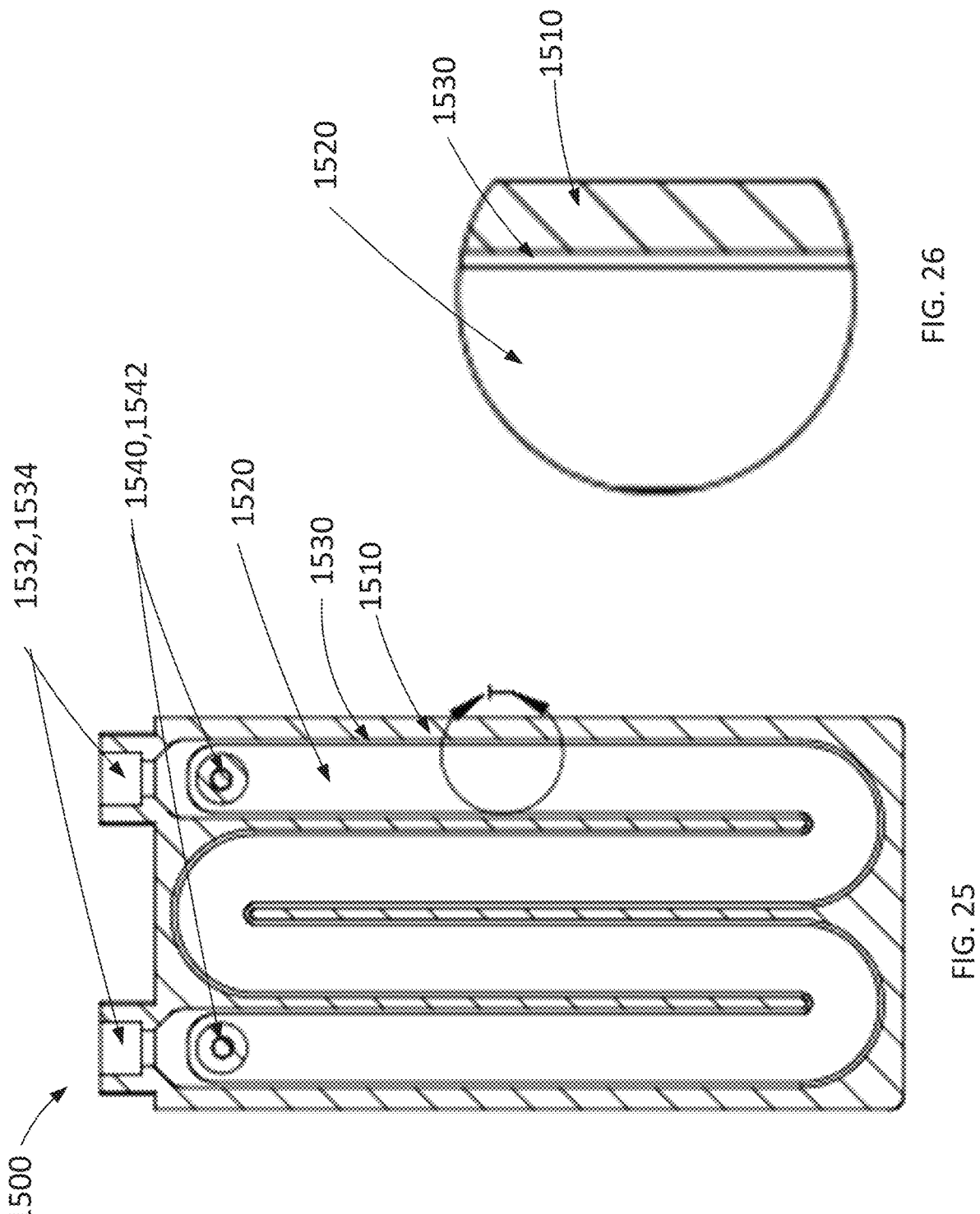
FIGS. 25-27 are various views of a fluid warmer system, according to an embodiment.
Figure 27:
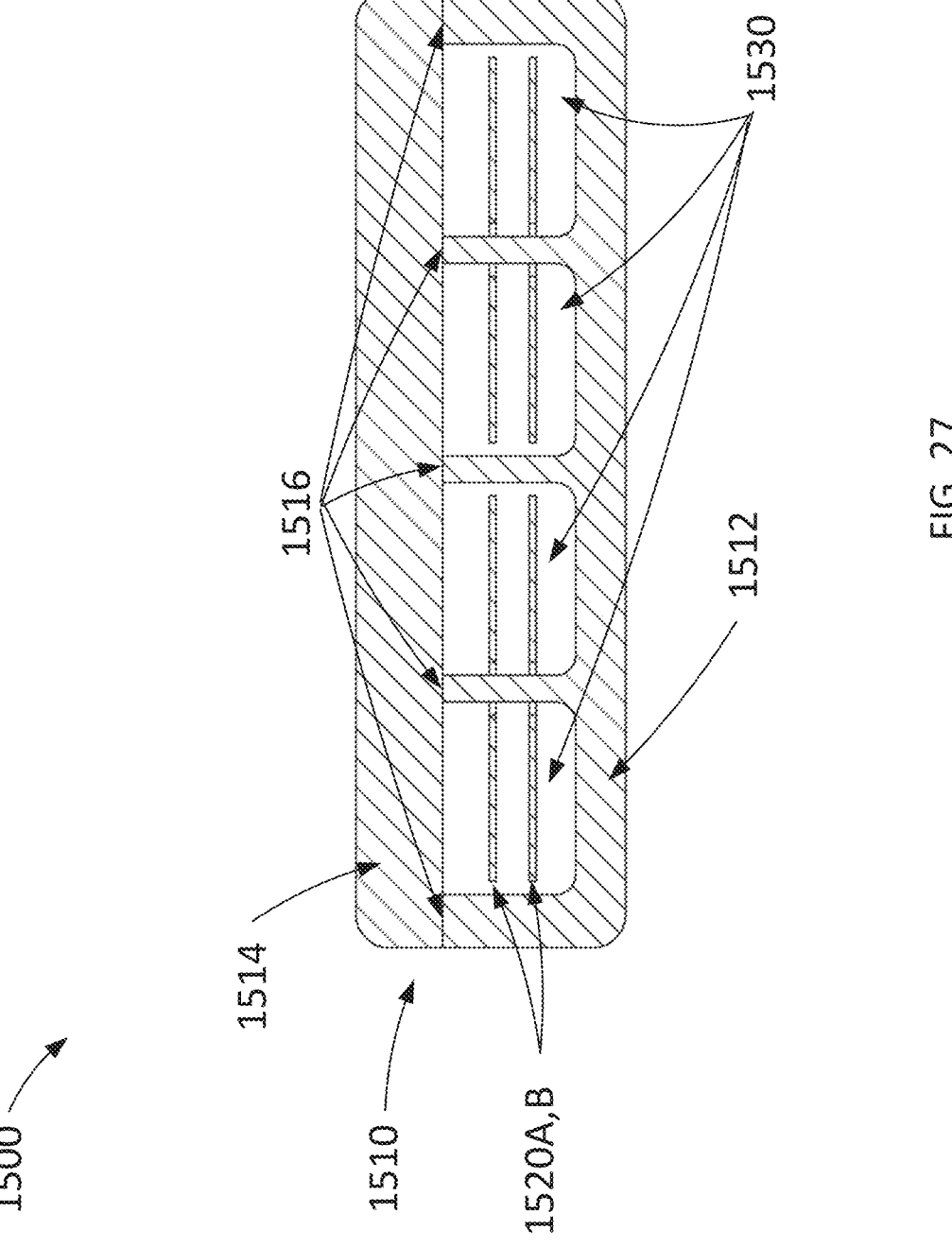

FIG. 25 is a cross-sectional view of the system 1500. FIG. 26 is an enlarged view of the portion A in FIG. 25. FIG. 27 is a cross-sectional view of the system 1500 taken in a plane perpendicular to that of the view of FIG. 25. The system 1500 can be the same or similar in structure and/or function to any of the systems described herein, such as the system 100. For example, the system 1500 includes a housing 1510 defining an inlet 1532, an outlet 1534, and a channel 1530, a first elongated, planar flat ribbon-shaped heating element 1520A, a second elongated, planar flat ribbon-shaped heating element 1520B, a first conductive support member 1540, and a second conductive support member 1542. The housing 1510 can have a first portion 1512 formed as a clamshell defining the fluid channel 1530 and a second portion 1514 forming a lid or cap. The fluid channel 1530 can have a rectangular cross-section with fillets in two corners. The first portion 1512 and the second portion 1514 can be coupled via a seal (not shown) that can be disposed around the perimeter and between consecutive passes of the heating element 1520.

Figure 28:
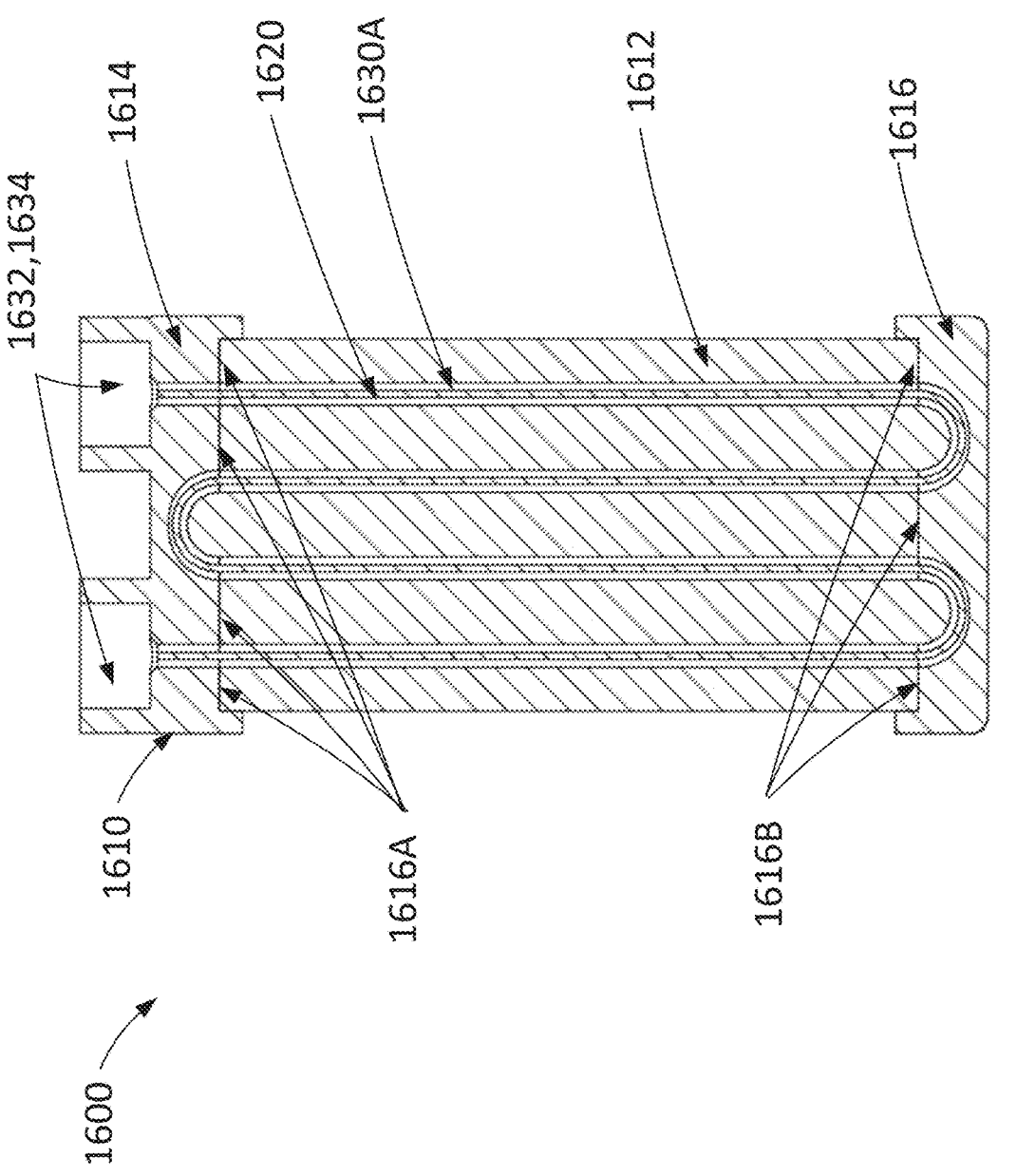
FIGS. 28-30 are various views of a fluid warmer system, according to an embodiment.
Figure 29:
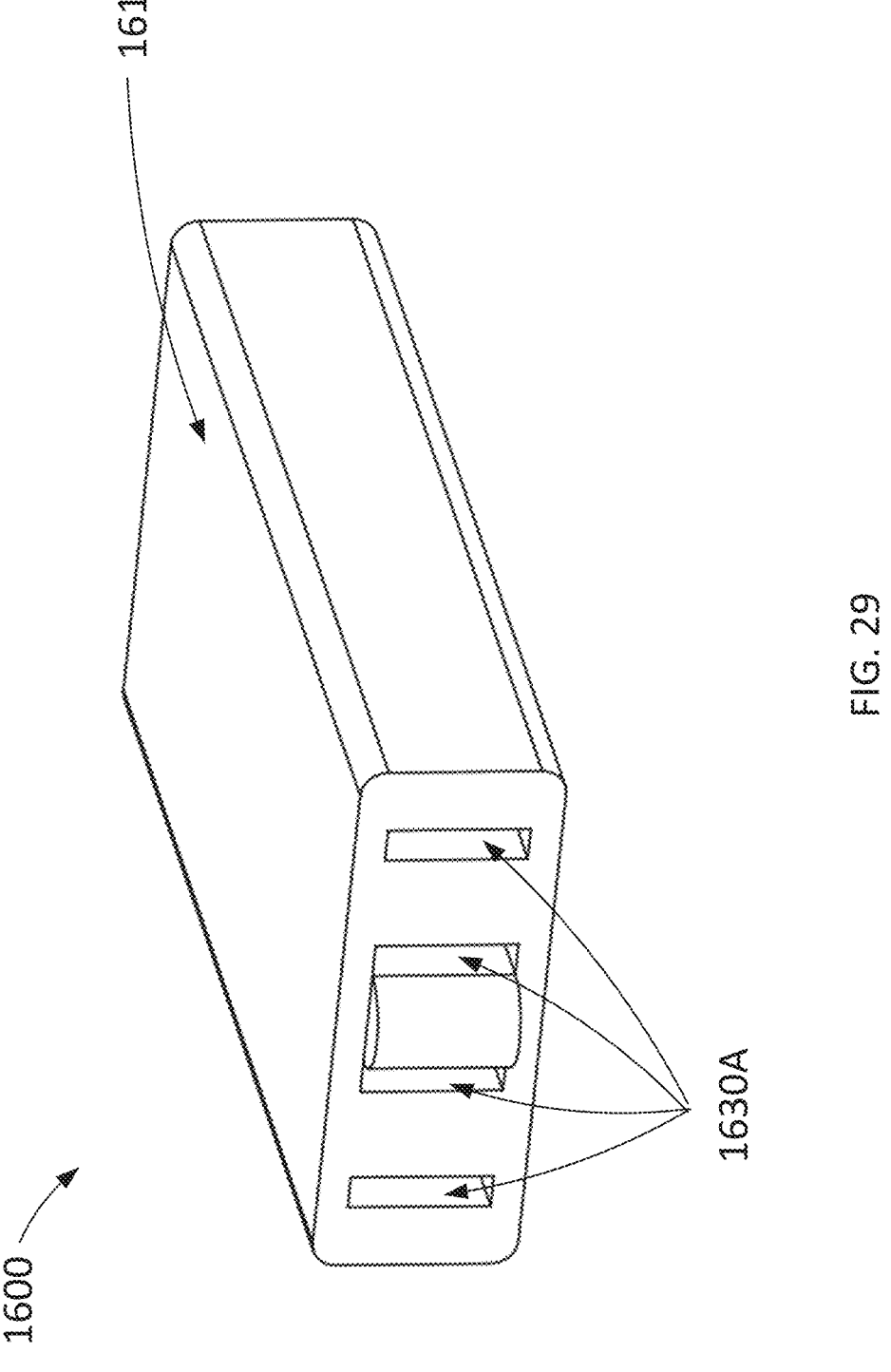
Figure 30:
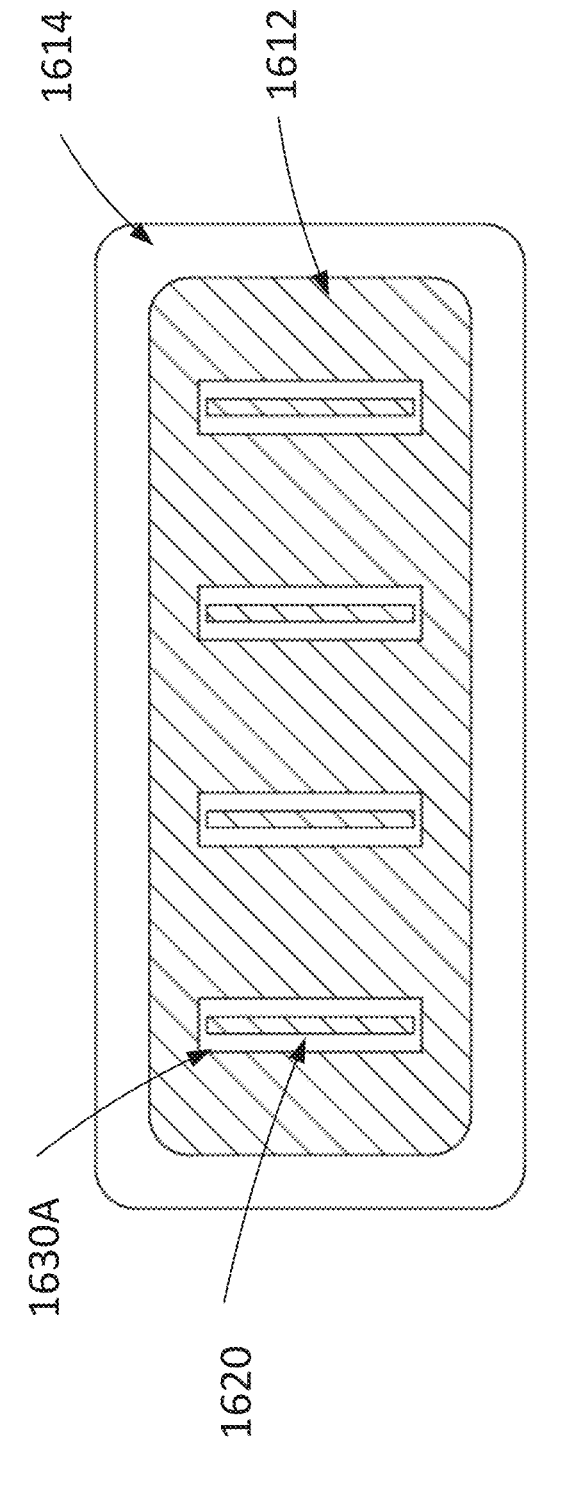

FIG. 28 is a cross-sectional view of a system 1600. FIG. 29 is a perspective view of a first portion 1612 of a housing 1610 of the system 1600. FIG. 30 is a cross-sectional view of the system 1600 taken in a plane perpendicular to that of the view of FIG. 28. The system 1600 can be the same or similar in structure and/or function to any of the systems described herein, such as the system 100. For example, the system 1600 includes the housing 1610 defining an inlet 1632, an outlet 1634, and a channel 1630, an elongated ribbon-shaped heating element 1620, a first conductive support member 1640, and a second conductive support member 1642. The housing 1610 can have a first portion 1612 (also referred to as a central housing) defining a set of straight fluid pathways 1630A (e.g., four) traversing the length of the first portion 1612, a first end cap 1614, and a second end cap 1616. The first portion 1612 can be, for example, extruded. Each of the first end cap 1614 and the second end cap 1616 can define curved fluid pathways with 180 degree turns and can be configured to be coupled to the ends of the first portion 1612 such that the straight fluid pathways 1630A are each aligned with and fluidically coupled to a curved fluid pathway on each end. The system 1600 can includes seals that can be disposed around the perimeter and between consecutive passes of the heating element 1620. For example, the first portion 1612 and the first end cap 1614 can be coupled via a seal 1616A and the second end cap 1616 can be coupled via a seal 1616B.

Figure 31:
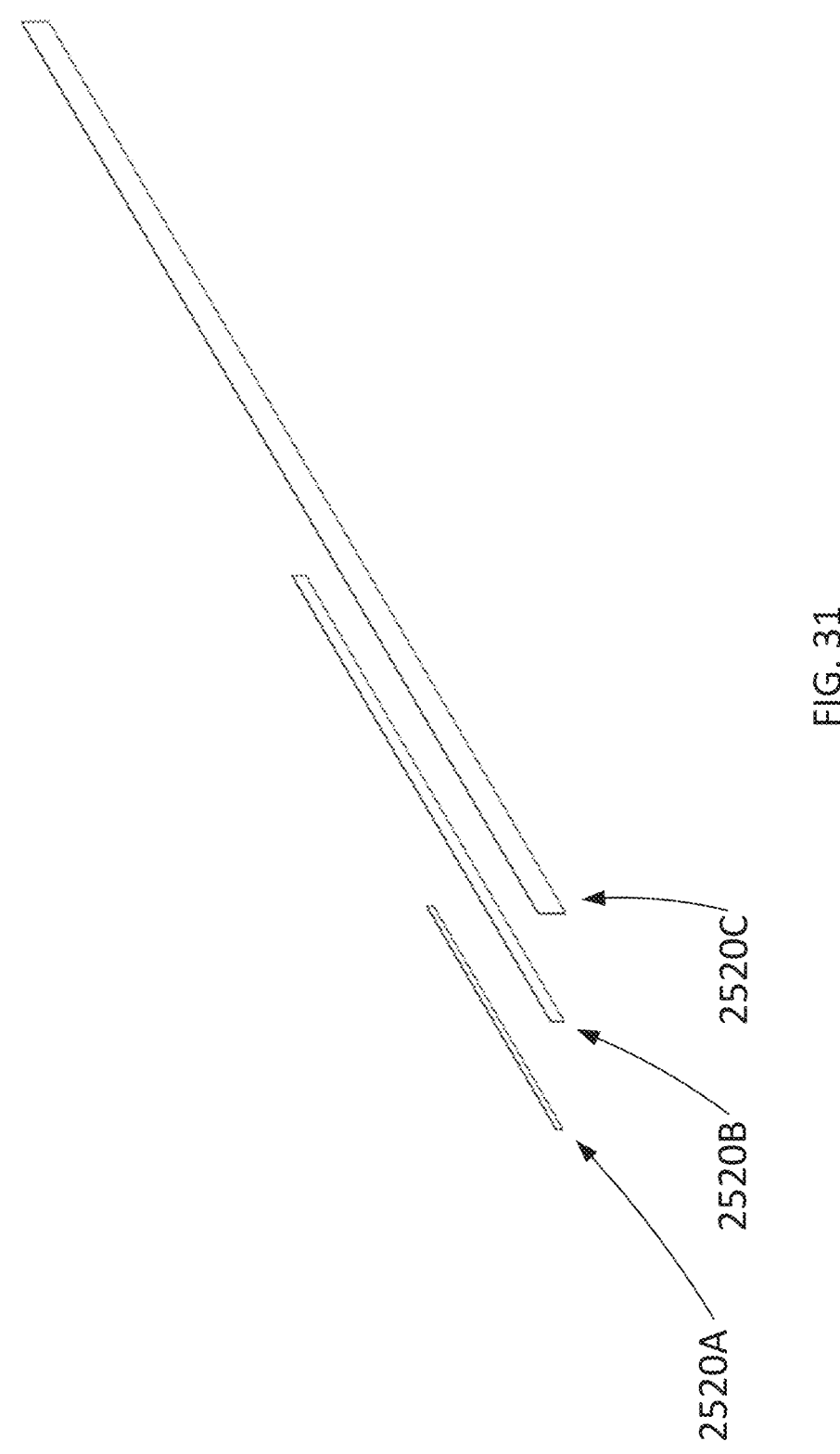
FIGS. 31 and 32 are perspective and front views, respectively, of a first heating element, a second heating element, and a third heating element, according to some embodiments.
Figure 32:
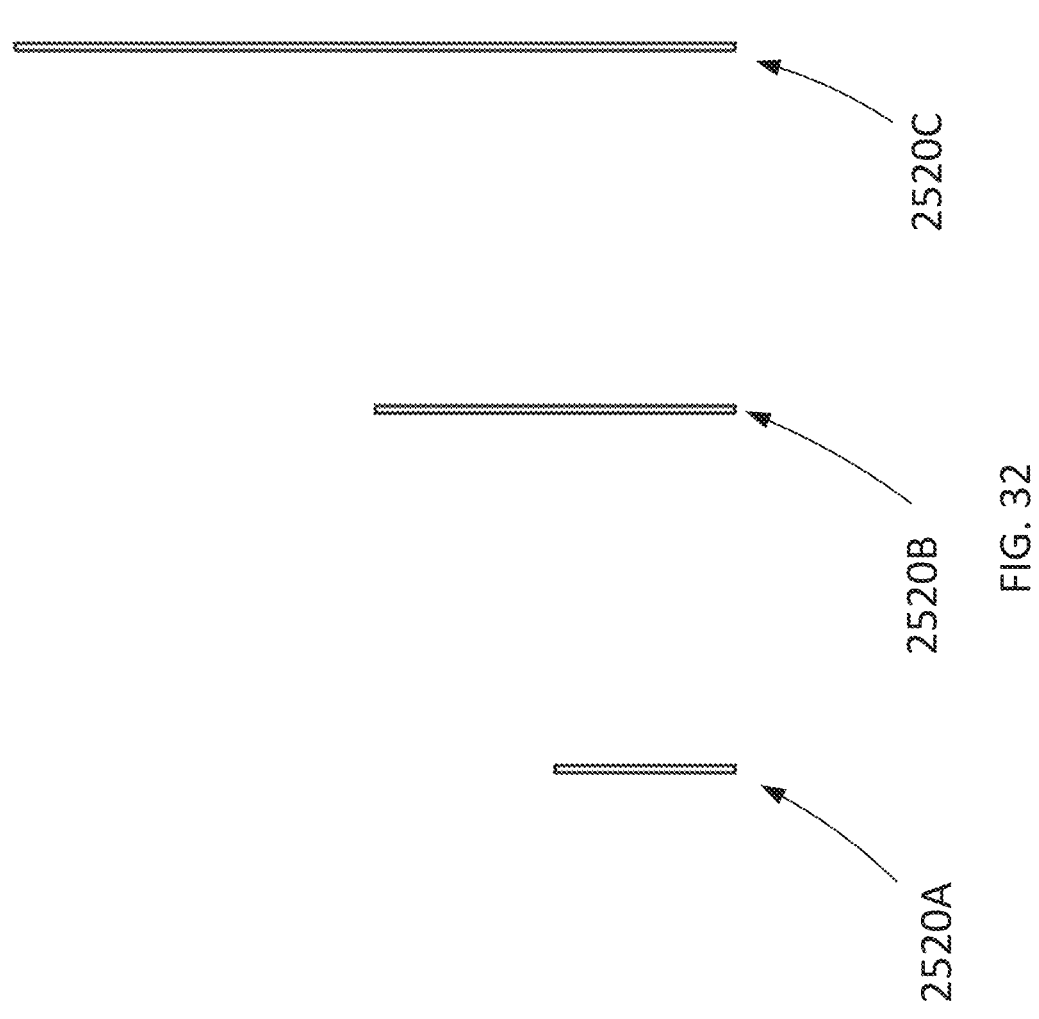

FIGS. 31 and 32 are perspective and front views, respectively, of a first heating element 2520A, a second heating element 2520B, and a third heating element 2520C. Each of the first heating element 2520A, the second heating element 2520B, and the third heating element 2520C have equivalent resistance. Each of the first heating element 2520A, the second heating element 2520B, and the third heating element 2520C have the same thickness and are made of the same material. The second heating element 2520B has twice the height and twice the length of the first heating element 2520A. The third heating element 2520C has twice the length and twice the height of the second heating element 2520B. While each of the first heating element 2520A, the second heating element 2520B, and the third heating element 2520C have the same resistance, the second heating element 2520B has four times the surface area as the first heating element 2520A and the third heating element 2520C has sixteen times the surface area of the first heating element 2520A.

Figure 33:
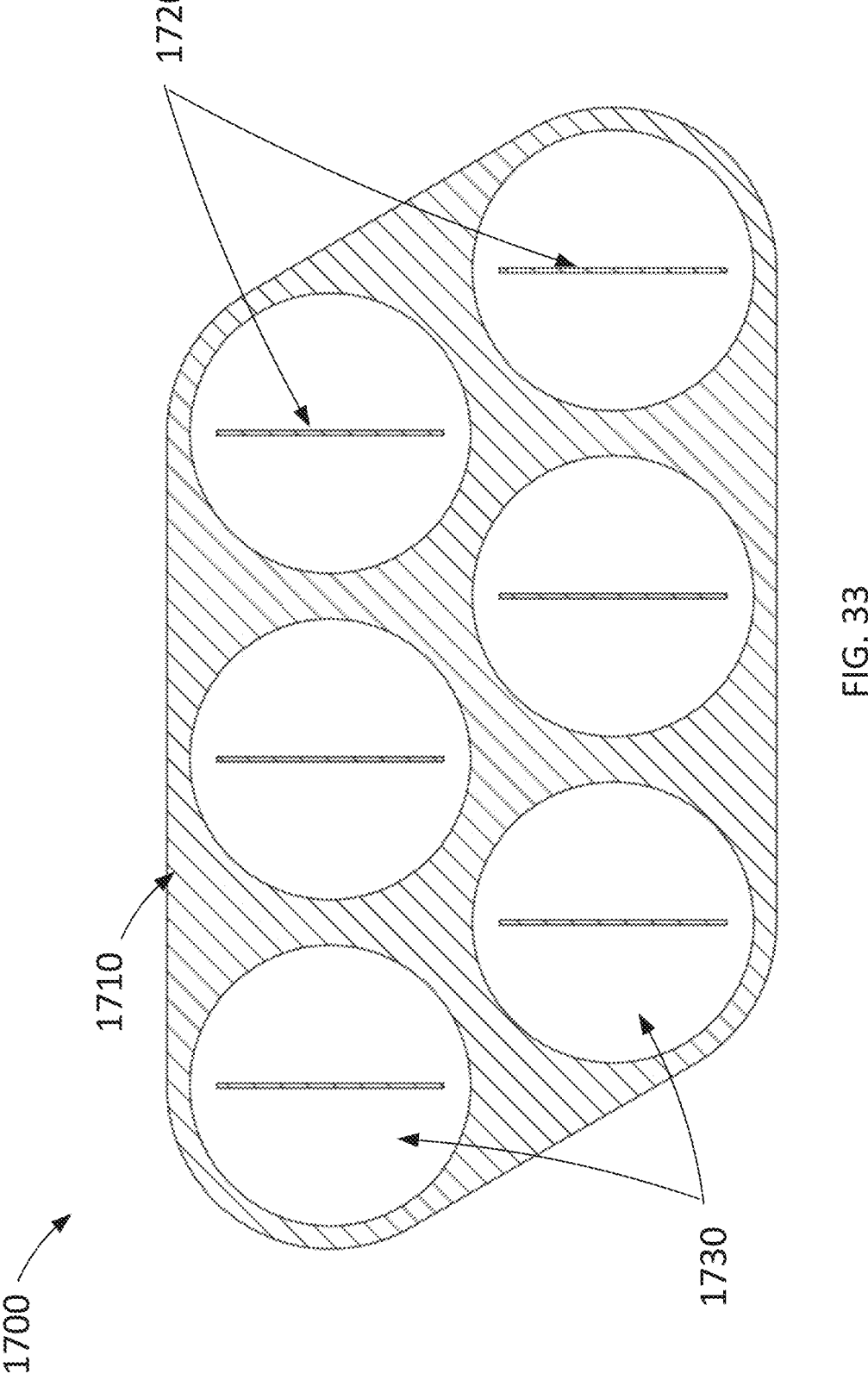
FIG. 33 is a cross-sectional illustration of portion of a fluid warmer system, according to an embodiment.
Figure 34:
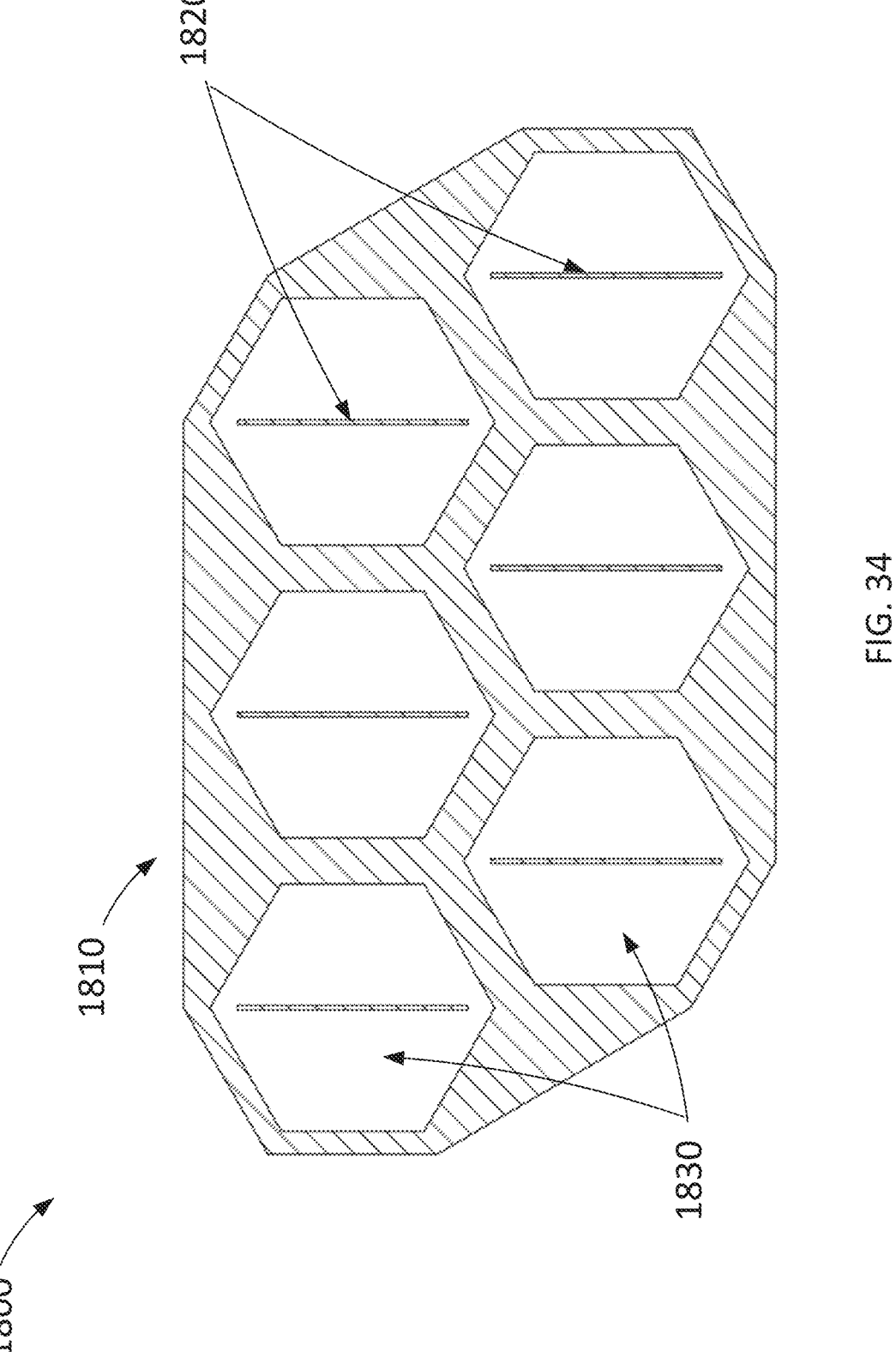
FIG. 34 is a cross-sectional illustration of portion of a fluid warmer system, according to an embodiment.

FIGS. 33 and 34 are cross-sectional views of a system 1700 and a system 1800, respectively. Each of the system 1700 and the system 1800 can be the same or similar in structure and/or function to any of the systems described herein. As shown in FIG. 33, the system 1700 includes a housing 1710 defining a fluid channel 1730 having a circular cross-section and an elongated heating element 1720. As shown in FIG. 34, the system 1800 includes a housing 1810 defining a fluid channel 1830 having a hexagonal cross-section and an elongated heating element 1820. In both the system 1700 and the system 1800, the fluid channels 1730, 1830 and the elongated heating elements 1820, 1920 can travel through two distinct planes.

Figure 35:
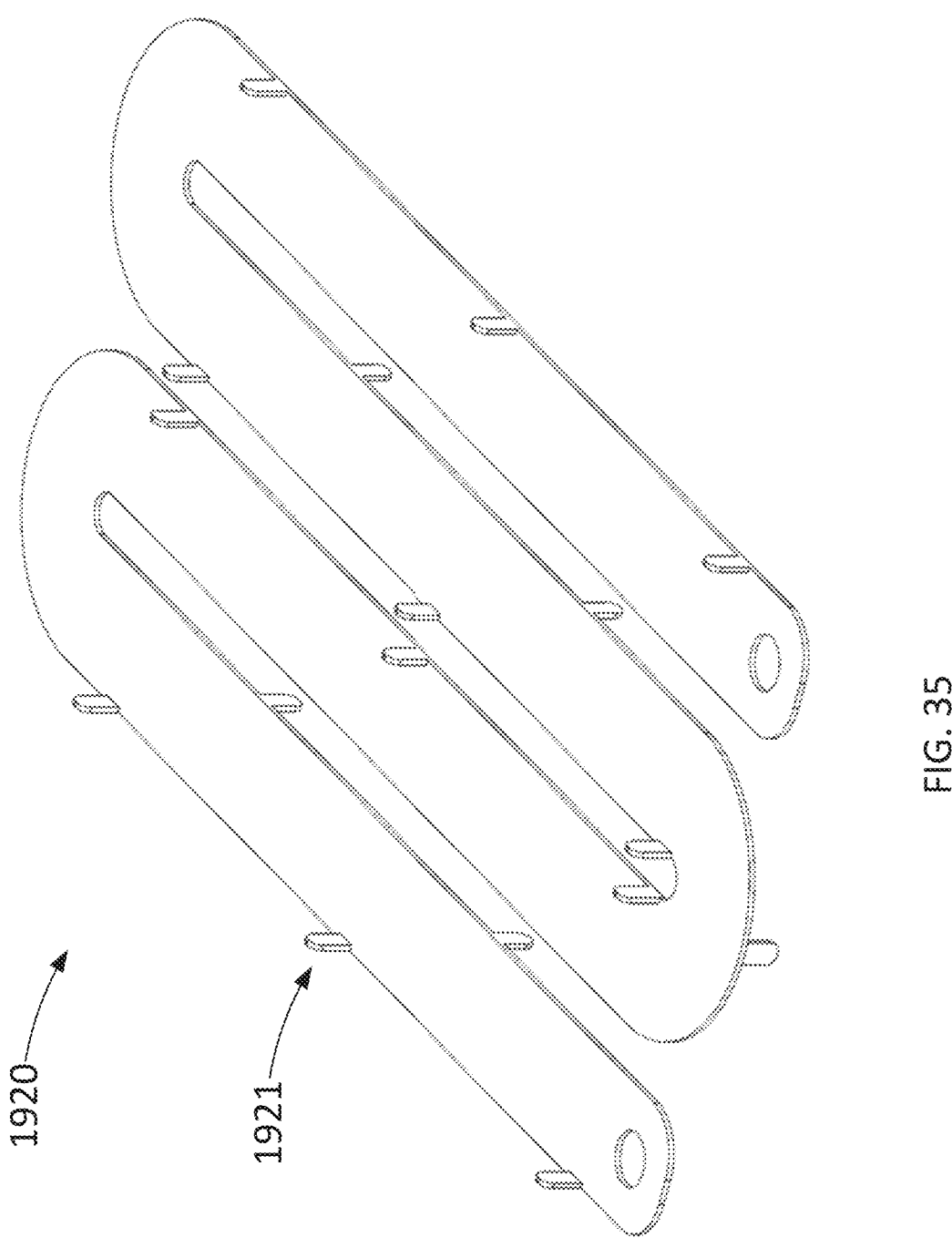
FIGS. 35 and 36 and are various views of a fluid warmer system, according to an embodiment.
Figure 36:
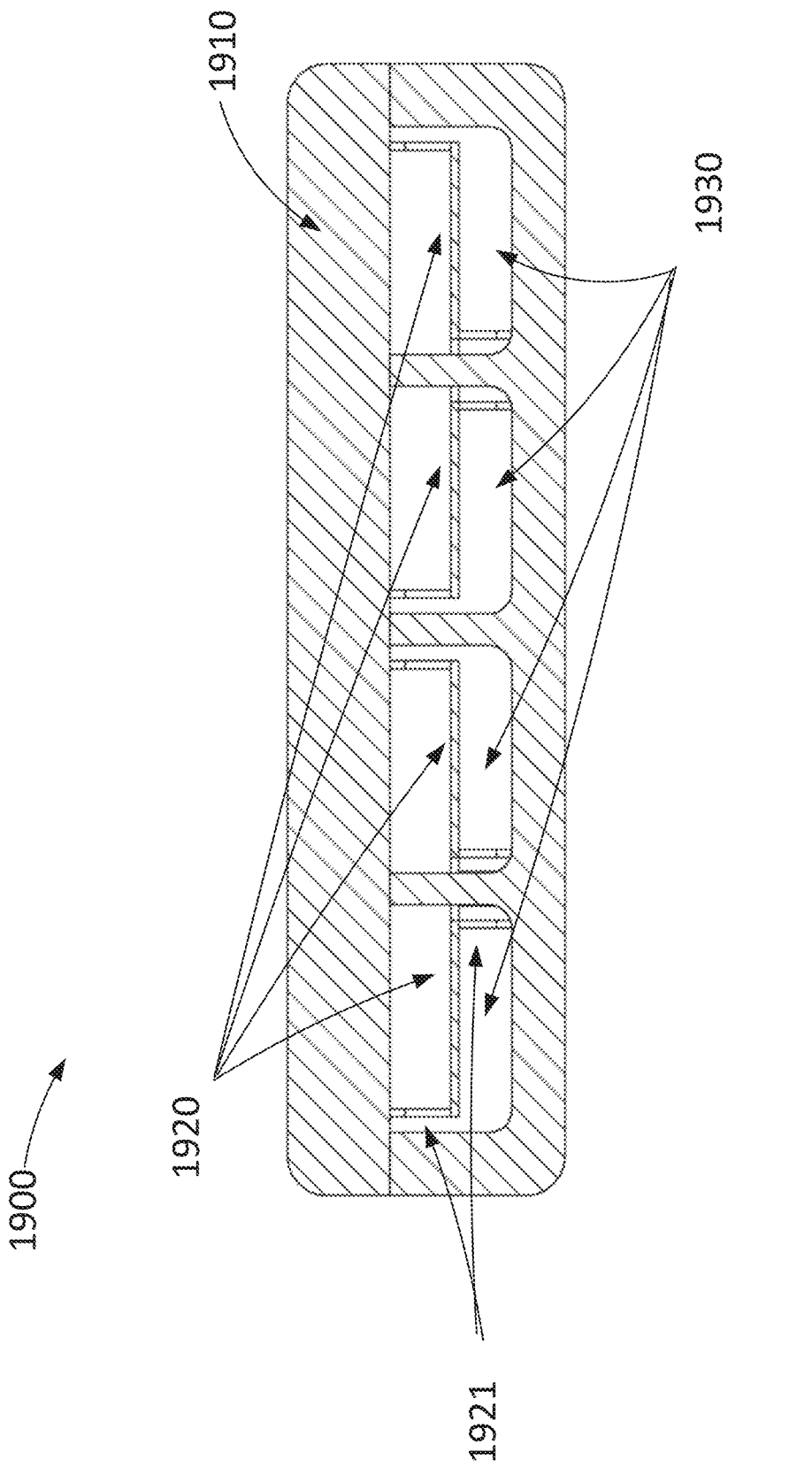

FIG. 35 is a perspective view of a flat ribbon elongated heating element 1920. FIG. 36 is a cross-sectional illustration of a system 1900 including the elongated heating element 1920. The system 1900 can be the same or similar in structure and/or function to any of the systems described herein, such as the system 100. As shown, the elongated member 1920 includes a set of protruding features 1921 that extend perpendicularly to the planar surface of the elongated heating element 1920 and function as locating features for the elongated heating element 1920 within a fluid channel 1930 defined by a housing 1910 of the system 1900. As shown, some of the protruding features 1921 extend in a first direction and some of the protruding features 1921 extend in a second direction opposite the first direction such that fluid can flow through the fluid channel 1930 on both sides of the elongated heating element 1920. The protruding features 1921 can extend in opposite directions in an alternating fashion along the perimeter of the elongated heating element 1920.

Figures 37, 38:
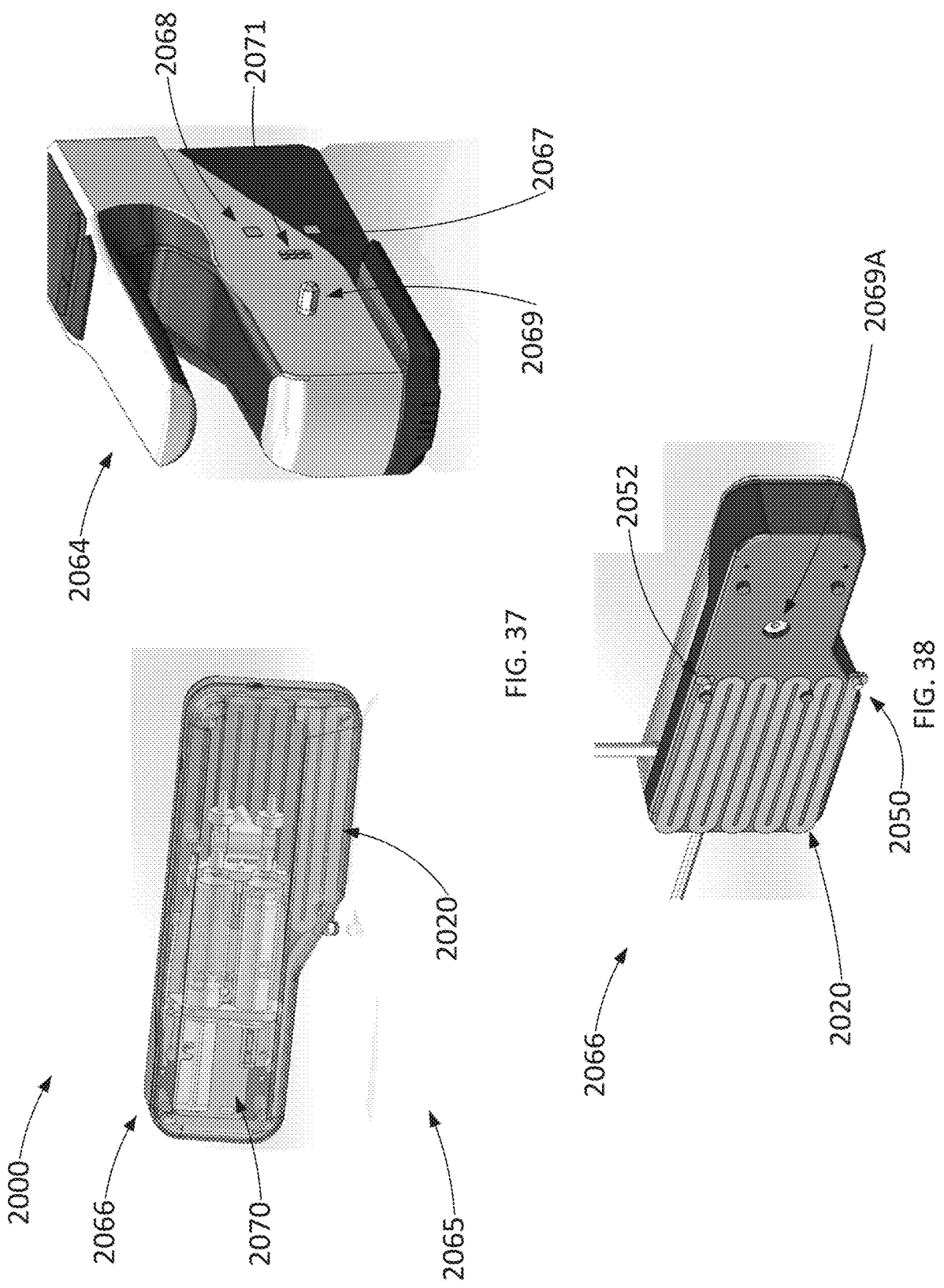
FIGS. 37 and 38 are various views of a fluid warmer system, according to an embodiment.

FIG. 37 is a perspective view of a front side of a disposable portion 2066 and a back side of a reusable drive assembly portion 2064 of an infusion assembly 2065 of a system 2000. FIG. 38 is a perspective view of a back side of the disposable portion 2066. The system 2000 may be the same or similar in structure and/or function to any of the systems described herein. For example, the disposable portion 2066 can be the same or similar in structure and/or function to the disposable portion 166 and the drive assembly portion 2064 can be the same or similar in structure and/or function to the drive assembly portion 164 described above with respect to the system 100. The disposable portion 2066 includes a warmer assembly including a housing (not shown) defining a fluid channel within which an elongated heating element 2020 is disposed. The disposable portion 2066 also includes a fluid pumping assembly 2070 that can be the same or similar in structure and/or function to the fluid pumping assembly 170 and can be fluidically coupled to the fluid channel of the warmer assembly such that fluid flows through the fluid channel of the warmer either prior to being drawn into the fluid pumping assembly 2070 or after being expelled from the fluid pumping assembly 2070. As shown, the warmer assembly also includes a first electrical connector 2050 and a second electrical connector 2052, which can be coupled to or formed to include a first conductive support member (not shown) and a second conductive support member (not shown) coupled to the elongated heating element 2020 to support the elongated heating element 2020 within the fluid channel defined by the housing of the warmer assembly. The drive assembly portion 2064 can include a first electrical contact 2067 and a second electrical contact 2068 configured to be coupled to the first electrical connector 2050 and the second electrical connector 2052, respectively, to provide power to the elongated heating element 120 for warming of fluid when a drive mechanism 2069 of the drive assembly portion 164 is operably engaged with a drive feature 2069A of the disposable portion 2066 to drive the fluid pumping assembly 2070. As shown in FIG. 37, the drive assembly portion 2064 can optionally include one or more additional electrical contacts 2071 (e.g., FIG. 37 shows the drive assembly portion 2064 as including eight electrical contacts 2071) disposed on the drive assembly portion 2064 and configured to be coupled with one or more associated electrical contacts of the disposable portion 2066 (e.g., of the warmer assembly) (not shown) such that data (e.g., operational instructions, operational data, temperature feedback) can be transferred between the drive assembly portion 2064 and the disposable portion 2066 (e.g., the warmer assembly of the disposable portion 2066).

Figure 39:
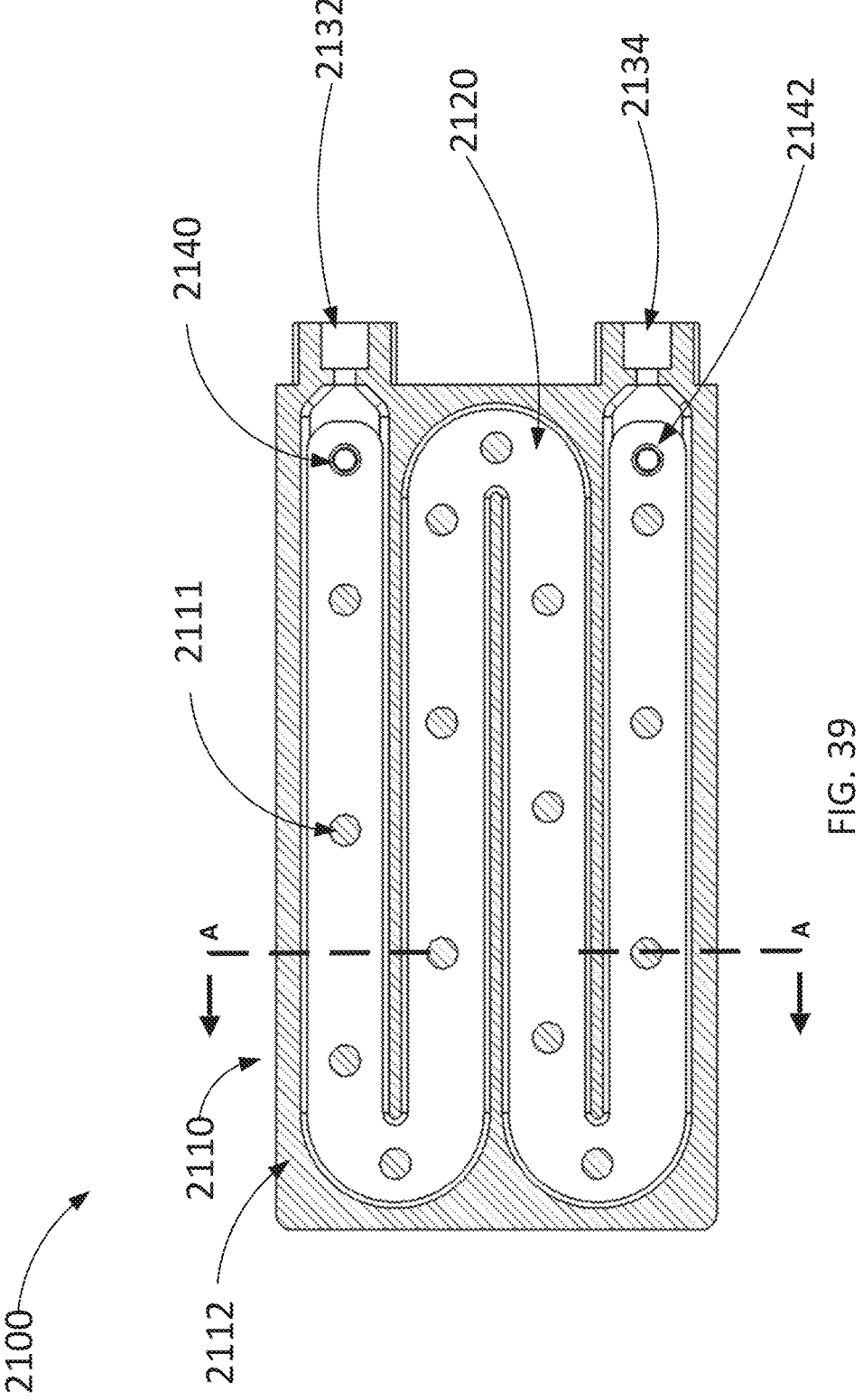
FIGS. 39-40 and are various views of a fluid warmer system, according to an embodiment.
Figure 40:
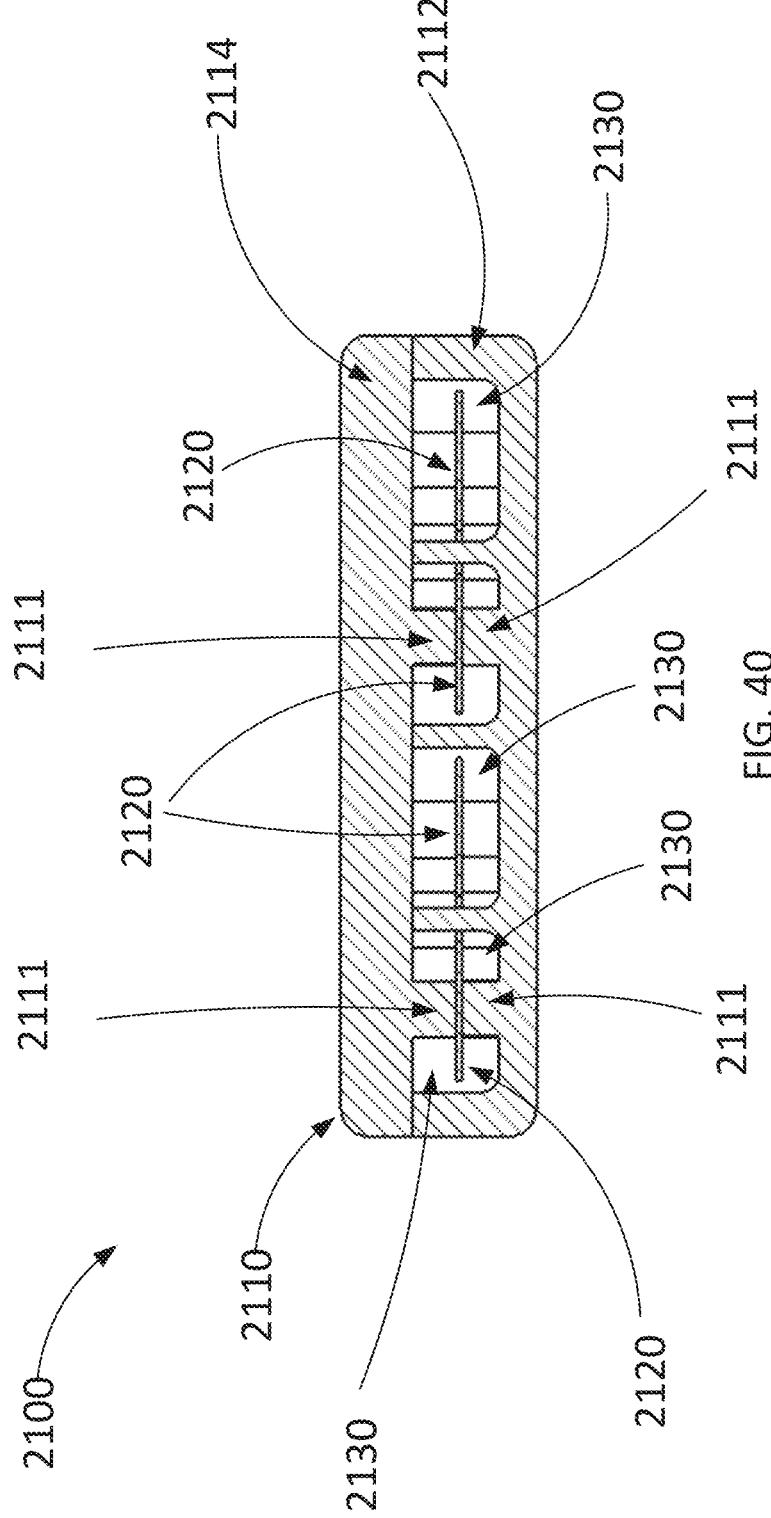

FIG. 39 is a cross-sectional view of a system 2100. FIG. 40 is a cross-sectional view of the system 2100 taken along line A-A in FIG. 39 (in a plane perpendicular to that of the view of FIG. 39). The system 2100 can be the same or similar in structure and/or function to any of the systems described herein, such as the system 100. For example, the system 2100 includes a housing 2110 defining an inlet 2132, an outlet 2134, and a channel 2130, a flat ribbon-shaped elongated heating element 2120, a first conductive support member 2140, and a second conductive support member 2142. The flat ribbon-shaped elongated heating element 2120 can have a rectangular cross-section having a top surface, a bottom surface, and opposing side surfaces. The cross-section of the flat ribbon-shaped elongated heating element 2120 can have a larger width than height due to the top surface and the bottom surface being wider than the side surfaces are tall. The top surface and the bottom surface of the flat ribbon-shaped elongated heating element 2120 can be disposed (e.g., entirely) in parallel planes.

The housing 2110 can be formed of a first portion 2112 and a second portion 2114 sealed together such that the first portion 2112 and the second portion 2114 collectively define the fluid channel 2130. As shown, the housing 2110 includes a set of protruding features 2111 (e.g., bosses) that can be disposed in the fluid channel 2130 to support the elongated heating element 2120 within the fluid channel 2130. For example, each protruding feature can extend away from a channel wall of the housing 2110 toward (e.g., perpendicularly to) the top and bottom surfaces of the elongated heating element 2120 to contact the elongated heating element 2120 and function as locating features for the elongated heating element 2120 within the fluid channel 2130. The protruding features 2111 can be non-conductive. As shown, the protruding features 2111 can extend from channel wall portions both above and below the elongated heating element 2120 (e.g., from both the first portion 2112 and the second portion 2114) such that the elongated heating element 2120 is disposed between the opposing channel wall portions (e.g., equidistant from the opposing upper and lower channel wall portions and/or equidistance from opposing sidewalls of the channel 2130). Thus, each of the protruding features 2111 can be disposed on an opposite side of the elongated heating element 2120 from another protruding feature 2111 (e.g., coaxially with the other protruding feature 2111) to collectively pinch the elongated heating element 2120 between the pair of protruding features 2111 and hold the elongated heating element 2120 in place (e.g., such that the elongated heating element 2120 does not directly contact any of the channel walls defining the fluid channel 2130). Although FIG. 29 shows fifteen protruding features 2111 on a first side of the elongated heating element 2120 (and, thus, thirty protruding features total), the system 2100 can include any suitable number of protruding features 2111. Additionally, in some embodiments, one or more of the protruding features 2111 may be arranged so that it is not coaxially disposed in a pair with another protruding feature 2111 on the opposite side of the elongated heating element 2120, and may instead be offset from the protruding features 2111 supporting the opposite side of the elongated heating element 2120. Although the protruding features 2111 are shown as having a cylindrical shape, the protruding features 2111 can formed in any suitable shape.

Figure 41:
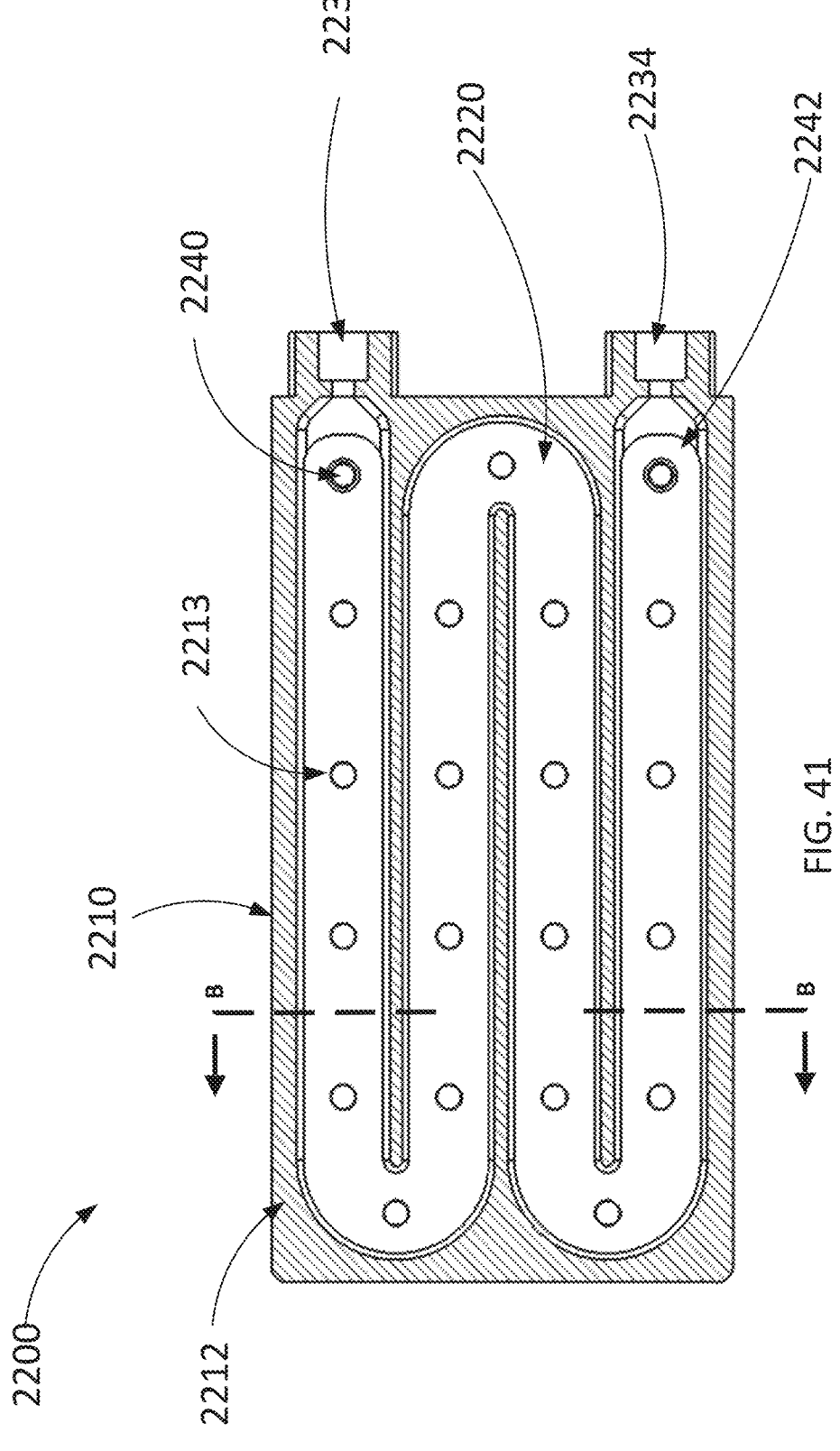
FIGS. 41-42 and are various views of a fluid warmer system, according to an embodiment.
Figure 42:
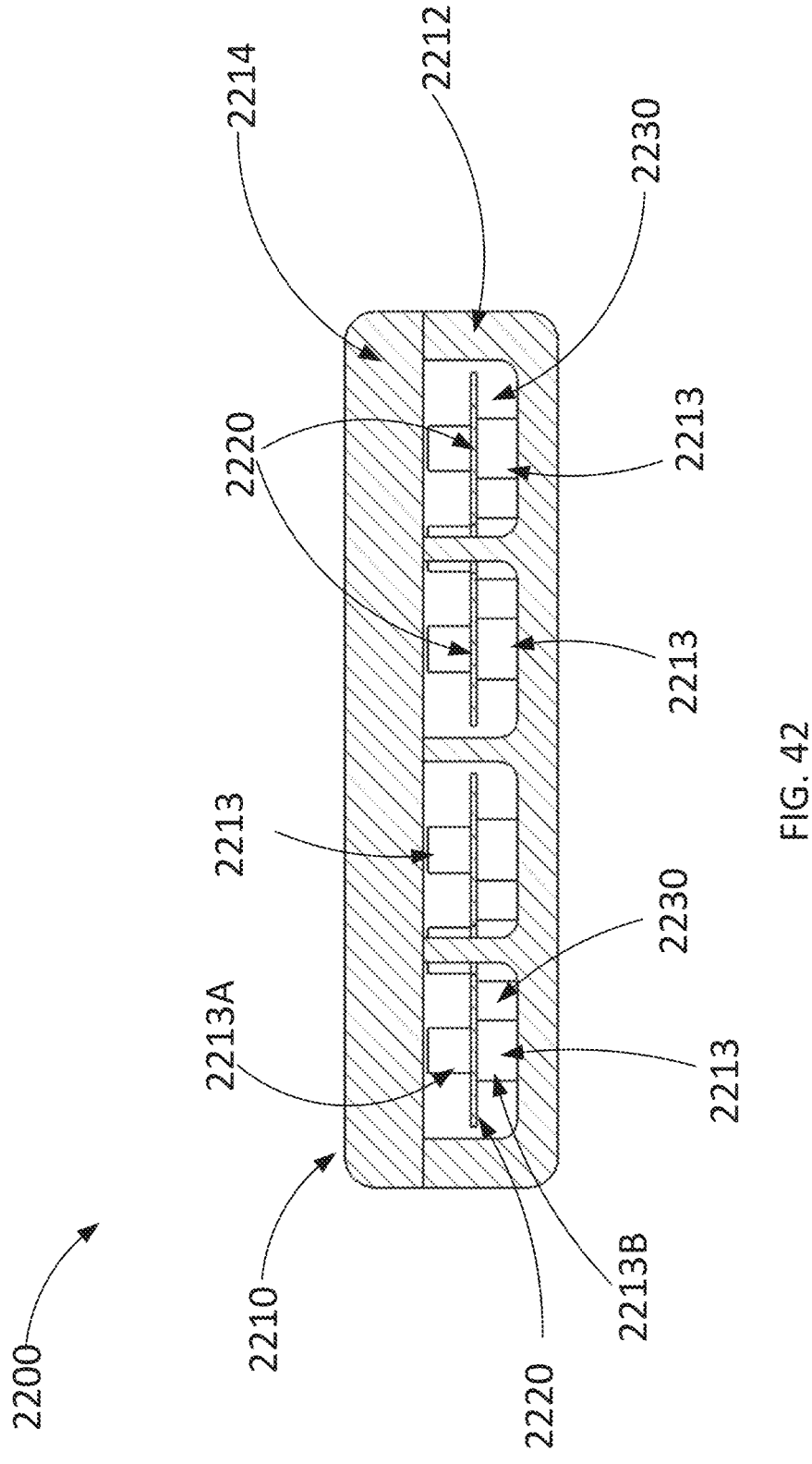

In some embodiments, rather than including protruding features that pinch an elongated heating element from opposite sides, protruding features can extend through openings in the elongated heating element and supportively engage with the elongated heating element adjacent the openings. For example, FIG. 41 is a top view of a system 2200. FIG. 42 is a cross-sectional view of the system 2200 taken along line B-B in FIG. 41. The system 2200 can be the same or similar in structure and/or function to any of the systems described herein, such as the system 100. For example, the system 2200 includes a housing 2210 defining an inlet 2232, an outlet 2234, and a channel 2230, a flat ribbon-shaped elongated heating element 2220, a first conductive support member 2240, and a second conductive support member 2242. The flat ribbon-shaped elongated heating element 2220 can have a rectangular cross-section having a top surface, a bottom surface, and opposing side surfaces. The cross-section of the flat ribbon-shaped elongated heating element 2220 can have a larger width than height due to the top surface and the bottom surface being wider than the side surfaces are tall. The top surface and the bottom surface of the flat ribbon-shaped elongated heating element 2220 can be disposed (e.g., entirely) in parallel planes. The elongated heating element 2220 can also define a set of holes extending from the top surface to the bottom surface.

The housing 2210 can be formed of a first portion 2212 and a second portion 2214 sealed together such that the first portion 2212 and the second portion 2214 collectively define the fluid channel 2230. As shown, the housing 2210 includes a set of protruding features 2213 (e.g., bosses) that can be disposed in the fluid channel 2130 and can extend (e.g., perpendicularly) through the holes defined in the elongated heating element 2220 to engage with and support the elongated heating element 2220 within the fluid channel 2230. As shown, the protruding features 2213 include a narrow portion 2213A and a wide portion 2213B. The narrow portion 2213A can have a diameter that is smaller than the diameter of an associated opening in the elongated heating element 2220 and the wider portion 2213B can have a diameter that is larger than the diameter of the associated opening in the elongated heating element 2220 such that the narrow portion can be passed through the opening and the elongated heating element 2220 sits on the wide portion 2213B and supports the elongated heating element 2220 within the fluid channel 2230 (e.g., equidistant from the opposing upper and lower channel wall portions and/or equidistance from opposing sidewalls of the channel 2230). The protruding features 2213 can be non-conductive. As shown in FIG. 42, in some embodiments, the protruding features 2213 can extend from only one side (e.g., from the first portion 2212) of the elongated heating element 2220. The protruding features 2213 can optionally contact the opposite channel wall (e.g., of the second portion 2214). In some embodiments, protruding features 2213 can extend from both the first portion 2212 and the second portion 2214 such that some engage the first side of the elongated heating element 2220 and some engage the second side of the elongated heating element 2220. In some embodiments, one or more of the protruding features 2213 can include a retaining feature (e.g., a bump, ridge, tab, larger diameter portion) extending from the narrow portion 2213A and configured to contact and retain the elongated heating element 2220 against the wider portion 2213B. In some embodiments, a system can include a combination of the protruding features 2111 and the protruding features 2213.

Figure 43:
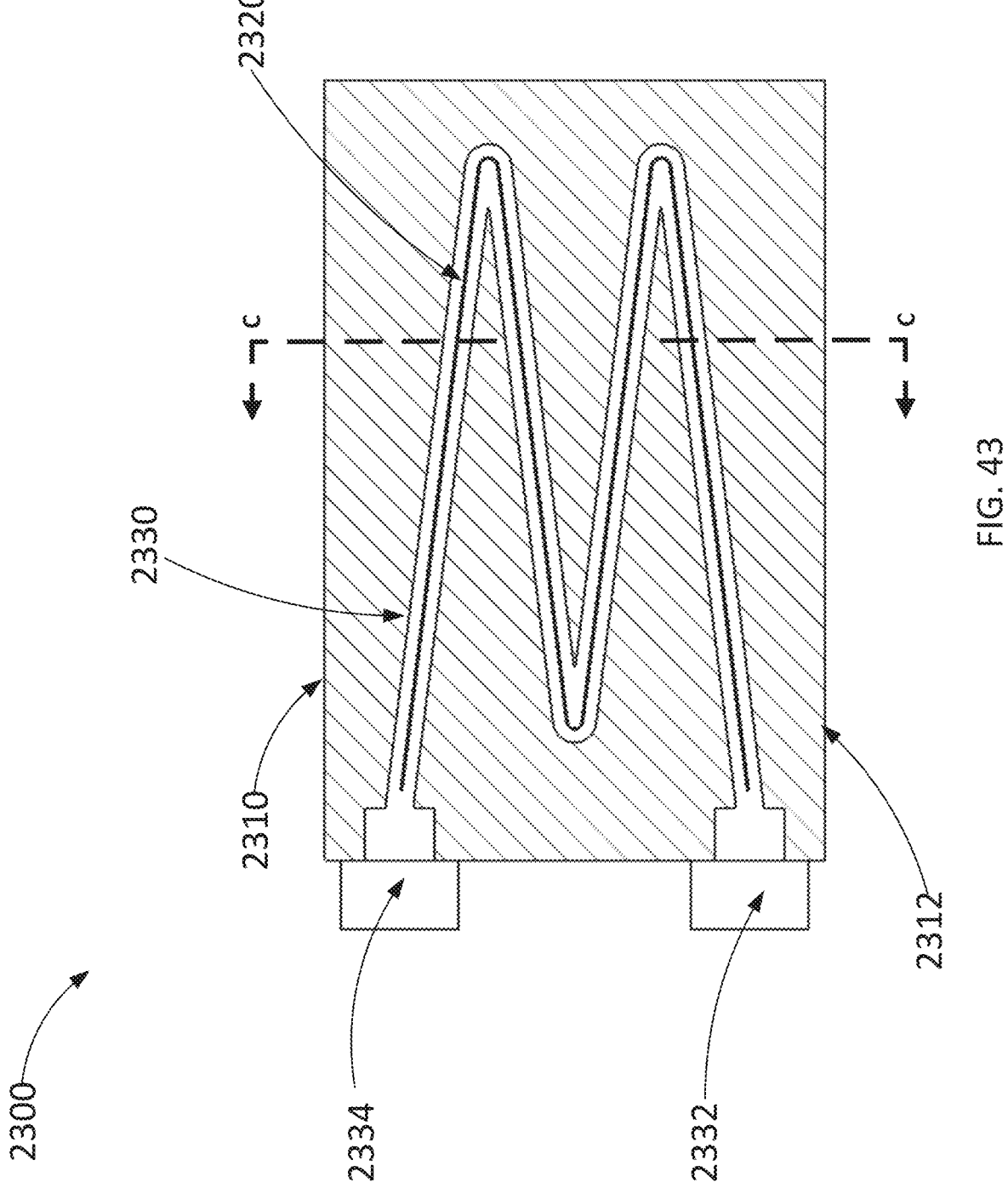
FIGS. 43-44 and are various views of a fluid warmer system, according to an embodiment.
Figure 44:
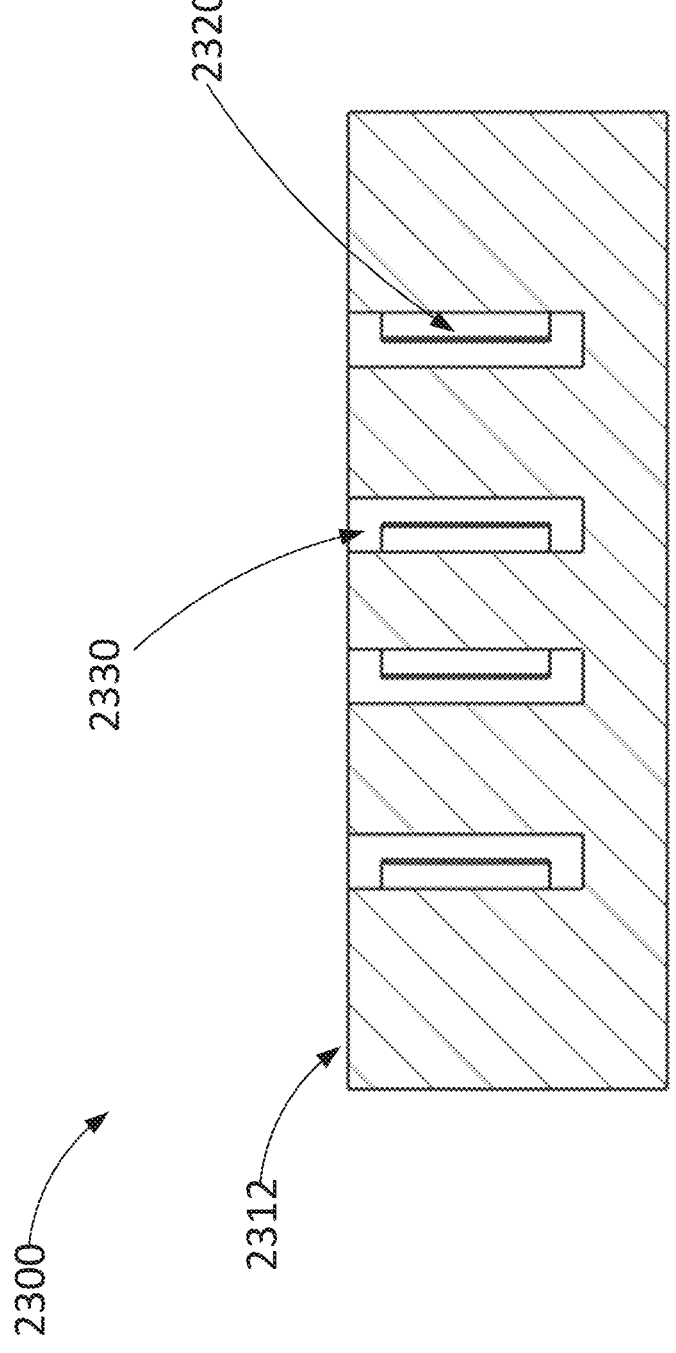

FIG. 43 is a cross-sectional illustration of a system 2300. FIG. 44 is a cross-sectional view of the system 2300 taken along line C-C in FIG. 43. The system 2300 can be the same or similar in structure and/or function to any of the systems described herein, such as the system 100. For example, the system 2300 includes a housing 2310 defining an inlet 2332, an outlet 2334, and a zig-zag-shaped elongated heating element 2320. The housing 2310 can be formed of a first portion 2312 and a second portion (not shown) sealed together such that the first portion 2312 and the second portion collectively define the fluid channel 2330. The system 2300 can be configured such that, when the system 2300 is in an upright position in which the inlet 2332 is disposed below the outlet 2334, fluid can be introduced into the inlet 2332 and through the fluid channel 2330 to force air within the fluid channel 2330 upward and out of the outlet 2334. In some embodiments, an accelerometer (not shown) can also be included in the system 2300 (e.g., coupled to the housing 2310 directly or indirectly) and can be configured to sense an orientation of the housing 2310 (e.g., whether the system 2300 is in an upright orientation). The system 2300 (e.g., a controller of the system 2300 associated with delivery of fluid from a fluid source, such as the controller 161) can be configured to allow priming of the fluid channel 2330 and/or infusion through the fluid channel 2330 if the housing 2310 is in the upright orientation or within a particular range of the upright orientation and to not allow and/or stop priming and/or infusion if the system 2300 is not in the upright orientation or within a particular range of the upright orientation.

Figure 45:
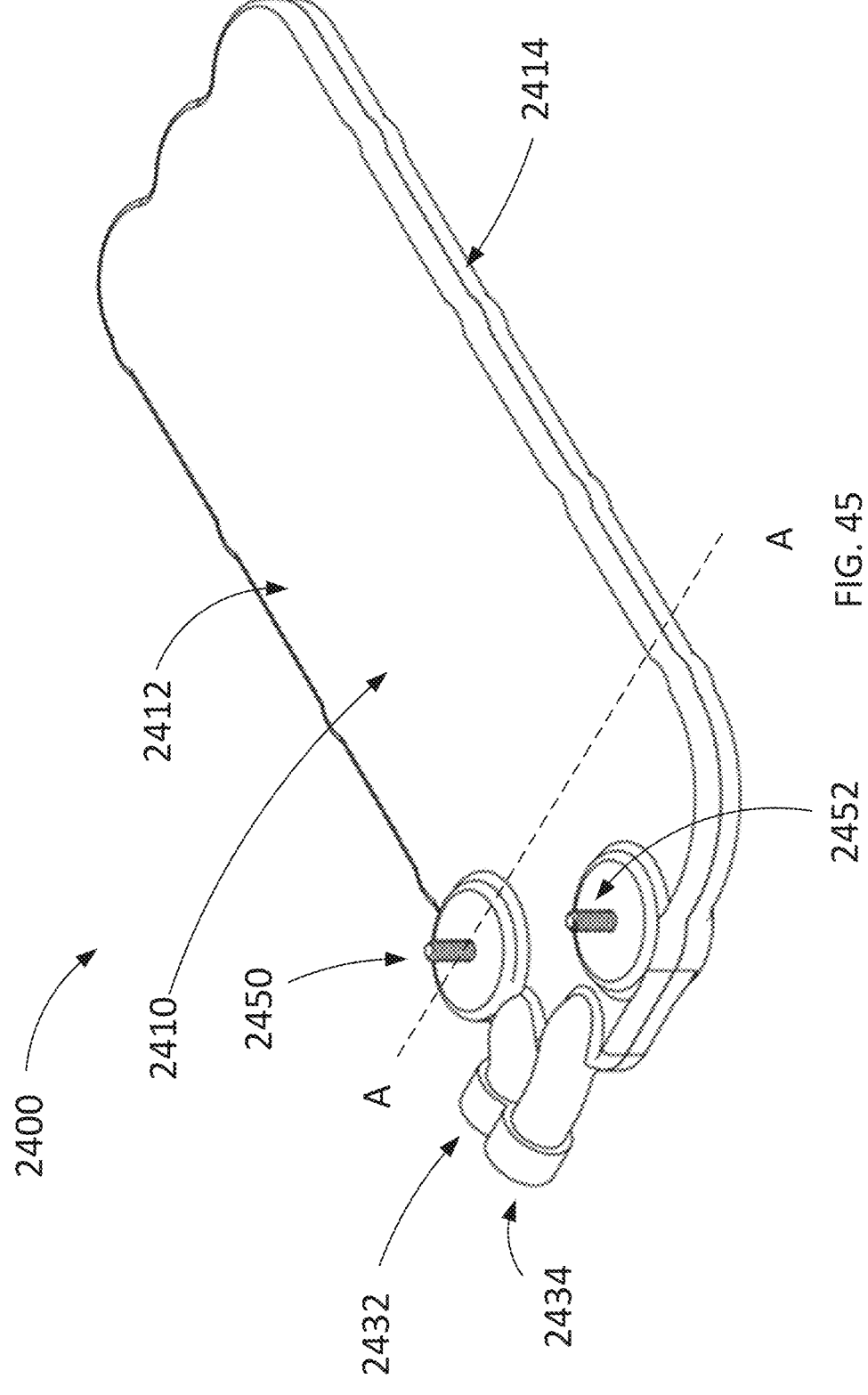
FIGS. 45-49 are various views of a fluid warmer system, according to an embodiment.
Figure 46:
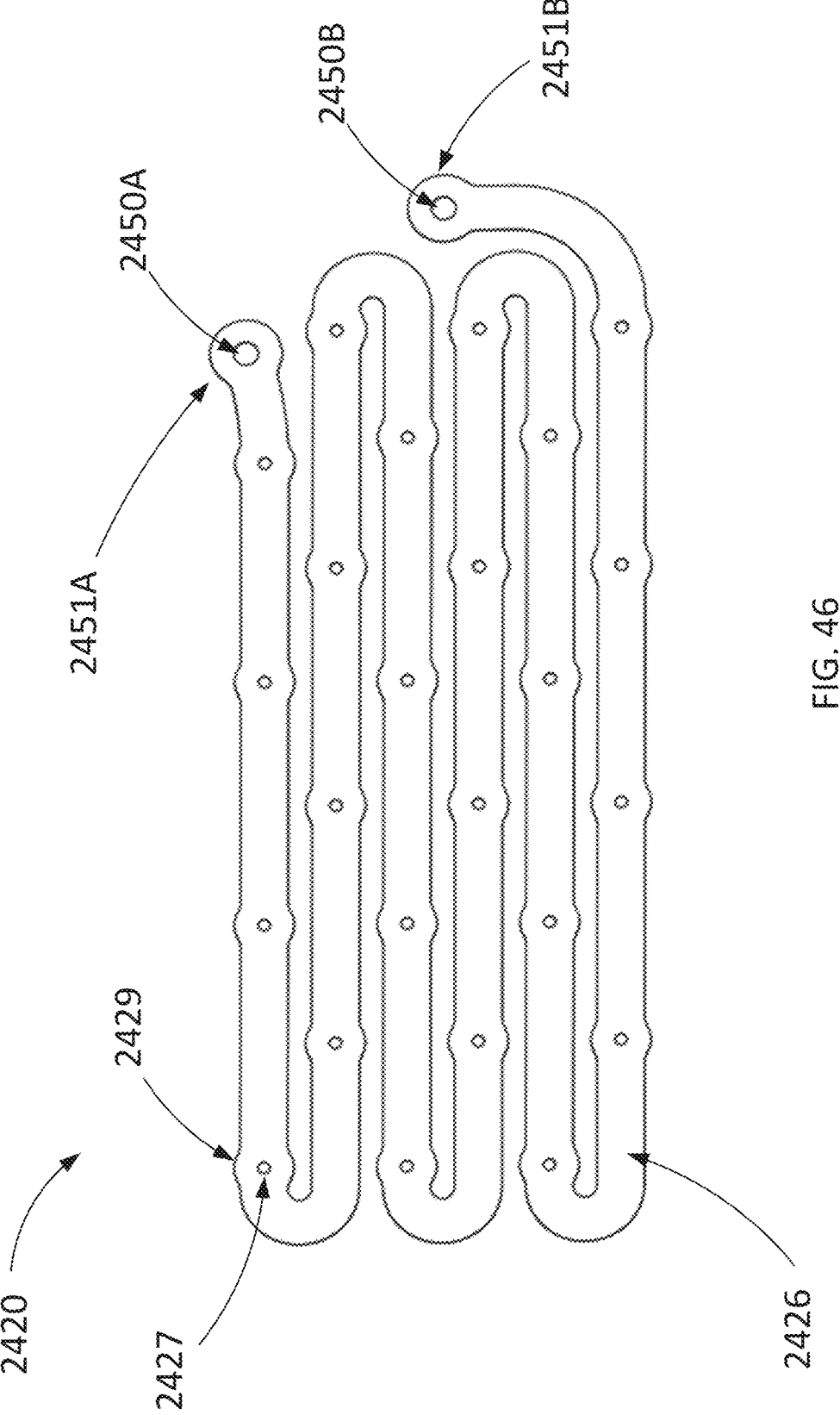
Figure 47:
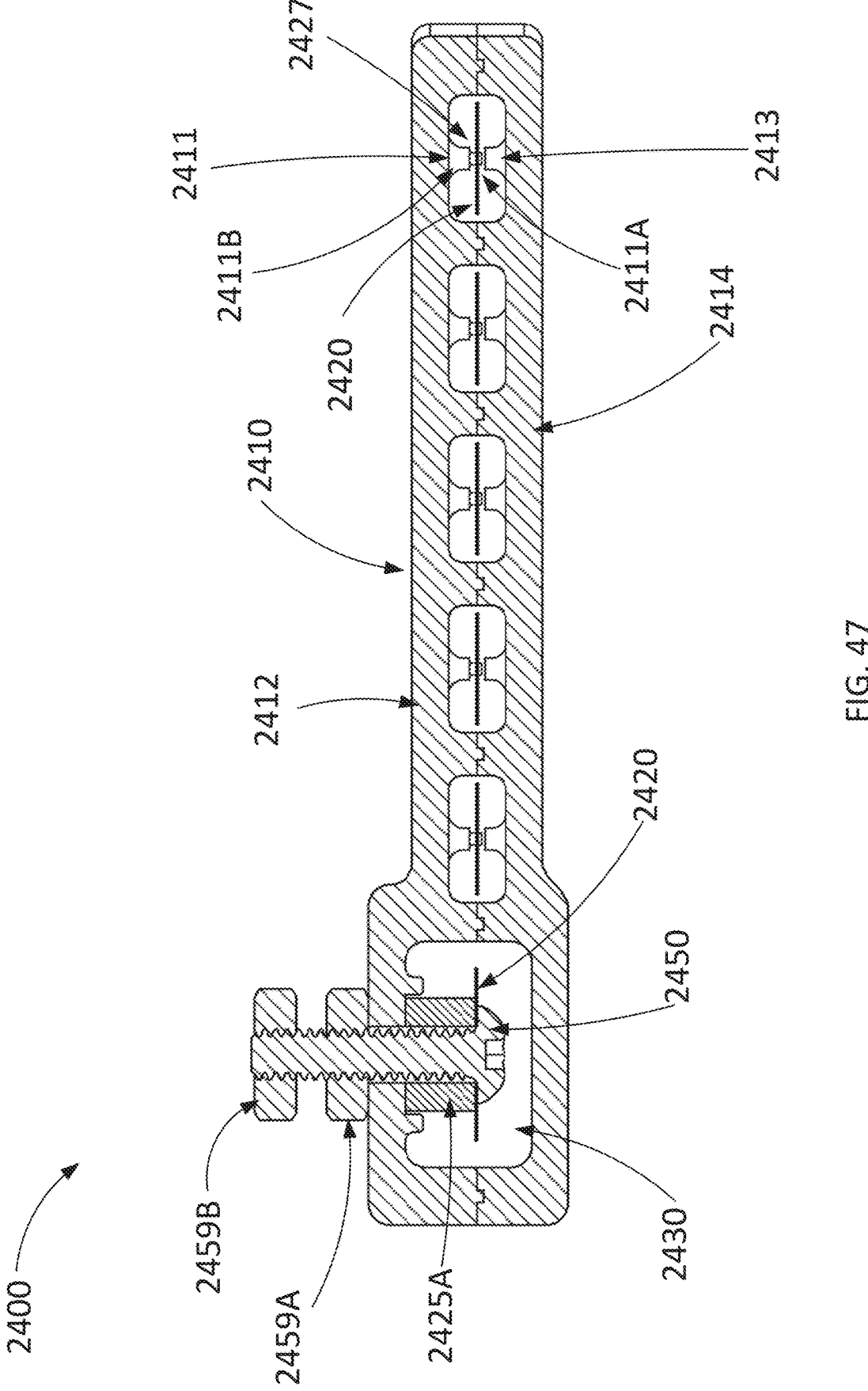
Figure 48:
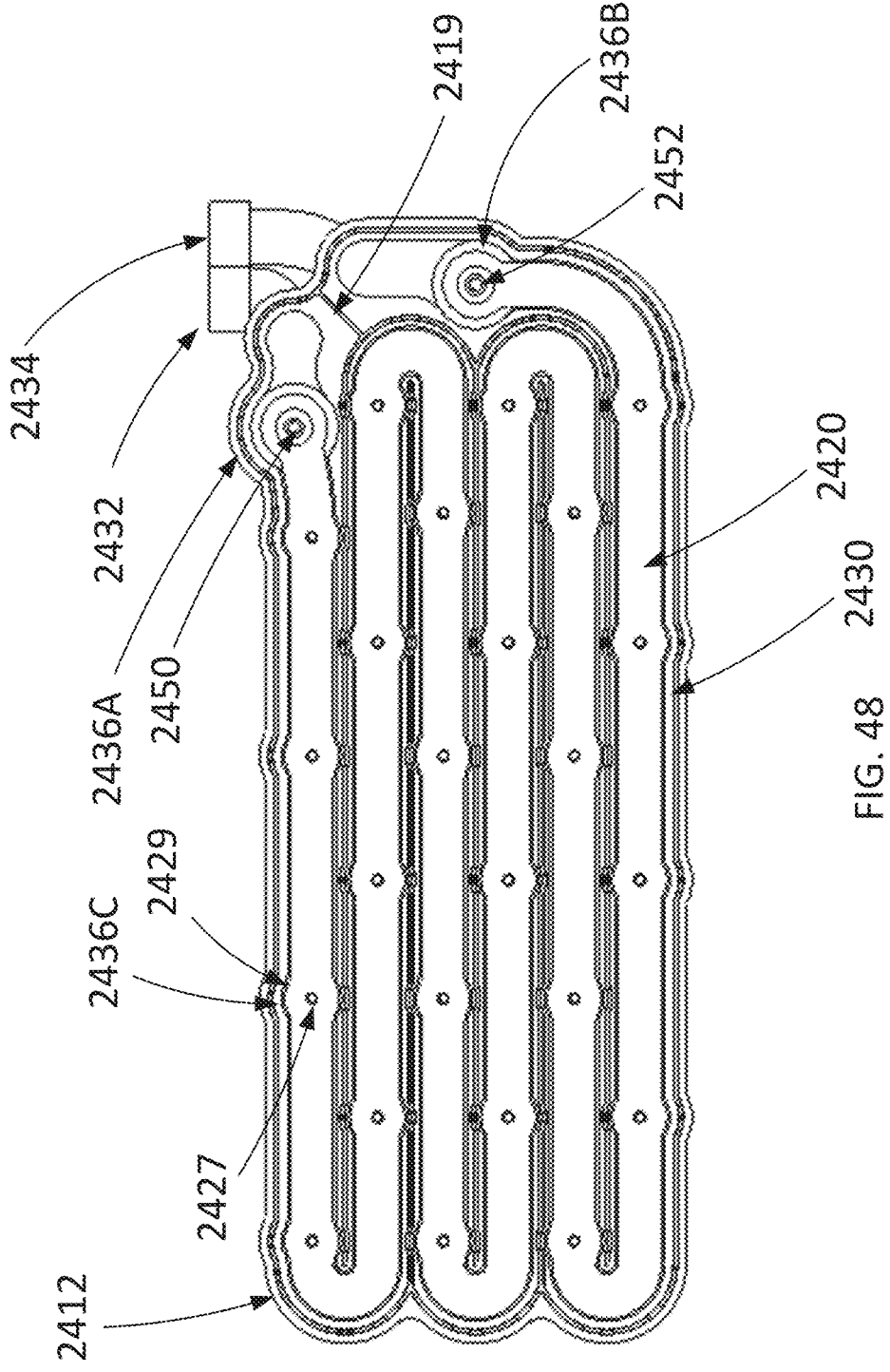

FIGS. 45-48 are various views of a system 2400. The system 2400 can be the same or similar in structure and/or function to any of the systems described herein, such as the system 100. For example, the system 2400 includes a housing 2410, an elongated heating element 2420, a first electrical connector 2450, and a second electrical connector 2452. The housing 2410 defines a fluid inlet 2432, a fluid outlet 2434, and a fluid channel 2430 extending from the fluid inlet 2432 to the fluid outlet 2434. The heating element 2420 is disposed within the fluid channel 2430. The housing 2410 includes a first portion 2412 and a second portion 2414. FIG. 45 is a perspective view of a bottom of the system 2400, FIG. 46 is a top view of the heating element 2420 of the system 2400, FIG. 47 is a cross-sectional illustration of the system 2400 taken along the line A-A in FIG. 45, and FIG. 48 is a top view of the system 2400 with a second portion 2414 of the housing 2410 not shown. Note that FIG. 45 does not show the first nut 2459A and the second nut 2459B shown in FIG. 47.

The first portion 2412 and the second portion 2414 can be coupled to each other to define and enclose the fluid channel 2430. As shown, in some embodiments, the first portion 2412 can include the fluid inlet 2432 and the fluid outlet 2434 and can define openings through which portions of the first electrical connector 2450 and the second electrical connector 2452 can extend. In some embodiments, the first portion 2412 can define the fluid channel 2430 and the second portion 2414 can be formed as a lid configured to form a sidewall of the fluid channel 2430 when coupled to the first portion 2412. For example, the first portion 2412 can include a surface forming a lower boundary of the fluid channel 2430, the second portion 2414 can include a surface forming an upper boundary of the fluid channel 2430, and the first portion 2412 and/or the second portion 2412 can include surfaces forming side boundaries of the fluid channel 2430 extending between the upper and lower boundaries.

The fluid channel 2430 can include or define a serpentine flow path such that fluid can flow smoothly from the fluid inlet 2432 to the fluid outlet 2434. When the system 2400 is fully assembled, fluid must flow along the full length of the fluid channel 2430 to travel from the fluid inlet 2432 to the fluid outlet 2434. For example, as shown in FIG. 48, the first portion 2412 and/or the second portion 2414 of the housing 2410 can include a dividing wall 2419 configured to prevent fluid from traveling between the fluid inlet 2432 and the fluid outlet 2434 without traveling along the full length of the fluid channel 2430. For example, the dividing wall 2419 can be disposed between the fluid inlet 2432 and the fluid outlet 2434 and/or between the first electrical connector 2450 and the second electrical connector 2452. Thus, the fluid inlet 2432 and the fluid outlet 2434 can be disposed on the same side of the housing 2410 (e.g., directly adjacent to each other), but fluid can only travel from the fluid inlet 2432 to the fluid outlet 2434 by flowing along the full length of the serpentine flow path defined by the fluid channel 2430.

As shown in FIG. 46, for example, the heating element 2420 can be formed as flat ribbon and can have a shape corresponding to the shape of at least a portion of the fluid channel 2430 (e.g., a serpentine shape). The heating element 2420 can be the same or similar in structure and/or function to any of the heating elements described herein, such as the heating element 120. Like the fluid channel 2430, the heating element 2420 can include a set of straight segments and a set of curved segments. Each straight segment can be coupled to an adjacent straight segment by a curved segment such that the heating element 2420 includes a series of alternating straight segments and curved segments. Although FIG. 46 shows the heating element 2420 as including six straight segments coupled via curved segments, the heating element 2420 and the fluid channel 2430 can include any suitable number of straight segments and curved segments.

The flat ribbon-shaped elongated heating element 2420 has a rectangular cross-section having a top surface 2426 (also referred to as an upper surface or a first surface), a bottom surface (also referred to as a lower surface or a second surface), and opposing side surfaces (also referred to as sidewalls or third and fourth surfaces). The cross-section of the flat ribbon-shaped elongated heating element 2120 has a larger width than height due to the top surface 2426 and the bottom surface being wider than the side surfaces are tall. The top surface 2426 and the bottom surface of the flat ribbon-shaped elongated heating element 2420 are disposed entirely in parallel planes such that the elongated heating element 2420 has a constant thickness between the top surface 2426 and the bottom surface from a first end to a second end of the elongated heating element 2420.

As shown in FIG. 46, the heating element 2420 can define a first through-hole 2450A and a second through-hole 2450B configured to receive portion of the first electrical connector 2450 and a portion of the second electrical connector 2452, respectively. The first through-hole 2450A (also referred to as a first electrical connector through-hole) and the second through-hole 2450B (also referred to as a second electrical connector through-hole) can be disposed at or near a first end and a second end of the heating element 2420, respectively.

Also as shown in FIG. 47, the electrical connection or interface (e.g., the electrical input) with the heating element 2420 is located within the fluid channel 2430. The first electrical connector 2450 and the second electrical connector 2452 can each have a first portion having a larger diameter than the respective through-hole 2450A,B disposed in contact with a first side of the heating element 2420 (e.g., the upper surface) and a second portion configured to extend through the respective through-hole 2450A,B and be fixedly secured relative to the housing 2410. For example, each of the first electrical connector 2450 and the second electrical connector 2452 can be formed as a screw disposed partially within the fluid channel 2430 such that the screw head is disposed in the fluid channel 2430 and a threaded portion of the screw extends through an opening defined in the first portion 2412 and away from the housing 2410. As shown in FIG. 47, the heating element 2420 can be disposed and retained between a larger diameter first portion of the first electrical connector 2450 and a spacer 2425A (also referred to as a first spacer or a support member), such as a bushing. The spacer 2425A can be conductive or non-conductive. In some embodiments, the spacer 2425A can be the same as or similar to any of the support members described herein, such as conductive support member 140. In some embodiments, the spacer 2425A can be optional. The spacer 2425A can define a passageway within which a portion of the threaded portion of the first electrical connector 2450 can be disposed. For example, the heating element 2420 can be disposed in contact with a surface of the screw head (e.g., an upper surface of the screw head facing the second threaded portion) of the first electrical connector 2450 and a lower surface of the spacer 2425A. The spacer 2425A can be retained between the heating element 2420 and the first portion 2412 of the housing 2410 and the first electrical connector 2450 and the spacer 2425A can be fixedly secured relative to the first portion 2412 of the housing 2410 and the heating element 2420 by a securing member disposed outside of the housing 2410, such as at least one nut 2459A engaged with the threaded portion of the first electrical connector 2450 disposed on an outer surface of the housing 2410. In some embodiments, the arrangement of the spacer 2425A relative to the housing 2410, the heating element 2420, and the first electrical connector 2450 can fluidically isolate the second portion of the first electrical connector 2450 (e.g., the threaded portion) from fluid within the fluid channel 2430 such that the only portion of the first electrical connector 2450 exposed to fluid in the fluid channel 2430 is the first portion (e.g., the screw head).

In some implementations, a wire or other electrically conductive component configured to transmit electricity without generating heat can be electrically and physically coupled to the first electrical connector 2450 and can be secured in contact with the first electrical connector 2450 by, for example, a second nut 2459B engaged with the threaded portion of the first electrical connector 2450. Although not shown, the second electrical connector 2450 can include a screw head disposed on a first side of the heating element 2420 and a threaded portion received within the through-hole 2450B, extending through a passageway of a second spacer disposed between a second side of the heating element 2420 and a wall of the housing 2410 defining the fluid channel 2430, extending through an opening in the housing 2410, and coupled to a securing member (e.g., at least one nut) and an electrically conductive component similarly as described with respect to the first electrical connector 2450.

As shown in FIG. 47, the housing 2410 can also include support features for supporting (e.g., providing rigid support for) the heating element 2420 within the channel 2430. The support features can be non-conductive (e.g., plastic). The support features can be formed as protruding features (e.g., protruding posts) and can be the same or similar in structure and/or function to any of the protruding features described herein. For example, the first portion 2412 of the housing 2410 can include a first set of protruding features 2411 and the second portion 2414 of the housing 2410 can include a second set of protruding features 2413. Each protruding feature of the first set of protruding features 2411 and the second set of protruding features 2413 can extend into the fluid channel 2430 from a respective opposing surface of a wall of the housing 2410 defining the fluid channel 2430 (e.g., an upper surface defining an upper boundary of the channel 2430 or a lower surface defining a lower boundary of the channel 2430) to supportively couple to and/or engage with the heating element 2420 such that the heating element 2420 is secured in place between and spaced from the opposing wall surfaces.

As shown in FIG. 46, the heating element 2420 defines a set of support through-holes 2427 (also referred to as openings) spaced along the heating element 2420. Each through-hole 2427 is configured to receive a portion of a protruding feature 2411 of the set of protruding features 2411 (shown in FIG. 47) of the first portion 2412 of the housing 2410. As shown in FIG. 47, in some implementations, each protruding feature 2411 of the first set of protruding features 2411 can be disposed in the fluid channel 2430 and can extend (e.g., perpendicularly) through the through-holes 2427 defined in the elongated heating element 2420 to engage with and support the elongated heating element 2420 within the fluid channel 2430. As shown, each the protruding feature 2411 includes a narrow portion 2411A and a wide portion 2411B. The narrow portion 2411A can have a diameter that is smaller than the diameter of an associated through-hole 2427 in the elongated heating element 2420 and the wider portion 2411B can have a diameter that is larger than the diameter of the associated through-hole 2427 in the elongated heating element 2420 such that the narrow portion 2411A can extend through the through-hole 2427 and the elongated heating element 2420 can be retained and/or prevented from moving away from the second portion 2414 due to contact with the wide portion 2411B.

Each protruding feature 2413 of the second set of protruding features 2413 can be disposed in the fluid channel 2430 and can extend (e.g., perpendicularly) relatively to the upper and/or lower surface of the heating element 2420. Each protruding feature 2413 of the second set of protruding features 2413 can be disposed coaxially with a protruding feature 2411 of the first set of protruding features 2411 and a through-hole 2427 of the set of through-holes 2427. In some implementations, a free end of each protruding feature 2413 of the second set of protruding features 2413 can be disposed in contact with a free end of a protruding feature 2411 of the first set of protruding features 2411 (e.g., the narrow portion 2411A). In some implementations, a portion (e.g., a free end) of each protruding feature 2413 of the second set of protruding features 2413 can have a diameter that is larger than the diameter of the associated through-hole 2427 and/or a diameter of the narrow portion 2411A such that the heating element 2420 is retained within the fluid channel 2430 and spaced from the opposing upper and lower channel wall portions and from the opposing sidewalls of the fluid channel 2430. For example, the heating element 2420 can be retained between the protruding features 2413 and the wider portions 2411B and the narrow portions 2411A can be disposed within the through-holes 2427.

In some embodiments, rather than or in addition to the protruding features 2411 of the first set of protruding features 2411 including a narrow portion 2411A and a wide portion 2411B, the protruding features 2413 of the second set of protruding features 2413 can include a narrow portion and a wide portion such that at least some of the protruding features 2413 of the second set of protruding features 2413 include a narrow portion disposed within a respective through-hole 2427 of the set of through-holes. In some embodiments, instead of each of the first portion 2412 and the second portion 2414 including a protruding feature associated with each through-hole 2427, each through-hole 2427 can be associated with a single protrusion (e.g., included in the first portion 2412 or the second portion 2414) sized to fit tightly within the through-hole 2427 to support and retain the heating element 2420 within the fluid channel 2430. In some embodiments, instead of the heating element 2420 include through-holes 2427 each configured to receive a portion of a protruding feature, the heating element 2420 can include no through-holes 2427 and can instead be held in a centered position within the fluid channel 2430 via a set of pairs of opposing protruding features contacting opposite sides of the heating element 2420. Each pair of the set of pairs of opposing protruding features can include a protruding feature of the first portion 2412 and a protruding feature of the second portion 2414. In some embodiments, the support features can be or include any suitable features (such as any of the protruding features described herein) configured to support the heating element 2420 within the fluid channel 2430 (e.g., centered) such that sufficient surface area of the heating element 2420 is exposed for contact with fluid flowing through the fluid channel to avoid an undesired buildup of heat and/or unacceptably high heating element 2420 and/or fluid temperatures. Additionally, the support features can be any suitable features configured to support the heating element 2420 within the fluid channel 2430 (e.g., centered) such that no portion of the heating element 2420 is sufficiently large and disposed out of contact with fluid flow or in a location with limited fluid flow contact to avoid an undesired buildup of heat and/or unacceptably high heating element 2420 and/or fluid temperatures.

The first electrical connector 2450, the first spacer 2425A, the second electrical connector 2452, the second spacer, and the protruding features 2411,2413 are configured to support the elongated heating element 2420 such that the elongated heating element 2420 is disposed within the fluid channel 2430 (e.g., entirely disposed within the fluid channel 2430). The elongated heating element 2420 can be supported within the fluid channel 2430 such that a space is defined for fluid flow between each of the first side surface, the second side surface, the upper surface, and the lower surface of the elongated heating element 2420 and the channel wall of the housing 2410 defining the fluid channel 2430 and fluid flowing through the channel 2430 can contact each of the first side surface, the second side surface, the upper surface, and the lower surface. The entire elongated heating element 2420 is disposed within the fluid channel 2430 (e.g., from a first end to a second end of the elongated heating element 2420). In some embodiments, no portion of the elongated heating element 2420 directly contacts any portion of the housing 2410 (e.g., any portion of the channel wall of the housing 2410 defining the fluid channel 2430). In some embodiments, no portion of the elongated heating element 2420 directly contacts any portion of the housing 2410 (e.g., any portion of the channel wall of the housing 2410 defining the fluid channel 2430) except for the protruding features 2411,2413. In some embodiments, rather than being formed as separate components, the first spacer 2425A and/or the second spacer can be monolithically formed (e.g., molded) with the housing 2410 (e.g., with the first portion 2412).

The protruding features 2411, 2413 are configured to support the heating element 2420 such that the heating element 2420 is centered in the fluid channel 2430 (e.g., equidistant from the opposing upper and lower channel wall portions and/or equidistance from opposing sidewalls of the channel 2430). The distance between each surface of the heating element 2420 and the wall portion of the fluid channel 2430 facing that surface can substantially the same throughout the fluid channel 2430, throughout the portion of the fluid channel 2430 within which the heating element 2420 is disposed, and/or throughout similarly shaped segments of the fluid channel 2430 (e.g., throughout straight segments and/or throughout curved segments).

To maintain a substantially constant cross-sectional area of the fluid channel 2430 through which fluid can flow along the length of the fluid channel 2430, or at least the portion of the fluid channel 2430 within which the heating element 2420 is disposed, the fluid channel 2430 can include increased cross-sectional area portions associated with the first electrical connector 2450, the second electrical connector 2452, and the protruding members 2411 and 2413 that are disposed within the fluid channel 2430 and obstruct a portion of the flow path.

For example, the fluid channel 2430 can include increased cross-sectional area portions (e.g., having increased width and/or height as defined by the housing 2410) so that the cross-sectional area of the fluid channel 2430 through which fluid can flow remains substantially constant through the fluid channel 2430 (e.g., from the inlet 2432 to the outlet 2434, from the first end to the second end of the heating element 2420, and/or from the first electrical connector 2450 to the second electrical connector 2452) even though some portions of the fluid channel 2430 house fluid obstructing components (e.g., the first electrical connector 2450, the second electrical connector 2452, and/or the protruding members 2411 and 2413). For example, the cross-sectional area of the increased cross-sectional area portions within which the fluid obstructing components are disposed can be between about 50% and about 400%, between about 75% and about 200%, between about 90% and about 150%, and/or between about 75% and about 125% of the cross-sectional area of the remaining portions of the fluid channel 2430.

In some embodiments, as shown in FIG. 48, the fluid channel 2430 can have an increased width portion associated with each of the first electrical connector 2450, the second electrical connector 2452, and each pair of protruding members 2411, 2413. In some embodiments, the fluid channel 2430 can have a constant width along straight segments and a constant inner and outer diameter along the curved segments, except for the increased width portions associated with each of the first electrical connector 2450, the second electrical connector 2452, and each pair of protruding members 2411, 2413. For example, the fluid channel 2430 can include an increased width portion 2436A aligned with (e.g., surrounding and/or coaxial with) the first electrical connector 2450, an increased width portion 2436B aligned with (e.g., surrounding and/or coaxial with) the second electrical connector 2450, and an increased width portion 2436C of a set of increased width portions 2436C aligned with (e.g., surrounding and/or coaxial with) with each pair of protruding members 2411, 2413. As shown in FIG. 46, each of the increased width portions 2436A, 2436B, and 2436C can have a rounded shape such that each increased width portion 2436A, 2436B, and 2436C has a circular or partially circular area and/or the associated opposing channel wall surface portions are rounded. In some embodiments, the shapes of the increased width portions 2436A, 2436B, and 2436C can be any suitable shape that is conducive to fluid flow through the channel 2430 (e.g., partially spherical, having a wall portion forming an increasing straight tapered segment and a decreasing straight tapered segment).

Additionally, the heating element 2420 can include increased cross-sectional area portions (e.g., having increased width and/or height) so that the cross-sectional area of the fluid channel 2430 through which fluid can flow remains substantially constant along the length of the fluid channel 2430 and/or the heating element 2420 (e.g., from the inlet 2432 to the outlet 2434, from the first end to the second end of the heating element 2420, and/or from the first electrical connector 2450 to the second electrical connector 2452). For example, as shown in FIGS. 46 and 48, the heating element 2420 can also include an increased width portion associated with each of the first electrical connector 2450, the second electrical connector 2452, and each pair of protruding members 2411, 2413 (e.g., associated with each of the first through-hole 2450A, the second through-hole 2450B, and each through-hole 2427 of the set of support through-holes 2427). In some embodiments, the heating element 2420 can have a constant width along straight segments and a constant inner and outer diameter along the curved segments, except for the increased width portions associated with each of the first through-hole 2450A, the second through-hole 2450B, and each through-hole 2427 of the set of support through-holes 2427. For example, the heating element 2420 can include an increased width portion 2451A aligned with (e.g., surrounding and/or coaxial with) the first through-hole 2450A, an increased width portion 2451B aligned with (e.g., surrounding and/or coaxial with) the second through-hole 2450B, and an increased width portion 2429 of a set of increased width portions 2429 aligned with (e.g., surrounding and/or coaxial with) with each through-hole 2427 of the set of support through-holes 2427. As shown in FIG. 46, each of the increased width portions 2451A, 2451B, and 2429 can have a rounded shape such that the upper and lower surface portions of each increased width portion 2451A, 2451B, and 2429 includes a circular or partially circular area and the sides extending between the upper and lower surface portions are curved. In some embodiments, the shapes of the increased width portions 2451A, 2451B, and 2429 can be any suitable shape that is conducive to fluid flow through the channel 2430.

In some embodiments, the shape of the increased width portions 2451A, 2451B, and 2429 of the heating element 2420 can correspond to the respective increased width portions 2436A, 2436B, and 2436C of the fluid channel 2430 and can be shaped and sized such that the cross-sectional area of the fluid channel 2430 through which fluid can flow is substantially constant throughout the length of the heating element 2420 and/or the fluid channel 2430. For example, the length of the gap between each sidewall of the heating element 2420 and the sidewall defining the fluid channel 2430 facing that heating element 2420 sidewall can be substantially the same within the increased width portions 2436A, 2436B, and 2436C as in the remainder of the fluid channel 2430 (e.g., the portions adjacent to the increased width portions 2436A, 2436B, and 2436C).

In some embodiments, although not shown, the fluid inlet 2432 and the fluid outlet 2434 can be disposed such that a central axis of each is parallel to a central axis of the screw forming the first electrical connector 2450 and a central axis of the screw forming the second electrical connector 2452. The fluid channel 2430 includes a 90 degree turn between the fluid inlet 2432 and the first electrical connector 2450 and a 90 degree turn between the second electrical connector 2450 and the fluid outlet 2434. In some implementations, rather than including one or both of the 90 degree turns, the fluid channel 2430 include any suitable shape segments having any suitable orientations. For example, the fluid inlet 2432 and/or the fluid outlet 2434 can have a central axis that is either parallel, perpendicular, or disposed at another angle relative to the central axis of the first electrical connector 2450 and/or the second electrical connector 2452, such as is shown in FIG. 45, and the fluid channel 2430 can include any suitable segment shapes and orientations such that the first electrical connector 2450 has a portion (e.g., a screw head) that remains disposed within the fluid channel 2430 and can be surrounded by fluid flowing through the fluid channel 2430 and such that the heating element 2420 is disposed within the fluid channel 2430 and can be surrounded by fluid flowing through the fluid channel 2430.

Figure 49:
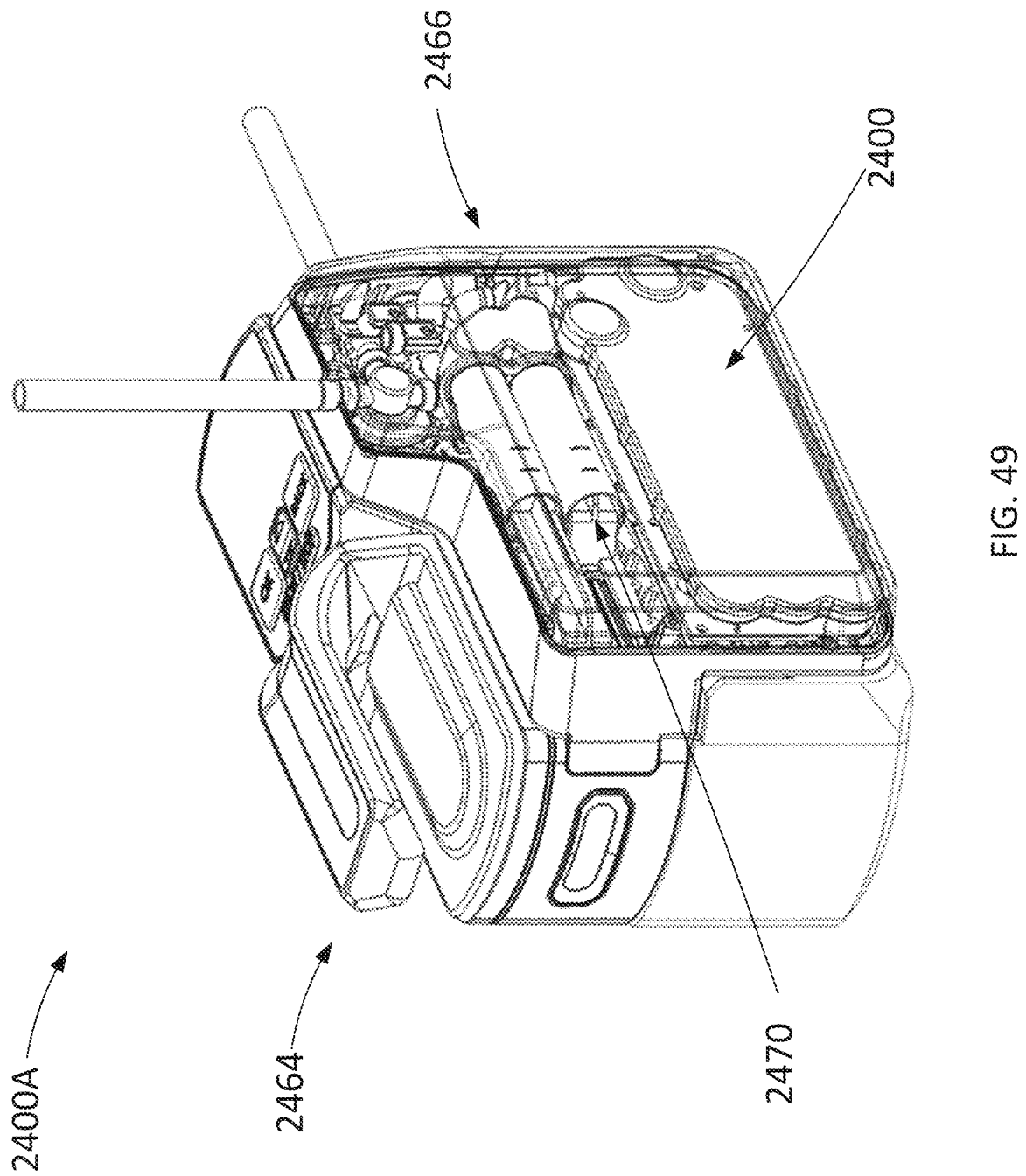

In some embodiments, the warmer system 2400 can be used as a stand-alone system or device. In some embodiments, the warmer system 2400 can be used as part of a rapid infuser system. For example, FIG. 49 is a perspective view of a rapid infuser system 2400A (also referred to as an infusion assembly). The rapid infuser system 2400A can be the same or similar in structure and/or function to any of the rapid infuser systems described herein, such as the infusion assembly 2065. For example, the rapid infuser system 2400A can include a disposable portion 2466 and a reusable drive assembly portion 2464. For example, the disposable portion 2466 can be the same or similar in structure and/or function to the disposable portion 166 and the drive assembly portion 2464 can be the same or similar in structure and/or function to the drive assembly portion 164 described above with respect to the system 100. The disposable portion 2466 can include or be coupled to the warmer system 2400. The disposable portion 2466 also includes a fluid pumping assembly 2470 (e.g., a dual syringe pump) that can be the same or similar in structure and/or function to the fluid pumping assembly 170 and can be fluidically coupled to the fluid channel 2430 of the warmer system 2400 such that fluid flows through the fluid channel 2430 of the warmer system 2400 after being expelled from the fluid pumping assembly 2470. In use, fluid can be drawn into the fluid pumping assembly 2470 via inlet tubing, be expelled from the fluid pumping assembly 2470 into the fluid channel 2430 of the warmer system 2400, and flow into outlet tubing (e.g., to a patient). In some embodiments, the fluid pumping assembly 2470 and the warmer system 2400 are included in a single use cartridge or fluid delivery assembly that can be removably coupled to the reusable drive assembly portion 2464 and/or a warmer controller or drive assembly.

Figure 50:
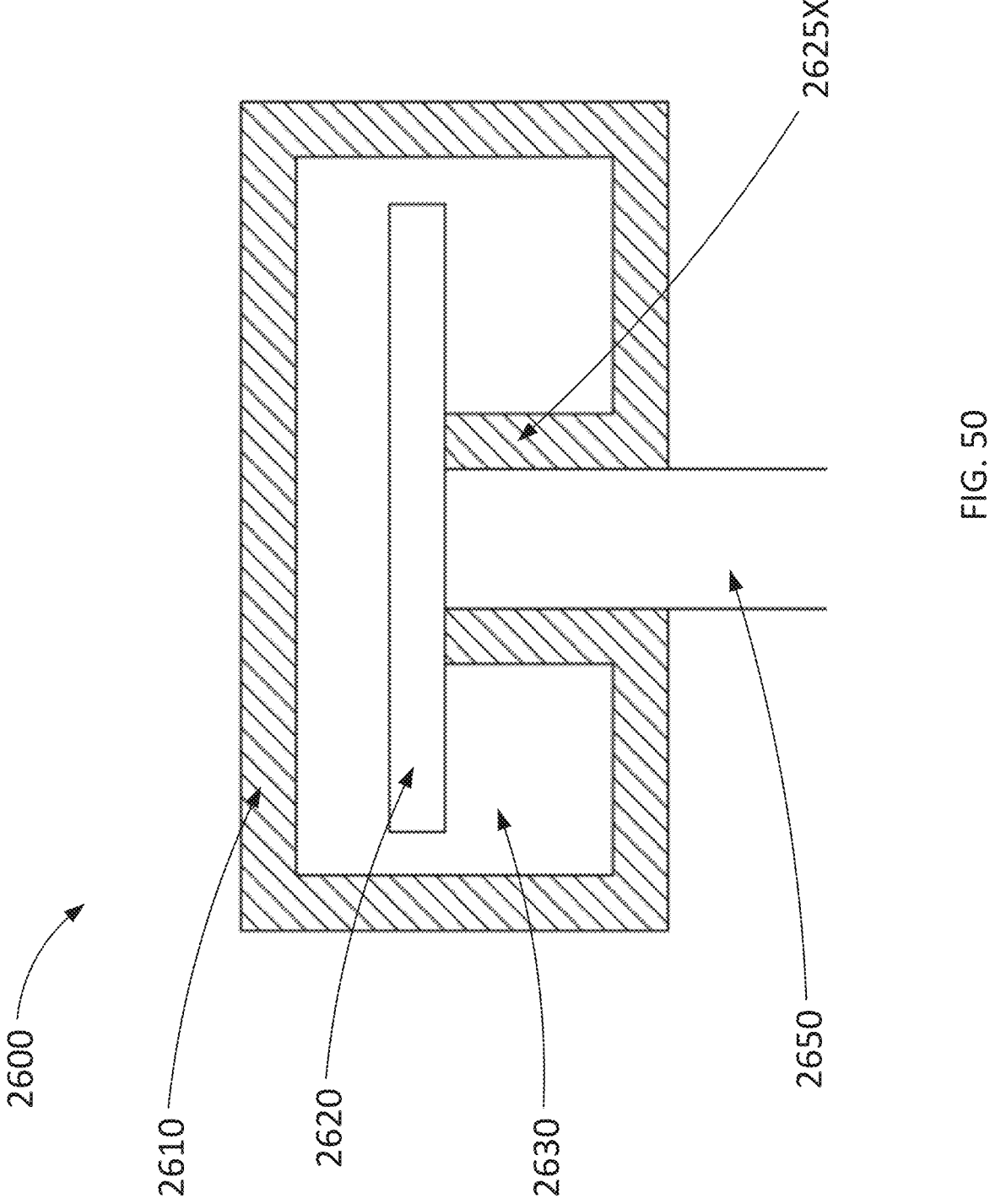
FIG. 50 is a cross-sectional illustration of a portion of a fluid warmer system, according to an embodiment.

In some embodiments, an electrical connector can be coupled directly to the heating element within a fluid channel of a housing without being exposed to fluid flow within the fluid channel. For example, FIG. 50 is a schematic cross-sectional illustration of a portion of a fluid warmer system 2600. The fluid warmer system 2600 can be the same or similar in structure and/or function to any of the fluid warmer systems described herein, such as the fluid warmer system 100. For example, the fluid warmer system 2600 includes a housing 2610 defining a fluid channel 2630, a heating element 2620 disposed within the fluid channel 2630, a first electrical connector 2650, and a second electrical connector (not shown). The housing 2610, the heating element 2620, the first electrical connector 2650, and the second electrical connector can be the same or similar in structure and/or function to any of the housings, the heating elements, or electrical connectors, respectively, described herein. As shown in FIG. 50, the first electrical connector 2650 can extend from an area external to the housing 2610, through a portion of the fluid channel 2630, and into physical and electrical contact with the heating element 2620. For example, an end of the first electrical connector 2650 can be welded or riveted directly to a surface of the heating element 2620. The first electrical connector 2650 can be, for example, a wire.

In some embodiments, the portion of the first electrical connector 2650 disposed within the fluid channel 2630 (e.g., extending from a sidewall of the housing 2610 forming a boundary of the fluid channel 2630 to the heating element 2620 which is disposed within the fluid channel 2630 and not in contact with the sidewalls of the housing 2610 forming the boundaries of the fluid channel 2630) can be disposed such that fluid within the fluid channel 2630 can contact the first electrical connector 2650. In some embodiments, as shown in FIG. 50, the portion of the first electrical connector 2650 disposed within the fluid channel 2630 can be disposed within an insulative portion 2625X that can be coupled to and extend from a sidewall of the fluid channel 2630 to the heating element 2620. The insulative portion 2625X can be configured to fluidically isolate the first electrical connector 2650 from fluid within the fluid channel 2630. For example, as shown in FIG. 50, the insulative portion 2625X defines a through-hole within which a portion of the first electrical connector 2650 can be disposed. The insulative portion 2625X can also be coupled to the heating element 2620 such that the insulative portion 2625X provides support to the heating element 2620 to maintain the heating element 2620 within the fluid channel 2630 (e.g., centered) and out of contact with the sidewalls forming the boundaries of the fluid channel 2630. In some embodiments, the insulative portion 2625X can have a cylindrical shape. In some embodiments, the insulative portion 2625X can be the same or similar in structure and/or function to any of the spacers described herein. The insulative portion 2625X can be formed of the same or different materials as the housing 2610. In some embodiments, the insulative portion 2625X can be monolithically formed with the housing 2610 (e.g., molded). Although not shown, the second electrical connector can be the same or similar in structure and/or function to the first electrical connector 2650 and can be partially disposed within a second insulative portion that is the same or similar in structure and/or function to the insulative portion 2625X.

Some embodiments described herein (e.g., embodiments including or couplable to a controller such as the controller 161) relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments (e.g., embodiments including or couplable to a controller such as the controller 161) and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. A system, comprising:
   a housing defining a fluid inlet and a fluid outlet, the housing including one or more channel walls defining a fluid channel extending from the fluid inlet to the fluid outlet;
   an elongated heating element disposed entirely within the fluid channel and having an outer surface spaced from each of the one or more channel walls such that fluid within the fluid channel can flow between the one or more channel walls and the outer surface of the elongated heating element;
   a first electrical connector coupled to a first portion of the elongated heating element, the first electrical connector including a portion extended through at least one of the one or more channel walls of the housing; and
   a second electrical connector coupled to a second portion of the elongated heating element, the second electrical connector including a portion extended through at least one of the one or more channel walls of the housing,
   each of the first electrical connector and the second electrical connector configured to be electrically coupled to a power source such that energy can be provided from the power source to the elongated heating element via one of the first electrical connector or the second electrical connector to increase the temperature of the elongated heating element,
   the fluid channel includes a first portion, a second portion, and a third portion between the first portion and second portion, the first portion of the fluid channel and the second portion of the fluid channel each having at least one of an increased width or an increased height compared to the third portion of the fluid channel, the first portion of the elongated heating element disposed in the first portion of the fluid channel, the second portion of the elongated heating element disposed in the second portion of the fluid channel.

2. The system of claim 1, wherein the first electrical connector and the second electrical connector support the elongated heating element within the fluid channel.

3. The system of claim 1, further comprising:

a first support member and a second support member each configured to support the elongated heating element within the fluid channel.

4. The system of claim 1, further comprising:

a support member configured to support the elongated heating element within the fluid channel, the support member defining a through-hole within which a portion of the first electrical connector is disposed.

5. The system of claim 4, wherein the support member is insulative and configured to isolate fluid within the fluid channel from the portion of the first electrical connector disposed within the through-hole of the support member.

6. The system of claim 4, wherein the support member is conductive.

7. The system of claim 1, wherein the cross-sectional area of the fluid channel through which fluid can flow is substantially constant along the length of the elongated heating element.

8. The system of claim 1, wherein the first portion of the fluid channel is associated with the first electrical connector and the second portion of the fluid channel is associated with the second electrical connector.

9. The system of claim 1, further comprising:

a set of protruding features disposed in the fluid channel and extending away from the one or more channel walls into supportive contact with the elongated heating element, the one or more channel walls defines a set of increased width portions of the fluid channel, each increased width portion of the fluid channel associated with a protruding feature of the set of protruding features.

10. The system of claim 1, wherein a portion of the first electrical connector is disposed within the fluid channel such that fluid within the fluid channel contacts the first electrical connector.

11. The system of claim 1, wherein the elongated heating element is formed as a flat ribbon.

12. The system of claim 1, wherein the outer surface of the elongated heating element includes a first surface disposed in a first plane and a second surface disposed in a second plane parallel to the first plane, a distance between the first surface and a channel wall portion defining a boundary of the fluid channel facing the first surface and a distance between the second surface and a channel wall portion defining a boundary of the fluid channel facing the second surface are substantially constant along the entire length of the elongated heating element.

13. The system of claim 1, wherein the first electrical connector has a large diameter such that the first electrical connector has a lower gauge equivalency than the elongated heating element.

14. The system of claim 1, wherein the fluid channel has a cross-section with a maximum diameter of about 0.375 inches.

15. A system, comprising:

a housing defining a fluid inlet, a fluid outlet, and a fluid channel extending from the fluid inlet to the fluid outlet;

an elongated heating element disposed within the fluid channel and having an overall shape that corresponds to a shape of at least a portion of the fluid channel;

a first support member coupled to the elongated heating element at a first location;

a second support member coupled to the elongated heating element at a second location, the first support member and the second support member configured to support the elongated heating element within the fluid channel such that fluid can flow between a channel wall of the housing defining the fluid channel and the elongated heating element along two opposing side portions of the elongated heating element;

a first electrical connector electrically coupled to the first support member; and a second electrical connector electrically coupled to the second support member, each of the first electrical connector and the second electrical connector configured to be electrically coupled to a power source such that energy can be provided from the power source to the elongated heating element via one of the first electrical connector or the second electrical connector to increase the temperature of the elongated heating element.

16. The system of claim 15, wherein the elongated heating element has a first side surface, a second side surface, an upper surface, and a lower surface, the two opposing side portions of the elongated heating element including the first side surface and the second side surface or the upper surface and the lower surface, the first support member and the second support member configured to support the elongated heating element within the fluid channel such that at least three surfaces of the first side surface, the second side surface, the upper surface, and the lower surface are spaced from the channel wall of the housing defining the fluid channel and fluid can flow between the channel wall and each of the at least three surfaces.

17. The system of claim 16, wherein a distance between the first side surface and a portion of the channel wall of the housing defining the fluid channel facing the first side surface is substantially the same as a distance between the second side surface and a portion of the channel wall of the housing defining the fluid channel facing the second side surface.

18. The system of claim 16, wherein a distance between the first side surface and a portion of the channel wall of the housing defining the fluid channel facing the first side surface and a distance between the second side surface and a portion of the channel wall of the housing defining the fluid channel facing the second side surface are substantially constant along the entire length of the elongated heating element.

19. The system of claim 15, wherein the fluid channel includes an increased cross-sectional area portion within which a first end of the heating element is disposed such that the cross-sectional area of the fluid channel through which fluid can flow is substantially the same in the increased cross-sectional area portion as in portions of the fluid channel within which the first end of the heating element is not disposed.

20. The system of claim 15, wherein the cross-sectional area of the fluid channel through which fluid can flow is substantially constant along the length of the elongated heating element.

* * * * *